United States Patent
Ho et al.

(10) Patent No.: US 9,803,022 B2
(45) Date of Patent: *Oct. 31, 2017

(54) MESOTHELIN DOMAIN-SPECIFIC MONOCLONAL ANTIBODIES AND USE THEREOF

(71) Applicant: The United States of America, as represented by the Secretary, Department of Health and Human Services, Washington, DC (US)

(72) Inventors: Mitchell Ho, Urbana, MD (US); Ira H. Pastan, Potomac, MD (US); Yen T. Phung, Annandale, VA (US); Yifan Zhang, Haymarket, VA (US); Wei Gao, Rockville, MD (US); Raffit Hassan, Gaithersburg, MD (US)

(73) Assignee: The United States of America, as represented by the Secretary, Department of Health and Human Services, Washington, DC (US)

( * ) Notice: Subject to any disclaimer, the term of this patent is extended or adjusted under 35 U.S.C. 154(b) by 5 days.

This patent is subject to a terminal disclaimer.

(21) Appl. No.: 15/141,006

(22) Filed: Apr. 28, 2016

(65) Prior Publication Data

US 2016/0229919 A1    Aug. 11, 2016

Related U.S. Application Data

(63) Continuation of application No. 14/421,599, filed as application No. PCT/US2013/055273 on Aug. 16, 2013, now Pat. No. 9,409,992.

(60) Provisional application No. 61/691,719, filed on Aug. 21, 2012.

(51) Int. Cl.
| | |
|---|---|
| *C07K 16/30* | (2006.01) |
| *A61K 47/00* | (2006.01) |
| *G01N 33/53* | (2006.01) |
| *A61K 47/48* | (2006.01) |
| *G01N 33/574* | (2006.01) |
| *A61K 49/00* | (2006.01) |
| *A61K 51/10* | (2006.01) |
| *C07K 14/725* | (2006.01) |
| *C07K 16/28* | (2006.01) |
| *C07K 16/46* | (2006.01) |
| *A61K 39/00* | (2006.01) |

(52) U.S. Cl.
CPC .... *C07K 16/3023* (2013.01); *A61K 47/48484* (2013.01); *A61K 47/48561* (2013.01); *A61K 47/48569* (2013.01); *A61K 47/48592* (2013.01); *A61K 49/0058* (2013.01); *A61K 51/1054* (2013.01); *C07K 14/7051* (2013.01); *C07K 16/28* (2013.01); *C07K 16/30* (2013.01); *C07K 16/468* (2013.01); *G01N 33/574* (2013.01); *G01N 33/57492* (2013.01); *A61K 2039/505* (2013.01); *C07K 2317/24* (2013.01); *C07K 2317/31* (2013.01); *C07K 2317/34* (2013.01); *C07K 2317/54* (2013.01); *C07K 2317/55* (2013.01); *C07K 2317/56* (2013.01); *C07K 2317/565* (2013.01); *C07K 2317/622* (2013.01); *C07K 2317/624* (2013.01); *C07K 2317/76* (2013.01); *C07K 2317/92* (2013.01); *C07K 2319/30* (2013.01); *C07K 2319/55* (2013.01); *G01N 2333/705* (2013.01)

(58) Field of Classification Search
CPC ....... C07K 16/00–16/468; C07K 16/30; A61K 47/48484; A61K 47/48561; A61K 47/48569; G01N 33/57492
See application file for complete search history.

(56) References Cited

U.S. PATENT DOCUMENTS

| | | | |
|---|---|---|---|
| 8,268,970 B2 | 9/2012 | Terrett et al. | |
| 8,357,783 B2 | 1/2013 | Dimitrov et al. | |
| 8,460,660 B2 | 6/2013 | Ho et al. | |
| 9,084,829 B2 | 7/2015 | Kahnert et al. | |
| 9,409,992 B2 * | 8/2016 | Ho | A61K 47/48561 |

(Continued)

FOREIGN PATENT DOCUMENTS

| | | |
|---|---|---|
| WO | WO 2006/099141 | 9/2006 |
| WO | WO 2006/124641 | 11/2006 |
| WO | WO 2009/120769 | 10/2009 |

OTHER PUBLICATIONS

Chang et al., "Monoclonal Antibody K1 Reacts with Epithelial Mesothelioma but not with Lung Adenocarcinoma," *Am. J. Surg. Path.*, vol. 16:259-268, 1992.

(Continued)

*Primary Examiner* — Jessica H Roark
(74) *Attorney, Agent, or Firm* — Klarquist Sparkman, LLP

(57) ABSTRACT

Described herein is the use of rabbit hybridoma technology, along with a panel of truncated mesothelin domain fragments, to identify anti-mesothelin mAbs that bind specific regions of mesothelin. In one aspect of the present disclosure, the rabbit mAbs bind an epitope that is not part of Region I. In particular, the identified mAbs (YP187, YP223, YP218 and YP3) bind either Region II (391-486), Region III (487-581) or a native conformation of mesothelin with subnanomolar affinity. These antibodies do not compete for binding with the mesothelin-specific immunotoxin SS1P or mesothelin-specific antibody MORAb-009. In another aspect, disclosed is a high-affinity rabbit mAb that binds Region I of mesothelin (YP158). YP158 binds native mesothelin protein in cancer cells and tissues with high affinity and specificity.

28 Claims, 16 Drawing Sheets

(56) References Cited

U.S. PATENT DOCUMENTS

2011/0236385 A1  9/2011  Ho et al.
2015/0274836 A1  10/2015  Ho et al.

OTHER PUBLICATIONS

Hagiwara et al., "Establishment of a Novel Specific ELISA System for a Rat N- and C-ERC/Mesothelin. Rat ERC/Mesothelin Body Fluids of Mice Bearing Mesothelioma," *Cancer Sci.*, vol. 99:666-670, 2008.
Hassan et al., "Mesothelin: A New Target for Immunotherapy," *Clin. Cancer Res.*, vol. 10:3937-3942, 2004.
Hassan et al., "Mesothelin Targeted Cancer Immunotherapy," *Eur. J. Cancer*, vol. 44:46-53, 2008.
Kaneko et al., "A Binding Domain on Mesothelin for CA125/MUC16," *J. Biol. Chem.*, vol. 284:3739-3749, 2009.
Kelly et al., "Mesothelin-Targeted Agents in Clinical Trials and in Preclinical Development," *Mol. Cancer Ther.*, vol. 11:517-525, 2012.

* cited by examiner

SS1P/MORAb-009 binding
MUC16/CA125 binding

H9 MSLN (1:3 Serial

K5 MSLN (1:3 Serial

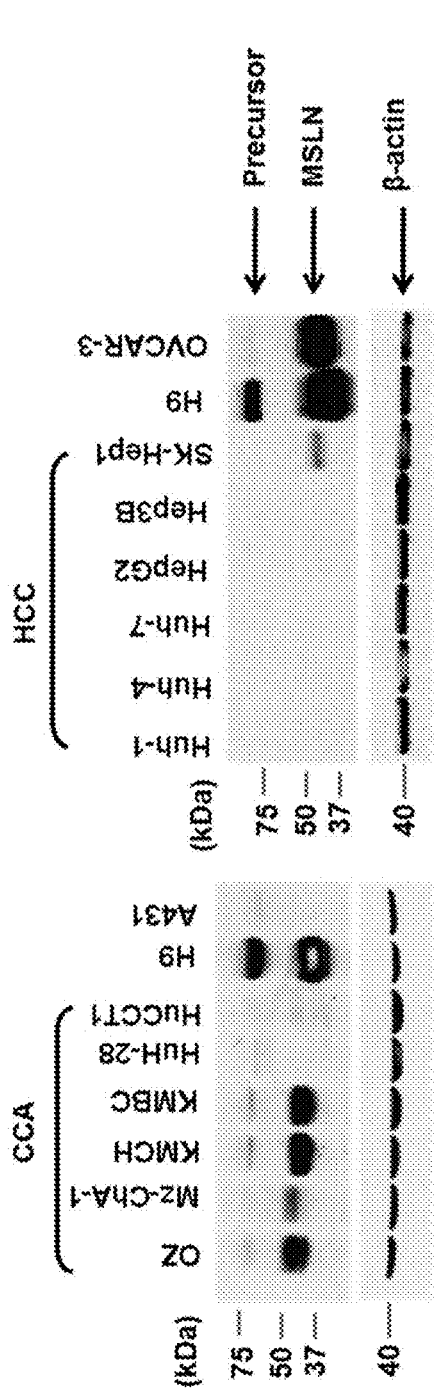
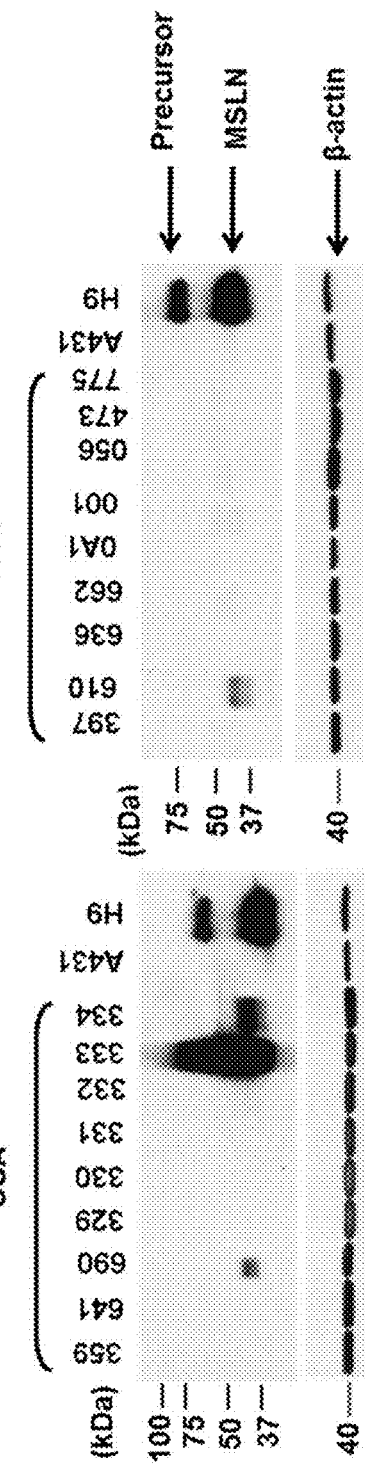
FIG. 8A
FIG. 8B

SEQUENCE LISTING

```
<160> NUMBER OF SEQ ID NOS: 39

<210> SEQ ID NO 1
<211> LENGTH: 613
<212> TYPE: PRT
<213> ORGANISM: Pseudomonas aeruginosa

<400> SEQUENCE: 1

Ala Glu Glu Ala Phe Asp Leu Trp Asn Glu Cys Ala Lys Ala Cys Val
1               5                   10                  15

Leu Asp Leu Lys Asp Gly Val Arg Ser Ser Arg Met Ser Val Asp Pro
            20                  25                  30

Ala Ile Ala Asp Thr Asn Gly Gln Gly Val Leu His Tyr Ser Met Val
        35                  40                  45

Leu Glu Gly Gly Asn Asp Ala Leu Lys Leu Ala Ile Asp Asn Ala Leu
    50                  55                  60

Ser Ile Thr Ser Asp Gly Leu Thr Ile Arg Leu Glu Gly Gly Val Glu
65                  70                  75                  80

Pro Asn Lys Pro Val Arg Tyr Ser Tyr Thr Arg Gln Ala Arg Gly Ser
                85                  90                  95

Trp Ser Leu Asn Trp Leu Val Pro Ile Gly His Glu Lys Pro Ser Asn
            100                 105                 110

Ile Lys Val Phe Ile His Glu Leu Asn Ala Gly Asn Gln Leu Ser His
        115                 120                 125

Met Ser Pro Ile Tyr Thr Ile Glu Met Gly Asp Glu Leu Leu Ala Lys
    130                 135                 140

Leu Ala Arg Asp Ala Thr Phe Phe Val Arg Ala His Glu Ser Asn Glu
145                 150                 155                 160

Met Gln Pro Thr Leu Ala Ile Ser His Ala Gly Val Ser Val Val Met
                165                 170                 175

Ala Gln Thr Gln Pro Arg Arg Glu Lys Arg Trp Ser Glu Trp Ala Ser
            180                 185                 190

Gly Lys Val Leu Cys Leu Leu Asp Pro Leu Asp Gly Val Tyr Asn Tyr
        195                 200                 205

Leu Ala Gln Gln Arg Cys Asn Leu Asp Asp Thr Trp Glu Gly Lys Ile
    210                 215                 220
```

Tyr Arg Val Leu Ala Gly Asn Pro Ala Lys His Asp Leu Asp Ile Lys
225                 230                 235                 240

Pro Thr Val Ile Ser His Arg Leu His Phe Pro Glu Gly Gly Ser Leu
            245                 250                 255

Ala Ala Leu Thr Ala His Gln Ala Cys His Leu Pro Leu Glu Thr Phe
        260                 265                 270

Thr Arg His Arg Gln Pro Arg Gly Trp Glu Gln Leu Glu Gln Cys Gly
    275                 280                 285

Tyr Pro Val Gln Arg Leu Val Ala Leu Tyr Leu Ala Ala Arg Leu Ser
290                 295                 300

Trp Asn Gln Val Asp Gln Val Ile Arg Asn Ala Leu Ala Ser Pro Gly
305                 310                 315                 320

Ser Gly Gly Asp Leu Gly Glu Ala Ile Arg Glu Gln Pro Glu Gln Ala
                325                 330                 335

Arg Leu Ala Leu Thr Leu Ala Ala Ala Glu Ser Glu Arg Phe Val Arg
            340                 345                 350

Gln Gly Thr Gly Asn Asp Glu Ala Gly Ala Ala Asn Ala Asp Val Val
        355                 360                 365

Ser Leu Thr Cys Pro Val Ala Ala Gly Glu Cys Ala Gly Pro Ala Asp
    370                 375                 380

Ser Gly Asp Ala Leu Leu Glu Arg Asn Tyr Pro Thr Gly Ala Glu Phe
385                 390                 395                 400

Leu Gly Asp Gly Gly Asp Val Ser Phe Ser Thr Arg Gly Thr Gln Asn
                405                 410                 415

Trp Thr Val Glu Arg Leu Leu Gln Ala His Arg Gln Leu Glu Glu Arg
            420                 425                 430

Gly Tyr Val Phe Val Gly Tyr His Gly Thr Phe Leu Glu Ala Ala Gln
        435                 440                 445

Ser Ile Val Phe Gly Gly Val Arg Ala Arg Ser Gln Asp Leu Asp Ala
    450                 455                 460

Ile Trp Arg Gly Phe Tyr Ile Ala Gly Asp Pro Ala Leu Ala Tyr Gly
465                 470                 475                 480

Tyr Ala Gln Asp Gln Glu Pro Asp Ala Arg Gly Arg Ile Arg Asn Gly
                485                 490                 495

Ala Leu Leu Arg Val Tyr Val Pro Arg Ser Ser Leu Pro Gly Phe Tyr
            500                 505                 510

Arg Thr Ser Leu Thr Leu Ala Ala Pro Glu Ala Ala Gly Glu Val Glu
        515                 520                 525

Arg Leu Ile Gly His Pro Leu Pro Leu Arg Leu Asp Ala Ile Thr Gly
    530                 535                 540

Pro Glu Glu Glu Gly Gly Arg Leu Glu Thr Ile Leu Gly Trp Pro Leu
545                 550                 555                 560

Ala Glu Arg Thr Val Val Ile Pro Ser Ala Ile Pro Thr Asp Pro Arg
                565                 570                 575

Asn Val Gly Gly Asp Leu Asp Pro Ser Ser Ile Pro Asp Lys Glu Gln
            580                 585                 590

Ala Ile Ser Ala Leu Pro Asp Tyr Ala Ser Gln Pro Gly Lys Pro Pro
        595                 600                 605

Arg Glu Asp Leu Lys
    610

<210> SEQ ID NO 2
<211> LENGTH: 347

```
<212> TYPE: PRT
<213> ORGANISM: Artificial Sequence
<220> FEATURE:
<223> OTHER INFORMATION: Synthetic polypeptide

<400> SEQUENCE: 2

Pro Glu Gly Gly Ser Leu Ala Ala Leu Thr Ala His Gln Ala Cys His
1               5                   10                  15

Leu Pro Leu Glu Thr Phe Thr Arg His Arg Gln Pro Arg Gly Trp Glu
            20                  25                  30

Gln Leu Glu Gln Cys Gly Tyr Pro Val Gln Arg Leu Val Ala Leu Tyr
        35                  40                  45

Leu Ala Ala Arg Leu Ser Trp Asn Gln Val Asp Gln Val Ile Arg Asn
    50                  55                  60

Ala Leu Ala Ser Pro Gly Ser Gly Gly Asp Leu Gly Glu Ala Ile Arg
65                  70                  75                  80

Glu Gln Pro Glu Gln Ala Arg Leu Ala Leu Thr Leu Ala Ala Ala Glu
                85                  90                  95

Ser Glu Arg Phe Val Arg Gln Gly Thr Gly Asn Asp Glu Ala Gly Ala
            100                 105                 110

Ala Asn Gly Pro Ala Asp Ser Gly Asp Ala Leu Leu Glu Arg Asn Tyr
        115                 120                 125

Pro Thr Gly Ala Glu Phe Leu Gly Asp Gly Gly Asp Val Ser Phe Ser
    130                 135                 140

Thr Arg Gly Thr Gln Asn Trp Thr Val Glu Arg Leu Leu Gln Ala His
145                 150                 155                 160

Arg Gln Leu Glu Glu Arg Gly Tyr Val Phe Val Gly Tyr His Gly Thr
                165                 170                 175

Phe Leu Glu Ala Ala Gln Ser Ile Val Phe Gly Gly Val Arg Ala Arg
            180                 185                 190

Ser Gln Asp Leu Asp Ala Ile Trp Arg Gly Phe Tyr Ile Ala Gly Asp
        195                 200                 205

Pro Ala Leu Ala Tyr Gly Tyr Ala Gln Asp Gln Glu Pro Asp Ala Arg
    210                 215                 220

Gly Arg Ile Arg Asn Gly Ala Leu Leu Arg Val Tyr Val Pro Arg Ser
225                 230                 235                 240

Ser Leu Pro Gly Phe Tyr Arg Thr Ser Leu Thr Leu Ala Ala Pro Glu
                245                 250                 255

Ala Ala Gly Glu Val Glu Arg Leu Ile Gly His Pro Leu Pro Leu Arg
            260                 265                 270

Leu Asp Ala Ile Thr Gly Pro Glu Glu Gly Gly Arg Leu Glu Thr
        275                 280                 285

Ile Leu Gly Trp Pro Leu Ala Glu Arg Thr Val Val Ile Pro Ser Ala
    290                 295                 300

Ile Pro Thr Asp Pro Arg Asn Val Gly Gly Asp Leu Asp Pro Ser Ser
305                 310                 315                 320

Ile Pro Asp Lys Glu Gln Ala Ile Ser Ala Leu Pro Asp Tyr Ala Ser
                325                 330                 335

Gln Pro Gly Lys Pro Pro Arg Glu Asp Leu Lys
            340                 345

<210> SEQ ID NO 3
<211> LENGTH: 230
<212> TYPE: PRT
<213> ORGANISM: Artificial Sequence
<220> FEATURE:
```

<223> OTHER INFORMATION: Synthetic polypeptide

<400> SEQUENCE: 3

```
Arg His Arg Gln Pro Arg Gly Trp Glu Gln Leu Pro Thr Gly Ala Glu
1               5                   10                  15

Phe Leu Gly Asp Gly Gly Asp Val Ser Phe Ser Thr Arg Gly Thr Gln
            20                  25                  30

Asn Trp Thr Val Glu Arg Leu Leu Gln Ala His Arg Gln Leu Glu Glu
        35                  40                  45

Arg Gly Tyr Val Phe Val Gly Tyr His Gly Thr Phe Leu Glu Ala Ala
    50                  55                  60

Gln Ser Ile Val Phe Gly Gly Val Arg Ala Arg Ser Gln Asp Leu Asp
65                  70                  75                  80

Ala Ile Trp Arg Gly Phe Tyr Ile Ala Gly Asp Pro Ala Leu Ala Tyr
                85                  90                  95

Gly Tyr Ala Gln Asp Gln Glu Pro Asp Ala Arg Gly Arg Ile Arg Asn
            100                 105                 110

Gly Ala Leu Leu Arg Val Tyr Val Pro Arg Ser Ser Leu Pro Gly Phe
        115                 120                 125

Tyr Arg Thr Ser Leu Thr Leu Ala Ala Pro Glu Ala Ala Gly Glu Val
    130                 135                 140

Glu Arg Leu Ile Gly His Pro Leu Pro Leu Arg Leu Asp Ala Ile Thr
145                 150                 155                 160

Gly Pro Glu Glu Glu Gly Arg Leu Glu Thr Ile Leu Gly Trp Pro
                165                 170                 175

Leu Ala Glu Arg Thr Val Val Ile Pro Ser Ala Ile Pro Thr Asp Pro
                180                 185                 190

Arg Asn Val Gly Gly Asp Leu Asp Pro Ser Ser Ile Pro Asp Lys Glu
            195                 200                 205

Gln Ala Ile Ser Ala Leu Pro Asp Tyr Ala Ser Gln Pro Gly Lys Pro
        210                 215                 220

Pro Arg Glu Asp Leu Lys
225                 230
```

<210> SEQ ID NO 4
<211> LENGTH: 230
<212> TYPE: PRT
<213> ORGANISM: Artificial Sequence
<220> FEATURE:
<223> OTHER INFORMATION: Synthetic polypeptide

<400> SEQUENCE: 4

```
Arg His Arg Gln Pro Arg Gly Trp Glu Gln Leu Pro Thr Gly Ala Glu
1               5                   10                  15

Phe Leu Gly Asp Gly Gly Asp Val Ser Phe Ser Thr Arg Gly Thr Gln
            20                  25                  30

Asn Trp Thr Val Glu Arg Leu Leu Gln Ala His Arg Gln Leu Glu Glu
        35                  40                  45

Gly Gly Tyr Val Phe Val Gly Tyr His Gly Thr Phe Leu Glu Ala Ala
    50                  55                  60

Gln Ser Ile Val Phe Gly Gly Val Arg Ala Arg Ser Gln Asp Leu Asp
65                  70                  75                  80

Ala Ile Trp Ala Gly Phe Tyr Ile Ala Gly Asp Pro Ala Leu Ala Tyr
                85                  90                  95

Gly Tyr Ala Gln Asp Gln Glu Pro Asp Ala Ala Gly Arg Ile Arg Asn
            100                 105                 110
```

Gly Ala Leu Leu Arg Val Tyr Val Pro Arg Ser Ser Leu Pro Gly Phe
            115                 120                 125

Tyr Ala Thr Ser Leu Thr Leu Ala Ala Pro Glu Ala Gly Glu Val
        130                 135                 140

Glu Arg Leu Ile Gly His Pro Leu Pro Leu Arg Leu Asp Ala Ile Thr
145                 150                 155                 160

Gly Pro Glu Glu Ser Gly Gly Arg Leu Glu Thr Ile Leu Gly Trp Pro
                165                 170                 175

Leu Ala Glu Arg Thr Val Val Ile Pro Ser Ala Ile Pro Thr Asp Pro
            180                 185                 190

Arg Asn Val Gly Gly Asp Leu Asp Pro Ser Ser Ile Pro Asp Ser Glu
            195                 200                 205

Gln Ala Ile Ser Ala Leu Pro Asp Tyr Ala Ser Gln Pro Gly Lys Pro
            210                 215                 220

Pro Arg Glu Asp Leu Lys
225             230

```
<210> SEQ ID NO 5
<211> LENGTH: 230
<212> TYPE: PRT
<213> ORGANISM: Artificial Sequence
<220> FEATURE:
<223> OTHER INFORMATION: Synthetic polypeptide
<220> FEATURE:
<221> NAME/KEY: MISC_FEATURE
<222> LOCATION: (23)..(23)
<223> OTHER INFORMATION: X = Gly, Ala or Ser
<220> FEATURE:
<221> NAME/KEY: MISC_FEATURE
<222> LOCATION: (49)..(49)
<223> OTHER INFORMATION: X = Gly, Ala or Ser
<220> FEATURE:
<221> NAME/KEY: MISC_FEATURE
<222> LOCATION: (84)..(84)
<223> OTHER INFORMATION: X = Gly, Ala or Ser
<220> FEATURE:
<221> NAME/KEY: MISC_FEATURE
<222> LOCATION: (107)..(107)
<223> OTHER INFORMATION: X = Gly, Ala or Ser
<220> FEATURE:
<221> NAME/KEY: MISC_FEATURE
<222> LOCATION: (130)..(130)
<223> OTHER INFORMATION: X = Gly, Ala or Ser
<220> FEATURE:
<221> NAME/KEY: MISC_FEATURE
<222> LOCATION: (165)..(165)
<223> OTHER INFORMATION: X = Gly, Ala or Ser
<220> FEATURE:
<221> NAME/KEY: MISC_FEATURE
<222> LOCATION: (207)..(207)
<223> OTHER INFORMATION: X = Gly, Ala or Ser
<220> FEATURE:
<221> NAME/KEY: MISC_FEATURE
<222> LOCATION: (209)..(209)
<223> OTHER INFORMATION: X = Gly, Ala or Ser
```

<400> SEQUENCE: 5

Arg His Arg Gln Pro Arg Gly Trp Glu Gln Leu Pro Thr Gly Ala Glu
1               5                   10                  15

Phe Leu Gly Asp Gly Gly Xaa Val Ser Phe Ser Thr Arg Gly Thr Gln
            20                  25                  30

Asn Trp Thr Val Glu Arg Leu Leu Gln Ala His Arg Gln Leu Glu Glu
        35                  40                  45

Xaa Gly Tyr Val Phe Val Gly Tyr His Gly Thr Phe Leu Glu Ala Ala
    50                  55                  60

```
Gln Ser Ile Val Phe Gly Gly Val Arg Ala Arg Ser Gln Asp Leu Asp
 65                  70                  75                  80

Ala Ile Trp Xaa Gly Phe Tyr Ile Ala Gly Asp Pro Ala Leu Ala Tyr
                 85                  90                  95

Gly Tyr Ala Gln Asp Gln Glu Pro Asp Ala Xaa Gly Arg Ile Arg Asn
            100                 105                 110

Gly Ala Leu Leu Arg Val Tyr Val Pro Arg Ser Ser Leu Pro Gly Phe
            115                 120                 125

Tyr Xaa Thr Ser Leu Thr Leu Ala Ala Pro Glu Ala Gly Glu Val
            130                 135                 140

Glu Arg Leu Ile Gly His Pro Leu Pro Leu Arg Leu Asp Ala Ile Thr
145                 150                 155                 160

Gly Pro Glu Glu Xaa Gly Gly Arg Leu Glu Thr Ile Leu Gly Trp Pro
                165                 170                 175

Leu Ala Glu Arg Thr Val Val Ile Pro Ser Ala Ile Pro Thr Asp Pro
            180                 185                 190

Arg Asn Val Gly Gly Asp Leu Asp Pro Ser Ser Ile Pro Asp Xaa Glu
            195                 200                 205

Xaa Ala Ile Ser Ala Leu Pro Asp Tyr Ala Ser Gln Pro Gly Lys Pro
    210                 215                 220

Pro Arg Glu Asp Leu Lys
225                 230

<210> SEQ ID NO 6
<211> LENGTH: 230
<212> TYPE: PRT
<213> ORGANISM: Artificial Sequence
<220> FEATURE:
<223> OTHER INFORMATION: Synthetic polypeptide

<400> SEQUENCE: 6

Arg His Arg Gln Pro Arg Gly Trp Glu Gln Leu Pro Thr Gly Ala Glu
  1               5                  10                  15

Phe Leu Gly Asp Gly Gly Ala Val Ser Phe Ser Thr Arg Gly Thr Gln
                 20                  25                  30

Asn Trp Thr Val Glu Arg Leu Leu Gln Ala His Arg Gln Leu Glu Glu
             35                  40                  45

Gly Gly Tyr Val Phe Val Gly Tyr His Gly Thr Phe Leu Glu Ala Ala
         50                  55                  60

Gln Ser Ile Val Phe Gly Gly Val Arg Ala Arg Ser Gln Asp Leu Asp
 65                  70                  75                  80

Ala Ile Trp Ala Gly Phe Tyr Ile Ala Gly Asp Pro Ala Leu Ala Tyr
                 85                  90                  95

Gly Tyr Ala Gln Asp Gln Glu Pro Asp Ala Ala Gly Arg Ile Arg Asn
            100                 105                 110

Gly Ala Leu Leu Arg Val Tyr Val Pro Arg Ser Ser Leu Pro Gly Phe
            115                 120                 125

Tyr Ala Thr Ser Leu Thr Leu Ala Ala Pro Glu Ala Ala Gly Glu Val
            130                 135                 140

Glu Arg Leu Ile Gly His Pro Leu Pro Leu Arg Leu Asp Ala Ile Thr
145                 150                 155                 160

Gly Pro Glu Glu Ser Gly Gly Arg Leu Glu Thr Ile Leu Gly Trp Pro
                165                 170                 175

Leu Ala Glu Arg Thr Val Val Ile Pro Ser Ala Ile Pro Thr Asp Pro
            180                 185                 190
```

-continued

```
Arg Asn Val Gly Gly Asp Leu Asp Pro Ser Ser Ile Pro Asp Ser Glu
            195                 200                 205

Ala Ala Ile Ser Ala Leu Pro Asp Tyr Ala Ser Gln Pro Gly Lys Pro
210                 215                 220

Pro Arg Glu Asp Leu Lys
225                 230

<210> SEQ ID NO 7
<211> LENGTH: 630
<212> TYPE: PRT
<213> ORGANISM: Homo sapiens

<400> SEQUENCE: 7

Met Ala Leu Pro Thr Ala Arg Pro Leu Leu Gly Ser Cys Gly Thr Pro
1               5                   10                  15

Ala Leu Gly Ser Leu Leu Phe Leu Leu Phe Ser Leu Gly Trp Val Gln
            20                  25                  30

Pro Ser Arg Thr Leu Ala Gly Glu Thr Gly Gln Glu Ala Ala Pro Leu
        35                  40                  45

Asp Gly Val Leu Ala Asn Pro Pro Asn Ile Ser Ser Leu Ser Pro Arg
    50                  55                  60

Gln Leu Leu Gly Phe Pro Cys Ala Glu Val Ser Gly Leu Ser Thr Glu
65                  70                  75                  80

Arg Val Arg Glu Leu Ala Val Ala Leu Ala Gln Lys Asn Val Lys Leu
                85                  90                  95

Ser Thr Glu Gln Leu Arg Cys Leu Ala His Arg Leu Ser Glu Pro Pro
            100                 105                 110

Glu Asp Leu Asp Ala Leu Pro Leu Asp Leu Leu Leu Phe Leu Asn Pro
        115                 120                 125

Asp Ala Phe Ser Gly Pro Gln Ala Cys Thr Arg Phe Phe Ser Arg Ile
    130                 135                 140

Thr Lys Ala Asn Val Asp Leu Leu Pro Arg Gly Ala Pro Glu Arg Gln
145                 150                 155                 160

Arg Leu Leu Pro Ala Ala Leu Ala Cys Trp Gly Val Arg Gly Ser Leu
                165                 170                 175

Leu Ser Glu Ala Asp Val Arg Ala Leu Gly Gly Leu Ala Cys Asp Leu
            180                 185                 190

Pro Gly Arg Phe Val Ala Glu Ser Ala Glu Val Leu Leu Pro Arg Leu
        195                 200                 205

Val Ser Cys Pro Gly Pro Leu Asp Gln Asp Gln Gln Glu Ala Ala Arg
    210                 215                 220

Ala Ala Leu Gln Gly Gly Gly Pro Pro Tyr Gly Pro Pro Ser Thr Trp
225                 230                 235                 240

Ser Val Ser Thr Met Asp Ala Leu Arg Gly Leu Leu Pro Val Leu Gly
                245                 250                 255

Gln Pro Ile Ile Arg Ser Ile Pro Gln Gly Ile Val Ala Ala Trp Arg
            260                 265                 270

Gln Arg Ser Ser Arg Asp Pro Ser Trp Arg Gln Pro Glu Arg Thr Ile
        275                 280                 285

Leu Arg Pro Arg Phe Arg Arg Glu Val Glu Lys Thr Ala Cys Pro Ser
    290                 295                 300

Gly Lys Lys Ala Arg Glu Ile Asp Glu Ser Leu Ile Phe Tyr Lys Lys
305                 310                 315                 320

Trp Glu Leu Glu Ala Cys Val Asp Ala Ala Leu Leu Ala Thr Gln Met
                325                 330                 335
```

Asp Arg Val Asn Ala Ile Pro Phe Thr Tyr Glu Gln Leu Asp Val Leu
                340                 345                 350

Lys His Lys Leu Asp Glu Leu Tyr Pro Gln Gly Tyr Pro Glu Ser Val
                355                 360                 365

Ile Gln His Leu Gly Tyr Leu Phe Leu Lys Met Ser Pro Glu Asp Ile
                370                 375                 380

Arg Lys Trp Asn Val Thr Ser Leu Glu Thr Leu Lys Ala Leu Leu Glu
385                 390                 395                 400

Val Asn Lys Gly His Glu Met Ser Pro Gln Ala Pro Arg Arg Pro Leu
                405                 410                 415

Pro Gln Val Ala Thr Leu Ile Asp Arg Phe Val Lys Gly Arg Gly Gln
                420                 425                 430

Leu Asp Lys Asp Thr Leu Asp Thr Leu Thr Ala Phe Tyr Pro Gly Tyr
                435                 440                 445

Leu Cys Ser Leu Ser Pro Glu Glu Leu Ser Ser Val Pro Pro Ser Ser
                450                 455                 460

Ile Trp Ala Val Arg Pro Gln Asp Leu Asp Thr Cys Asp Pro Arg Gln
465                 470                 475                 480

Leu Asp Val Leu Tyr Pro Lys Ala Arg Leu Ala Phe Gln Asn Met Asn
                485                 490                 495

Gly Ser Glu Tyr Phe Val Lys Ile Gln Ser Phe Leu Gly Gly Ala Pro
                500                 505                 510

Thr Glu Asp Leu Lys Ala Leu Ser Gln Gln Asn Val Ser Met Asp Leu
                515                 520                 525

Ala Thr Phe Met Lys Leu Arg Thr Asp Ala Val Leu Pro Leu Thr Val
                530                 535                 540

Ala Glu Val Gln Lys Leu Leu Gly Pro His Val Glu Gly Leu Lys Ala
545                 550                 555                 560

Glu Glu Arg His Arg Pro Val Arg Asp Trp Ile Leu Arg Gln Arg Gln
                565                 570                 575

Asp Asp Leu Asp Thr Leu Gly Leu Gly Leu Gln Gly Gly Ile Pro Asn
                580                 585                 590

Gly Tyr Leu Val Leu Asp Leu Ser Met Gln Glu Ala Leu Ser Gly Thr
                595                 600                 605

Pro Cys Leu Leu Gly Pro Gly Pro Val Leu Thr Val Leu Ala Leu Leu
                610                 615                 620

Leu Ala Ser Thr Leu Ala
625                 630

<210> SEQ ID NO 8
<211> LENGTH: 366
<212> TYPE: DNA
<213> ORGANISM: Artificial Sequence
<220> FEATURE:
<223> OTHER INFORMATION: Synthetic polynucleotide

<400> SEQUENCE: 8
caggagcagc tggaggagtc cggggagac ctggtccagc ctgagggatc cctgacactc      60
acctgcaaag cctctgggtt agacttcagt agcagctact ggatatgttg ggtccgccag    120
gctccaggga aggggctgga gtggatcggg tgtcgtcata cttttactgc taacacatgg    180
tccgcgagct gggtgaatgg ccggttcacc atctccagaa gcaccagcct aggcacggtg    240
gatctgaaaa tgaccagtct gacagccgcg gacacggcca cctatttctg tgccagagat    300
gaatctaata atgatggttg ggattttaag ttgtggggcc caggcaccct ggtcaccgtc    360
tcctca 366

<210> SEQ ID NO 9
<211> LENGTH: 122
<212> TYPE: PRT
<213> ORGANISM: Artificial Sequence
<220> FEATURE:
<223> OTHER INFORMATION: Synthetic polypeptide

<400> SEQUENCE: 9

Gln Glu Gln Leu Glu Glu Ser Gly Gly Asp Leu Val Gln Pro Glu Gly
1               5                   10                  15

Ser Leu Thr Leu Thr Cys Lys Ala Ser Gly Leu Asp Phe Ser Ser Ser
            20                  25                  30

Tyr Trp Ile Cys Trp Val Arg Gln Ala Pro Gly Lys Gly Leu Glu Trp
        35                  40                  45

Ile Gly Cys Arg His Thr Phe Thr Ala Asn Thr Trp Ser Ala Ser Trp
    50                  55                  60

Val Asn Gly Arg Phe Thr Ile Ser Arg Ser Thr Ser Leu Gly Thr Val
65                  70                  75                  80

Asp Leu Lys Met Thr Ser Leu Thr Ala Ala Asp Thr Ala Thr Tyr Phe
                85                  90                  95

Cys Ala Arg Asp Glu Ser Asn Asn Asp Gly Trp Asp Phe Lys Leu Trp
            100                 105                 110

Gly Pro Gly Thr Leu Val Thr Val Ser Ser
        115                 120

<210> SEQ ID NO 10
<211> LENGTH: 327
<212> TYPE: DNA
<213> ORGANISM: Artificial Sequence
<220> FEATURE:
<223> OTHER INFORMATION: Synthetic polynucleotide

<400> SEQUENCE: 10
gcctatgata tgacccagac tccagcctcc gtgtctgcag ctgtgggagg cacagtcacc        60
atcaagtgcc aggccagtca gagcattagt aactacttag cctggtatca gcagaaacca       120
gggcagcctc ccaagctcct gatctaccag gcatccactc tggcacctgg ggtctcatcg       180
cggttcaaag gcagtggatc tgggacagaa ttcactctca ccatcagcgg cgtggagtgt       240
gccgatgctg ccacttacta ctgtcaacag ggttatacta gtagtaatgt tgagaatgtt       300
ttcggcggag ggaccggggt ggtggtc                                           327

<210> SEQ ID NO 11
<211> LENGTH: 109
<212> TYPE: PRT
<213> ORGANISM: Artificial Sequence
<220> FEATURE:
<223> OTHER INFORMATION: Synthetic polypeptide

<400> SEQUENCE: 11

Ala Tyr Asp Met Thr Gln Thr Pro Ala Ser Val Ser Ala Ala Val Gly
1               5                   10                  15

Gly Thr Val Thr Ile Lys Cys Gln Ala Ser Gln Ser Ile Ser Asn Tyr
            20                  25                  30

Leu Ala Trp Tyr Gln Gln Lys Pro Gly Gln Pro Pro Lys Leu Leu Ile
        35                  40                  45

Tyr Gln Ala Ser Thr Leu Ala Pro Gly Val Ser Ser Arg Phe Lys Gly

```
                    50                  55                  60
Ser Gly Ser Gly Thr Glu Phe Thr Leu Thr Ile Ser Gly Val Glu Cys
 65                  70                  75                  80

Ala Asp Ala Ala Thr Tyr Tyr Cys Gln Gln Gly Tyr Thr Ser Ser Asn
                 85                  90                  95

Val Glu Asn Val Phe Gly Gly Gly Thr Gly Val Val Val
            100                 105
```

<210> SEQ ID NO 12
<211> LENGTH: 369
<212> TYPE: DNA
<213> ORGANISM: Artificial Sequence
<220> FEATURE:
<223> OTHER INFORMATION: Synthetic polynucleotide

<400> SEQUENCE: 12

```
cagcagcagc tggaggagtc cggggaggc ctggtcaagc ctgagggatc cctgacactc      60
acctgcaaag cctctggatt cgacctcggt ttctactttt acgcctgttg ggtccgccag     120
gctccaggga agggcctgga gtggatcgca tgcatttata ctgctggtag tggtagcacg     180
tactacgcga gctgggcgaa aggccgattc accatctcca aagcctcgtc gaccacggtg     240
actctgcaaa tgaccagtct ggcagccgcg gacacggcca cctatttctg tgcgagatct     300
actgctaata ctagaagtac ttattatctt aacttgtggg gcccaggcac cctggtcacc     360
gtctcctca                                                            369
```

<210> SEQ ID NO 13
<211> LENGTH: 123
<212> TYPE: PRT
<213> ORGANISM: Artificial Sequence
<220> FEATURE:
<223> OTHER INFORMATION: Synthetic polypeptide

<400> SEQUENCE: 13

```
Gln Gln Gln Leu Glu Glu Ser Gly Gly Gly Leu Val Lys Pro Glu Gly
 1               5                  10                  15

Ser Leu Thr Leu Thr Cys Lys Ala Ser Gly Phe Asp Leu Gly Phe Tyr
             20                  25                  30

Phe Tyr Ala Cys Trp Val Arg Gln Ala Pro Gly Lys Gly Leu Glu Trp
         35                  40                  45

Ile Ala Cys Ile Tyr Thr Ala Gly Ser Gly Ser Thr Tyr Tyr Ala Ser
 50                  55                  60

Trp Ala Lys Gly Arg Phe Thr Ile Ser Lys Ala Ser Ser Thr Thr Val
 65                  70                  75                  80

Thr Leu Gln Met Thr Ser Leu Ala Ala Ala Asp Thr Ala Thr Tyr Phe
                 85                  90                  95

Cys Ala Arg Ser Thr Ala Asn Thr Arg Ser Thr Tyr Tyr Leu Asn Leu
            100                 105                 110

Trp Gly Pro Gly Thr Leu Val Thr Val Ser Ser
        115                 120
```

<210> SEQ ID NO 14
<211> LENGTH: 330
<212> TYPE: DNA
<213> ORGANISM: Artificial Sequence
<220> FEATURE:
<223> OTHER INFORMATION: Synthetic polynucleotide

<400> SEQUENCE: 14

```
gacgtcgtga tgacccagac tccagcctcc gtgtctgaac ctgtgggagg cacagtcacc      60
atcaagtgcc aggccagtca gaggattagt agttacttat cctggtatca gcagaaacca     120
gggcagcgtc ccaagctcct gatctttggt gcatccactc tggcatctgg ggtcccctcg     180
cggttcaaag gcagtggatc tgggacagaa tacactctca ccatcagcga cctggagtgt     240
gccgatgctg ccacttacta ctgtcagagt tatgcttatt ttgatagtaa taattggcat     300
gctttcggcg agggaccga ggtggtggtc                                        330
```

<210> SEQ ID NO 15
<211> LENGTH: 110
<212> TYPE: PRT
<213> ORGANISM: Artificial Sequence
<220> FEATURE:
<223> OTHER INFORMATION: Synthetic polypeptide

<400> SEQUENCE: 15

Asp Val Val Met Thr Gln Thr Pro Ala Ser Val Ser Glu Pro Val Gly
1               5                   10                  15

Gly Thr Val Thr Ile Lys Cys Gln Ala Ser Gln Arg Ile Ser Ser Tyr
            20                  25                  30

Leu Ser Trp Tyr Gln Gln Lys Pro Gly Gln Arg Pro Lys Leu Leu Ile
        35                  40                  45

Phe Gly Ala Ser Thr Leu Ala Ser Gly Val Pro Ser Arg Phe Lys Gly
    50                  55                  60

Ser Gly Ser Gly Thr Glu Tyr Thr Leu Thr Ile Ser Asp Leu Glu Cys
65                  70                  75                  80

Ala Asp Ala Ala Thr Tyr Tyr Cys Gln Ser Tyr Ala Tyr Phe Asp Ser
                85                  90                  95

Asn Asn Trp His Ala Phe Gly Gly Gly Thr Glu Val Val Val
            100                 105                 110

<210> SEQ ID NO 16
<211> LENGTH: 357
<212> TYPE: DNA
<213> ORGANISM: Artificial Sequence
<220> FEATURE:
<223> OTHER INFORMATION: Synthetic polynucleotide

<400> SEQUENCE: 16

```
caggagcagc tggtggagtc cggggggaggc ctggtccagc ctggggcatc cctgacactc      60
acctgcacag cctctggaat cgacttcagt cgctactaca tgtgttgggt ccgccaggct     120
ccagggaagg gactggaggg gatcgcatgt atttatattg gtggtagtgg tagcacttac     180
tacgcgagct gggcgaaagg ccgattcacc atctccaaag cctcgtcgac acggtgact      240 ctgcaaatga ccagtctgac agccgcggac acggccactt atttctgtgc agagggggact     300 aatcttaatt atattttag gttgtggggc ccaggcaccc tggtcaccgt ctcctca         357
```

<210> SEQ ID NO 17
<211> LENGTH: 119
<212> TYPE: PRT
<213> ORGANISM: Artificial Sequence
<220> FEATURE:
<223> OTHER INFORMATION: Synthetic polypeptide

<400> SEQUENCE: 17

Gln Glu Gln Leu Val Glu Ser Gly Gly Gly Leu Val Gln Pro Gly Ala
1               5                   10                  15

Ser Leu Thr Leu Thr Cys Thr Ala Ser Gly Ile Asp Phe Ser Arg Tyr

```
                    20                  25                  30
Tyr Met Cys Trp Val Arg Gln Ala Pro Gly Lys Gly Leu Glu Gly Ile
        35                  40                  45

Ala Cys Ile Tyr Ile Gly Gly Ser Gly Ser Thr Tyr Tyr Ala Ser Trp
    50                  55                  60

Ala Lys Gly Arg Phe Thr Ile Ser Lys Ala Ser Ser Thr Thr Val Thr
65                  70                  75                  80

Leu Gln Met Thr Ser Leu Thr Ala Ala Asp Thr Ala Thr Tyr Phe Cys
                85                  90                  95

Ala Arg Gly Thr Asn Leu Asn Tyr Ile Phe Arg Leu Trp Gly Pro Gly
            100                 105                 110

Thr Leu Val Thr Val Ser Ser
        115

<210> SEQ ID NO 18
<211> LENGTH: 327
<212> TYPE: DNA
<213> ORGANISM: Artificial Sequence
<220> FEATURE:
<223> OTHER INFORMATION: Synthetic polynucleotide

<400> SEQUENCE: 18
gatgttgtga tgacccagac tccatctccc gtgtctgcag ctgtgggagg cacagtcacc      60
atcaagtgcc aggccagtca gagcattaat aatggtttag cctggtatca gcagaaacca    120
gggcagcctc ccaggctcct gatctattct gcatccaatc tggaatctgg ggtcccatcg    180
cggttcaaag gcagtggatc tgggacagag ttcactctca ccatcagcga cctggagtgt    240
gacgatgctg ccacttacta ttgtcaatgt atttgggatg gtaatagtta tgttaatgct    300
ttcggcggag ggaccgaggt ggtggtc                                        327

<210> SEQ ID NO 19
<211> LENGTH: 109
<212> TYPE: PRT
<213> ORGANISM: Artificial Sequence
<220> FEATURE:
<223> OTHER INFORMATION: Synthetic polypeptide

<400> SEQUENCE: 19

Asp Val Val Met Thr Gln Thr Pro Ser Pro Val Ser Ala Ala Val Gly
1               5                   10                  15

Gly Thr Val Thr Ile Lys Cys Gln Ala Ser Gln Ser Ile Asn Asn Gly
            20                  25                  30

Leu Ala Trp Tyr Gln Gln Lys Pro Gly Gln Pro Pro Arg Leu Leu Ile
        35                  40                  45

Tyr Ser Ala Ser Asn Leu Glu Ser Gly Val Pro Ser Arg Phe Lys Gly
    50                  55                  60

Ser Gly Ser Gly Thr Glu Phe Thr Leu Thr Ile Ser Asp Leu Glu Cys
65                  70                  75                  80

Asp Asp Ala Ala Thr Tyr Tyr Cys Gln Cys Ile Trp Asp Gly Asn Ser
                85                  90                  95

Tyr Val Asn Ala Phe Gly Gly Gly Thr Glu Val Val Val
            100                 105

<210> SEQ ID NO 20
<211> LENGTH: 345
<212> TYPE: DNA
<213> ORGANISM: Artificial Sequence
<220> FEATURE:
```

<223> OTHER INFORMATION: Synthetic polynucleotide

<400> SEQUENCE: 20

```
cagtcgttgg aggagtccgg gggagacctg gtcaagcctg ggcatccct gacactcacc      60
tgcaaagcct ctggattcga cttcagtagc aatgcaatgt gctgggtccg ccaggctcca    120
gggaagggc tggagtggat cgcatgcatt tatgttggtg atggcaacac atactacgcg     180
agctgggcga aaggccgatt taccatctcc aaaacctcgt cgaccacggt gactctgcaa    240
atgaccagtc tgacagccgc ggacacggcc acctatttct gtgcgagggg atatgctagt    300
tatggtagtg attattattg ggactacttt aagttgtggg ccca                      345
```

<210> SEQ ID NO 21
<211> LENGTH: 115
<212> TYPE: PRT
<213> ORGANISM: Artificial Sequence
<220> FEATURE:
<223> OTHER INFORMATION: Synthetic polypeptide

<400> SEQUENCE: 21

```
Gln Ser Leu Glu Glu Ser Gly Gly Asp Leu Val Lys Pro Gly Ala Ser
1               5                   10                  15
Leu Thr Leu Thr Cys Lys Ala Ser Gly Phe Asp Phe Ser Ser Asn Ala
            20                  25                  30
Met Cys Trp Val Arg Gln Ala Pro Gly Lys Gly Leu Glu Trp Ile Ala
        35                  40                  45
Cys Ile Tyr Val Gly Asp Gly Asn Thr Tyr Tyr Ala Ser Trp Ala Lys
    50                  55                  60
Gly Arg Phe Thr Ile Ser Lys Thr Ser Ser Thr Val Thr Leu Gln
65                  70                  75                  80
Met Thr Ser Leu Thr Ala Ala Asp Thr Ala Thr Tyr Phe Cys Ala Arg
            85                  90                  95
Gly Tyr Ala Ser Tyr Gly Ser Asp Tyr Tyr Trp Asp Tyr Phe Lys Leu
            100                 105                 110
Trp Gly Pro
        115
```

<210> SEQ ID NO 22
<211> LENGTH: 327
<212> TYPE: DNA
<213> ORGANISM: Artificial Sequence
<220> FEATURE:
<223> OTHER INFORMATION: Synthetic polynucleotide

<400> SEQUENCE: 22

```
gcctatgata tgacccagac tccagcctcc gtgtctgcag ctgtgggagg cacagtcacc      60
atcaagtgcc aggccagtca gagcattagc actgcattag cctggtatca gcagaaacca    120
gggcagcctc ccaaggtcct gatctatgct gcatccaatc tggcatctgg ggtctcatcg    180
cggttcaaag gcagtggatc tgggacagag ttcactctca ccatcagcga cctggagtgt    240
gccgatgctg ccacttacta ttgtcaacag gctgctacca ttattaatgt tgataatgtt    300
ttcggcggag ggaccgaggt ggtggtc                                         327
```

<210> SEQ ID NO 23
<211> LENGTH: 109
<212> TYPE: PRT
<213> ORGANISM: Artificial Sequence
<220> FEATURE:
<223> OTHER INFORMATION: Synthetic polypeptide

<400> SEQUENCE: 23

Ala Tyr Asp Met Thr Gln Thr Pro Ala Ser Val Ser Ala Val Gly
1               5                   10                  15

Gly Thr Val Thr Ile Lys Cys Gln Ala Ser Gln Ser Ile Ser Thr Ala
            20                  25                  30

Leu Ala Trp Tyr Gln Gln Lys Pro Gly Gln Pro Pro Lys Val Leu Ile
            35                  40                  45

Tyr Ala Ala Ser Asn Leu Ala Ser Gly Val Ser Ser Arg Phe Lys Gly
    50                  55                  60

Ser Gly Ser Gly Thr Glu Phe Thr Leu Thr Ile Ser Asp Leu Glu Cys
65                  70                  75                  80

Ala Asp Ala Ala Thr Tyr Tyr Cys Gln Gln Ala Ala Thr Ile Ile Asn
                85                  90                  95

Val Asp Asn Val Phe Gly Gly Gly Thr Glu Val Val Val
                100                 105

<210> SEQ ID NO 24
<211> LENGTH: 360
<212> TYPE: DNA
<213> ORGANISM: Artificial Sequence
<220> FEATURE:
<223> OTHER INFORMATION: Synthetic polynucleotide

<400> SEQUENCE: 24
cagtcgttgg aggagtccgg gggagacctg gtcaagcctg ggcatccct gacactcacc      60 tgcacagcct ctggattctc cttcagtggc gactactaca tgtgctgggt ccgccaggct    120
ccagggaagg gctggagtg gatcgcatgc attggtggtg gtagtaatac tgccacctac     180
tacgcgacct gggcgaaagg ccgattcacc atctccaaaa cctcgtcgac cacggtgact    240
ctgcaaatga ccagtctgac agccgcggac acggccacct atttctgtgc gagagatctc    300
ggttttgttg attatgcttt ggaattgtgg ggcccaggca ccctggtcac cgtctcctca    360

<210> SEQ ID NO 25
<211> LENGTH: 120
<212> TYPE: PRT
<213> ORGANISM: Artificial Sequence
<220> FEATURE:
<223> OTHER INFORMATION: Synthetic polypeptide

<400> SEQUENCE: 25

Gln Ser Leu Glu Glu Ser Gly Gly Asp Leu Val Lys Pro Gly Ala Ser
1               5                   10                  15

Leu Thr Leu Thr Cys Thr Ala Ser Gly Phe Ser Phe Ser Gly Asp Tyr
            20                  25                  30

Tyr Met Cys Trp Val Arg Gln Ala Pro Gly Lys Gly Leu Glu Trp Ile
            35                  40                  45

Ala Cys Ile Gly Gly Gly Ser Asn Thr Ala Thr Tyr Tyr Ala Thr Trp
    50                  55                  60

Ala Lys Gly Arg Phe Thr Ile Ser Lys Thr Ser Ser Thr Thr Val Thr
65                  70                  75                  80

Leu Gln Met Thr Ser Leu Thr Ala Ala Asp Thr Ala Thr Tyr Phe Cys
                85                  90                  95

Ala Arg Asp Leu Gly Phe Val Asp Tyr Ala Leu Glu Leu Trp Gly Pro
                100                 105                 110

Gly Thr Leu Val Thr Val Ser Ser
            115                 120

<210> SEQ ID NO 26
<211> LENGTH: 333
<212> TYPE: DNA
<213> ORGANISM: Artificial Sequence
<220> FEATURE:
<223> OTHER INFORMATION: Synthetic polynucleotide

<400> SEQUENCE: 26

```
gacattgtga tgacccagac tccagcctct gtggaggtag ctgtgggagg cacagtcacc      60
atcaagtgcc aggccagtga aaacatgtac aactctttag cctggtatca gcagaaacca     120
gggcagcctc ccaagctcct gatctacagg gcatccactc tggaatctgg ggtcccatcg     180
cggttcaaag gcagtggatc tgggacagag tacactctca ccatcagcga cctggagtgt     240
gccgatgctg ccacttacta ctgtcaatgt acttttttata gtcataataa taattatggt     300
ggtgctttcg gcggagggac cgaggtggtg gtc                                   333
```

<210> SEQ ID NO 27
<211> LENGTH: 111
<212> TYPE: PRT
<213> ORGANISM: Artificial Sequence
<220> FEATURE:
<223> OTHER INFORMATION: Synthetic polypeptide

<400> SEQUENCE: 27

```
Asp Ile Val Met Thr Gln Thr Pro Ala Ser Val Glu Val Ala Val Gly
1               5                   10                  15
Gly Thr Val Thr Ile Lys Cys Gln Ala Ser Glu Asn Met Tyr Asn Ser
            20                  25                  30
Leu Ala Trp Tyr Gln Gln Lys Pro Gly Gln Pro Pro Lys Leu Leu Ile
        35                  40                  45
Tyr Arg Ala Ser Thr Leu Glu Ser Gly Val Pro Ser Arg Phe Lys Gly
    50                  55                  60
Ser Gly Ser Gly Thr Glu Tyr Thr Leu Thr Ile Ser Asp Leu Glu Cys
65                  70                  75                  80
Ala Asp Ala Ala Thr Tyr Tyr Cys Gln Cys Thr Phe Tyr Ser His Asn
                85                  90                  95
Asn Asn Tyr Gly Gly Ala Phe Gly Gly Gly Thr Glu Val Val Val
            100                 105                 110
```

<210> SEQ ID NO 28
<211> LENGTH: 369
<212> TYPE: DNA
<213> ORGANISM: Artificial Sequence
<220> FEATURE:
<223> OTHER INFORMATION: Synthetic polynucleotide

<400> SEQUENCE: 28

```
caggagcagc tggaggagtc cgggggagac ctggtcaagc cgggggcatc cctgacactc      60
acctgcacag cctctggatt ctccttcagc agcagctact ggatatgctg ggtccgccag     120
gctccaggga aggggctgga gtggatcgca tgcatttatg ctggtgatgg tggtgccacc     180
tatgacgcga gctgggtgaa tggccgattc tccatctcca aaacctcgtc gaccacggtg     240
actctgcaaa tgaccagtct gacagccgcg gacacggcca cctatttctg tgcgagaaag     300
ggtgctgctc ctactactta ttactatttt aatttgtggg gcccaggcac cctggtcacc     360
gtctcctca                                                             369
```

<210> SEQ ID NO 29
<211> LENGTH: 123
<212> TYPE: PRT
<213> ORGANISM: Artificial Sequence
<220> FEATURE:
<223> OTHER INFORMATION: Synthetic polypeptide

<400> SEQUENCE: 29

```
Gln Glu Gln Leu Glu Glu Ser Gly Gly Asp Leu Val Lys Pro Gly Ala
1               5                   10                  15

Ser Leu Thr Leu Thr Cys Thr Ala Ser Gly Phe Ser Phe Ser Ser Ser
            20                  25                  30

Tyr Trp Ile Cys Trp Val Arg Gln Ala Pro Gly Lys Gly Leu Glu Trp
        35                  40                  45

Ile Ala Cys Ile Tyr Ala Gly Asp Gly Gly Ala Thr Tyr Asp Ala Ser
    50                  55                  60

Trp Val Asn Gly Arg Phe Ser Ile Ser Lys Thr Ser Ser Thr Thr Val
65                  70                  75                  80

Thr Leu Gln Met Thr Ser Leu Thr Ala Ala Asp Thr Ala Thr Tyr Phe
                85                  90                  95

Cys Ala Arg Lys Gly Ala Ala Pro Thr Thr Tyr Tyr Tyr Phe Asn Leu
            100                 105                 110

Trp Gly Pro Gly Thr Leu Val Thr Val Ser Ser
        115                 120
```

<210> SEQ ID NO 30
<211> LENGTH: 1806
<212> TYPE: DNA
<213> ORGANISM: Artificial Sequence
<220> FEATURE:
<223> OTHER INFORMATION: Synthetic polynucleotide

<400> SEQUENCE: 30

```
atgcagcagc agctggagga gtccggggga ggcctggtca agcctgaggg atccctgaca      60
ctcacctgca aagcctctgg attcgacctc ggtttctact tttacgcctg ttgggtccgc     120
caggctccag ggaagggcct ggagtggatc gcatgcattt atactgctgg tagtggtagc     180
acgtactacg cgagctgggc gaaaggccga ttcaccatct ccaaagcctc gtcgaccacg     240
gtgactctgc aaatgaccag tctggcagcc gcggacacgg ccacctattt ctgtgcgaga     300
tctactgcta atactagaag tacttattat cttaacttgt ggggcccagg caccctggtc     360
accgtctcct caggcggagg cggatcaggt ggtggcggat ctggaggtgg cggaagcgac     420
gtcgtgatga cccagactcc agcctccgtg tctgaacctg tggaggcac agtcaccatc     480
aagtgccagg ccagtcagag gattagtagt tacttatcct ggtatcagca gaaaccaggg     540
cagcgtccca agctcctgat ctttggtgca tccactctgg catctggggt ccctcgcgg      600
ttcaaaggca gtggatctgg gacagaatac actctcacca tcagcgacct ggagtgtgcc     660
gatgctgcca cttactactg tcagagttat gcttattttg atagtaataa ttggcatgct     720
tcggcggag ggaccgaggt ggtggtcaaa gcttccggag gtcccgaggg cggcagcctg     780
gccgcgctga ccgcgcacca ggcttgccac ctgccgctgg agactttcac ccgtcatcgc     840
cagccgcgcg gctgggaaca actggagcag tgcggctatc ggtgcagcg gctggtcgcc     900
ctctacctgg cggcgcggct gtcgtggaac caggtcgacc aggtgatccg caacgccctg     960
gccagccccg gcagcggcgg cgacctgggc gaagcgatcc gcgagcagcc ggagcaggc     1020
cgtctggccc tgaccctggc cgccgccgag agcgagcgct cgtccggca gggcaccggc    1080
```

```
aacgacgagg ccggcgcggc caacggcccg gcggacagcg cgacgccct gctggagcgc    1140 aactatccca ctggcgcgga gttcctcggc gacggcggcg acgtcagctt cagcacccgc    1200
ggcacgcaga actggacggt ggagcggctg ctccaggcgc accgccaact ggaggagcgc    1260
ggctatgtgt cgtcggcta ccacggcacc ttcctcgaag cggcgcaaag catcgtcttc    1320
ggcggggtgc gcgcgcgcag ccaggacctc gacgcgatct ggcgcggttt ctatatcgcc    1380
ggcgatccgg cgctggccta cggctacgcc caggaccagg aacccgacgc acgcggccgg    1440
atccgcaacg gtgccctgct gcgggtctat gtgccgcgct cgagcctgcc gggcttctac    1500
cgcaccagcc tgaccctggc cgcgccggag cggcggggcg aggtcgaacg gctgatcggc    1560
catccgctgc cgctgcgcct ggacgccatc accggccccg aggaggaagg cgggcgcctg    1620
gagaccattc tcggctggcc gctggccgag cgcaccgtgg tgattccctc ggcgatcccc    1680
accgacccgc gcaacgtcgg cggcgacctc gacccgtcca gcatccccga caaggaacag    1740
gcgatcagcg ccctgccgga ctacgccagc cagcccggca accgccgcg cgaggacctg    1800 aagtaa                                                                1806
```

<210> SEQ ID NO 31
<211> LENGTH: 601
<212> TYPE: PRT
<213> ORGANISM: Artificial Sequence
<220> FEATURE:
<223> OTHER INFORMATION: Synthetic polypeptide

<400> SEQUENCE: 31

```
Met Gln Gln Gln Leu Glu Glu Ser Gly Gly Gly Leu Val Lys Pro Glu
1               5                   10                  15

Gly Ser Leu Thr Leu Thr Cys Lys Ala Ser Gly Phe Asp Leu Gly Phe
            20                  25                  30

Tyr Phe Tyr Ala Cys Trp Val Arg Gln Ala Pro Gly Lys Gly Leu Glu
        35                  40                  45

Trp Ile Ala Cys Ile Tyr Thr Ala Gly Ser Gly Ser Thr Tyr Tyr Ala
    50                  55                  60

Ser Trp Ala Lys Gly Arg Phe Thr Ile Ser Lys Ala Ser Ser Thr Thr
65                  70                  75                  80

Val Thr Leu Gln Met Thr Ser Leu Ala Ala Ala Asp Thr Ala Thr Tyr
                85                  90                  95

Phe Cys Ala Arg Ser Thr Ala Asn Thr Arg Ser Thr Tyr Tyr Leu Asn
            100                 105                 110

Leu Trp Gly Pro Gly Thr Leu Val Thr Val Ser Ser Gly Gly Gly Gly
        115                 120                 125

Ser Gly Gly Gly Gly Ser Gly Gly Gly Gly Ser Asp Val Val Met Thr
    130                 135                 140

Gln Thr Pro Ala Ser Val Ser Glu Pro Val Gly Gly Thr Val Thr Ile
145                 150                 155                 160

Lys Cys Gln Ala Ser Gln Arg Ile Ser Ser Tyr Leu Ser Trp Tyr Gln
                165                 170                 175

Gln Lys Pro Gly Gln Arg Pro Lys Leu Leu Ile Phe Gly Ala Ser Thr
            180                 185                 190

Leu Ala Ser Gly Val Pro Ser Arg Phe Lys Gly Ser Gly Ser Gly Thr
        195                 200                 205

Glu Tyr Thr Leu Thr Ile Ser Asp Leu Glu Cys Ala Asp Ala Ala Thr
    210                 215                 220

Tyr Tyr Cys Gln Ser Tyr Ala Tyr Phe Asp Ser Asn Asn Trp His Ala
```

```
            225                 230                 235                 240
    Phe Gly Gly Gly Thr Glu Val Val Lys Ala Ser Gly Gly Pro Glu
                    245                 250                 255

Gly Gly Ser Leu Ala Ala Leu Thr Ala His Gln Ala Cys His Leu Pro
                260                 265                 270

Leu Glu Thr Phe Thr Arg His Arg Gln Pro Arg Gly Trp Glu Gln Leu
                275                 280                 285

Glu Gln Cys Gly Tyr Pro Val Gln Arg Leu Val Ala Leu Tyr Leu Ala
            290                 295                 300

Ala Arg Leu Ser Trp Asn Gln Val Asp Gln Val Ile Arg Asn Ala Leu
    305                 310                 315                 320

Ala Ser Pro Gly Ser Gly Asp Leu Gly Glu Ala Ile Arg Glu Gln
                    325                 330                 335

Pro Glu Gln Ala Arg Leu Ala Leu Thr Leu Ala Ala Glu Ser Glu
                340                 345                 350

Arg Phe Val Arg Gln Gly Thr Gly Asn Asp Glu Ala Gly Ala Ala Asn
                355                 360                 365

Gly Pro Ala Asp Ser Gly Asp Ala Leu Leu Glu Arg Asn Tyr Pro Thr
            370                 375                 380

Gly Ala Glu Phe Leu Gly Asp Gly Asp Val Ser Phe Ser Thr Arg
    385                 390                 395                 400

Gly Thr Gln Asn Trp Thr Val Glu Arg Leu Leu Gln Ala His Arg Gln
                    405                 410                 415

Leu Glu Glu Arg Gly Tyr Val Phe Val Gly Tyr His Gly Thr Phe Leu
                420                 425                 430

Glu Ala Ala Gln Ser Ile Val Phe Gly Gly Val Arg Ala Arg Ser Gln
                435                 440                 445

Asp Leu Asp Ala Ile Trp Arg Gly Phe Tyr Ile Ala Gly Asp Pro Ala
            450                 455                 460

Leu Ala Tyr Gly Tyr Ala Gln Asp Gln Glu Pro Asp Ala Arg Gly Arg
    465                 470                 475                 480

Ile Arg Asn Gly Ala Leu Leu Arg Val Tyr Val Pro Arg Ser Ser Leu
                    485                 490                 495

Pro Gly Phe Tyr Arg Thr Ser Leu Thr Leu Ala Ala Pro Glu Ala Ala
                500                 505                 510

Gly Glu Val Glu Arg Leu Ile Gly His Pro Leu Pro Leu Arg Leu Asp
                515                 520                 525

Ala Ile Thr Gly Pro Glu Glu Glu Gly Gly Arg Leu Glu Thr Ile Leu
            530                 535                 540

Gly Trp Pro Leu Ala Glu Arg Thr Val Val Ile Pro Ser Ala Ile Pro
    545                 550                 555                 560

Thr Asp Pro Arg Asn Val Gly Gly Asp Leu Pro Ser Ser Ile Pro
                    565                 570                 575

Asp Lys Glu Gln Ala Ile Ser Ala Leu Pro Asp Tyr Ala Ser Gln Pro
                580                 585                 590

Gly Lys Pro Pro Arg Glu Asp Leu Lys
            595                 600

<210> SEQ ID NO 32
<211> LENGTH: 1809
<212> TYPE: DNA
<213> ORGANISM: Artificial Sequence
<220> FEATURE:
<223> OTHER INFORMATION: Synthetic polynucleotide
```

<400> SEQUENCE: 32

```
atggaggtgc agctggtgga gtccggggga ggcctggtcc agcctggggg atccctgaga    60
ctctcctgcg cagcctctgg attcgacctc ggtttctact tttacgcctg ttgggtccgc   120
caggctccag ggaagggcct ggagtgggtc tcatgcattt atactgctgg tagtggtagc   180
acgtactacg cgagctgggc gaaaggccga ttcaccatct ccagagacaa ttcgaagaac   240
acgctgtatc tgcaaatgaa cagtctgaga gccgaggaca cggccgtgta ttactgtgcg   300
agatctactg ctaatactag aagtacttat tatcttaact tgtggggcca aggcaccctg   360
gtcaccgtct cctcaggcgg aggcggatca ggtggtggcg atctggagg tggcggaagc   420
gacatccaga tgacccagtc tccatcctcc ctgtctgcat ctgtgggaga cagagtcacc   480
atcacttgcc aggccagtca gaggattagt agttacttat cctggtatca gcagaaacca   540
gggaaagttc ccaagctcct gatctatggt gcatccactc tggcatctgg ggtcccctcg   600
cggttcagtg gcagtggatc tgggacagat ttcactctca ccatcagcag cctgcagcct   660
gaagatgttg ccacttacta ctgtcagagt tatgctattt tgatagtaa taattggcat   720
gctttcggcg agggaccaa ggtggagatc aaagcttccg aggtcccga gggcggcagc    780
ctggccgcgc tgaccgcgca ccaggcttgc cacctgccgc tggagacttt cacccgtcat   840
cgccagccgc gcggctggga acaactggag cagtgcggct atccggtgca gcggctggtc   900
gccctctacc tggcggcgcg gctgtcgtgg aaccaggtcg accaggtgat ccgcaacgcc   960
ctggccagcc ccggcagcgg cggcgacctg ggcgaagcga tccgcgagca gccggagcag  1020
gcccgtctgg ccctgaccct ggccgccgcc gagagcgagc gcttcgtccg cagggcacc   1080
ggcaacgacg aggccggcgc ggccaacggc ccggcggaca cggcgacgc cctgctggag  1140
cgcaactatc ccactggcgc ggagttcctc ggcgacggcg cgacgtcag cttcagcacc   1200
cgcggcacgc agaactggac ggtggagcgg ctgctccagg cgcaccgcca actggaggag  1260
cgcggctatg tgttcgtcgg ctaccacggc accttcctcg aagcggcgca agcatcgtc   1320
ttcggcgggg tgcgcgcgcg cagccaggac ctcgacgcga tctggcgcgg tttctatatc  1380
gccggcgatc cggcgctggc ctacggctac gcccaggacc aggaacccga cgcacgcggc  1440
cggatccgca acgtgccct gctgcgggtc tatgtgccgc gctcgagcct gccgggcttc  1500
taccgcacca gcctgaccct ggccgcgccg gaggcggcgg cgaggtcga acggctgatc  1560
ggccatccgc tgccgctgcg cctggacgcc atcaccggcc ccgaggagga aggcgggcgc  1620
ctggagacca ttctcggctg gccgctggcc gagcgcaccg tggtgattcc ctcggcgatc  1680
cccaccgacc cgcgcaacgt cggcggcgac ctcgacccgt ccagcatccc cgacaaggaa  1740
caggcgatca gcgccctgcc ggactacgcc agccagcccg gcaaaccgcc gcgcgaggac  1800
ctgaagtaa                                                          1809
```

<210> SEQ ID NO 33
<211> LENGTH: 602
<212> TYPE: PRT
<213> ORGANISM: Artificial Sequence
<220> FEATURE:
<223> OTHER INFORMATION: Synthetic polypeptide

<400> SEQUENCE: 33

```
Met Glu Val Gln Leu Val Glu Ser Gly Gly Gly Leu Val Gln Pro Gly
1               5                   10                  15
Gly Ser Leu Arg Leu Ser Cys Ala Ala Ser Gly Phe Asp Leu Gly Phe
            20                  25                  30
```

```
Tyr Phe Tyr Ala Cys Trp Val Arg Gln Ala Pro Gly Lys Gly Leu Glu
             35                  40                  45

Trp Val Ser Cys Ile Tyr Thr Ala Gly Ser Gly Ser Thr Tyr Tyr Ala
 50                  55                  60

Ser Trp Ala Lys Gly Arg Phe Thr Ile Ser Arg Asp Asn Ser Lys Asn
 65                  70                  75                  80

Thr Leu Tyr Leu Gln Met Asn Ser Leu Arg Ala Glu Asp Thr Ala Val
                 85                  90                  95

Tyr Tyr Cys Ala Arg Ser Thr Ala Asn Thr Arg Ser Thr Tyr Tyr Leu
                100                 105                 110

Asn Leu Trp Gly Gln Gly Thr Leu Val Thr Val Ser Ser Gly Gly Gly
             115                 120                 125

Gly Ser Gly Gly Gly Gly Ser Gly Gly Gly Gly Ser Asp Ile Gln Met
130                 135                 140

Thr Gln Ser Pro Ser Ser Leu Ser Ala Ser Val Gly Asp Arg Val Thr
145                 150                 155                 160

Ile Thr Cys Gln Ala Ser Gln Arg Ile Ser Ser Tyr Leu Ser Trp Tyr
                165                 170                 175

Gln Gln Lys Pro Gly Lys Val Pro Lys Leu Leu Ile Tyr Gly Ala Ser
             180                 185                 190

Thr Leu Ala Ser Gly Val Pro Ser Arg Phe Ser Gly Ser Gly Ser Gly
             195                 200                 205

Thr Asp Phe Thr Leu Thr Ile Ser Ser Leu Gln Pro Glu Asp Val Ala
210                 215                 220

Thr Tyr Tyr Cys Gln Ser Tyr Ala Tyr Phe Asp Ser Asn Asn Trp His
225                 230                 235                 240

Ala Phe Gly Gly Gly Thr Lys Val Glu Ile Lys Ala Ser Gly Gly Pro
                245                 250                 255

Glu Gly Gly Ser Leu Ala Ala Leu Thr Ala His Gln Ala Cys His Leu
             260                 265                 270

Pro Leu Glu Thr Phe Thr Arg His Arg Gln Pro Arg Gly Trp Glu Gln
             275                 280                 285

Leu Glu Gln Cys Gly Tyr Pro Val Gln Arg Leu Val Ala Leu Tyr Leu
             290                 295                 300

Ala Ala Arg Leu Ser Trp Asn Gln Val Asp Gln Val Ile Arg Asn Ala
305                 310                 315                 320

Leu Ala Ser Pro Gly Ser Gly Gly Asp Leu Gly Glu Ala Ile Arg Glu
                325                 330                 335

Gln Pro Glu Gln Ala Arg Leu Ala Leu Thr Leu Ala Ala Ala Glu Ser
             340                 345                 350

Glu Arg Phe Val Arg Gln Gly Thr Gly Asn Asp Glu Ala Gly Ala Ala
             355                 360                 365

Asn Gly Pro Ala Asp Ser Gly Asp Ala Leu Leu Glu Arg Asn Tyr Pro
370                 375                 380

Thr Gly Ala Glu Phe Leu Gly Asp Gly Gly Asp Val Ser Phe Ser Thr
385                 390                 395                 400

Arg Gly Thr Gln Asn Trp Thr Val Glu Arg Leu Leu Gln Ala His Arg
                405                 410                 415

Gln Leu Glu Glu Arg Gly Tyr Val Phe Val Gly Tyr His Gly Thr Phe
             420                 425                 430

Leu Glu Ala Ala Gln Ser Ile Val Phe Gly Gly Val Arg Ala Arg Ser
             435                 440                 445
```

```
Gln Asp Leu Asp Ala Ile Trp Arg Gly Phe Tyr Ile Ala Gly Asp Pro
    450                 455                 460

Ala Leu Ala Tyr Gly Tyr Ala Gln Asp Gln Glu Pro Asp Ala Arg Gly
465                 470                 475                 480

Arg Ile Arg Asn Gly Ala Leu Leu Arg Val Tyr Val Pro Arg Ser Ser
            485                 490                 495

Leu Pro Gly Phe Tyr Arg Thr Ser Leu Thr Leu Ala Ala Pro Glu Ala
        500                 505                 510

Ala Gly Glu Val Glu Arg Leu Ile Gly His Pro Leu Pro Leu Arg Leu
    515                 520                 525

Asp Ala Ile Thr Gly Pro Glu Glu Gly Gly Arg Leu Glu Thr Ile
530                 535                 540

Leu Gly Trp Pro Leu Ala Glu Arg Thr Val Val Ile Pro Ser Ala Ile
545                 550                 555                 560

Pro Thr Asp Pro Arg Asn Val Gly Gly Asp Leu Asp Pro Ser Ser Ile
                565                 570                 575

Pro Asp Lys Glu Gln Ala Ile Ser Ala Leu Pro Asp Tyr Ala Ser Gln
            580                 585                 590

Pro Gly Lys Pro Pro Arg Glu Asp Leu Lys
        595                 600

<210> SEQ ID NO 34
<211> LENGTH: 1800
<212> TYPE: DNA
<213> ORGANISM: Artificial Sequence
<220> FEATURE:
<223> OTHER INFORMATION: Synthetic polynucleotide

<400> SEQUENCE: 34
atgcaggagc agctggagga gtccggggga gacctggtcc agcctgaggg atccctgaca      60
ctcacctgca aagcctctgg gttagacttc agtagcagct actggatatg ttgggtccgc     120
caggctccag gaagggggct ggagtggatc gggtgtcgtc atacttttac tgctaacaca     180
tggtccgcga gctgggtgaa tggccggttc accatctcca aagcaccag cctaggcacg      240 gtggatctga aaatgaccag tctgacagcc gcggacacgg ccacctatt ctgtgccaga      300 gatgaatcta ataatgatgg ttgggatttt aagttgtggg gcccaggcac cctggtcacc     360
gtctcctcag gcggaggcgg atcaggtggt ggcggatctg gaggtggcgg aagcgcctat     420
gatatgaccc agactccagc ctccgtgtct gcagctgtgg gaggcacagt caccatcaag     480
tgccaggcca gtcagagcat tagtaactac ttagcctggt atcagcagaa accagggcag     540
cctcccaagc tcctgatcta ccaggcatcc actctggcac tggggtctc atcgcggttc     600 aaaggcagtg gatctgggac agaattcact ctcaccatca gcggcgtgga gtgtgccgat     660
gctgccactt actactgtca acagggttat actagtagta atgttgagaa tgttttcggc     720
ggagggaccg gggtggtggt caaagcttcc ggaggtcccg agggcggcag cctgccgcg      780 ctgaccgcgc accaggcttg ccacctgccg ctggagactt caccccgtca tcgccagccg     840
cgcggctggg aacaactgga gcagtgcggc tatccggtgc agcggctggt cgccctctac     900
ctggcggcgc ggctgtcgtg gaaccaggtc gaccaggtga tccgcaacgc cctgccagc      960 ccggcagcg gcggcgacct gggcgaagcg atccgcgagc agccggagca ggcccgtctg     1020
gccctgaccc tggccgccgc cgagagcgag cgcttcgtcc ggcagggcac cggcaacgac    1080
gaggccggcg cggccaacgg cccggcggac agcggcgacg ccctgctgga gcgcaactat    1140
cccactggcg cggagttcct cggcgacggc ggcgacgtca gcttcagcac ccgcggcacg    1200
```

```
cagaactgga cggtggagcg gctgctccag gcgcaccgcc aactggagga gcgcggctat    1260
gtgttcgtcg gctaccacgg caccttcctc gaagcggcgc aaagcatcgt cttcggcggg    1320
gtgcgcgcgc gcagccagga cctcgacgcg atctggcgcg gtttctatat cgccggcgat    1380
ccggcgctgg cctacggcta cgcccaggac caggaacccg acgcacgcgg ccggatccgc    1440
aacggtgccc tgctgcgggt ctatgtgccg cgctcgagcc tgccgggctt ctaccgcacc    1500
agcctgaccc tggccgcgcc ggaggcggcg ggcgaggtcg aacggctgat cggccatccg    1560
ctgccgctgc gcctggacgc catcaccggc cccgaggagg aaggcgggcg cctggagacc    1620
attctcggct ggccgctggc cgagcgcacc gtggtgattc cctcggcgat ccccaccgac    1680
ccgcgcaacg tcggcggcga cctcgacccg tccagcatcc ccgacaagga acaggcgatc    1740
agcgccctgc cggactacgc cagccagccc ggcaaaccgc cgcgcgagga cctgaagtaa    1800
```

<210> SEQ ID NO 35
<211> LENGTH: 599
<212> TYPE: PRT
<213> ORGANISM: Artificial Sequence
<220> FEATURE:
<223> OTHER INFORMATION: Synthetic polypeptide

<400> SEQUENCE: 35

```
Met Gln Glu Gln Leu Glu Glu Ser Gly Gly Asp Leu Val Gln Pro Glu
1               5                   10                  15

Gly Ser Leu Thr Leu Thr Cys Lys Ala Ser Gly Leu Asp Phe Ser Ser
            20                  25                  30

Ser Tyr Trp Ile Cys Trp Val Arg Gln Ala Pro Gly Lys Gly Leu Glu
        35                  40                  45

Trp Ile Gly Cys Arg His Thr Phe Thr Ala Asn Thr Trp Ser Ala Ser
    50                  55                  60

Trp Val Asn Gly Arg Phe Thr Ile Ser Arg Ser Thr Ser Leu Gly Thr
65                  70                  75                  80

Val Asp Leu Lys Met Thr Ser Leu Thr Ala Ala Asp Thr Ala Thr Tyr
                85                  90                  95

Phe Cys Ala Arg Asp Glu Ser Asn Asn Asp Gly Trp Asp Phe Lys Leu
            100                 105                 110

Trp Gly Pro Gly Thr Leu Val Thr Val Ser Ser Gly Gly Gly Gly Ser
        115                 120                 125

Gly Gly Gly Gly Ser Gly Gly Gly Ser Ala Tyr Asp Met Thr Gln
    130                 135                 140

Thr Pro Ala Ser Val Ser Ala Ala Val Gly Gly Thr Val Thr Ile Lys
145                 150                 155                 160

Cys Gln Ala Ser Gln Ser Ile Ser Asn Tyr Leu Ala Trp Tyr Gln Gln
                165                 170                 175

Lys Pro Gly Gln Pro Pro Lys Leu Leu Ile Tyr Gln Ala Ser Thr Leu
            180                 185                 190

Ala Pro Gly Val Ser Ser Arg Phe Lys Gly Ser Gly Ser Gly Thr Glu
        195                 200                 205

Phe Thr Leu Thr Ile Ser Gly Val Glu Cys Ala Asp Ala Ala Thr Tyr
    210                 215                 220

Tyr Cys Gln Gln Gly Tyr Thr Ser Ser Asn Val Glu Asn Val Phe Gly
225                 230                 235                 240

Gly Gly Thr Gly Val Val Val Lys Ala Ser Gly Gly Pro Glu Gly Gly
                245                 250                 255
```

Ser Leu Ala Ala Leu Thr Ala His Gln Ala Cys His Leu Pro Leu Glu
            260                 265                 270

Thr Phe Thr Arg His Arg Gln Pro Arg Gly Trp Glu Gln Leu Glu Gln
        275                 280                 285

Cys Gly Tyr Pro Val Gln Arg Leu Val Ala Leu Tyr Leu Ala Ala Arg
    290                 295                 300

Leu Ser Trp Asn Gln Val Asp Gln Val Ile Arg Asn Ala Leu Ala Ser
305                 310                 315                 320

Pro Gly Ser Gly Gly Asp Leu Gly Glu Ala Ile Arg Glu Gln Pro Glu
                325                 330                 335

Gln Ala Arg Leu Ala Leu Thr Leu Ala Ala Glu Ser Glu Arg Phe
            340                 345                 350

Val Arg Gln Gly Thr Gly Asn Asp Glu Ala Gly Ala Ala Asn Gly Pro
        355                 360                 365

Ala Asp Ser Gly Asp Ala Leu Leu Glu Arg Asn Tyr Pro Thr Gly Ala
370                 375                 380

Glu Phe Leu Gly Asp Gly Gly Asp Val Ser Phe Ser Thr Arg Gly Thr
385                 390                 395                 400

Gln Asn Trp Thr Val Glu Arg Leu Leu Gln Ala His Arg Gln Leu Glu
            405                 410                 415

Glu Arg Gly Tyr Val Phe Val Gly Tyr His Gly Thr Phe Leu Glu Ala
        420                 425                 430

Ala Gln Ser Ile Val Phe Gly Gly Val Arg Ala Arg Ser Gln Asp Leu
    435                 440                 445

Asp Ala Ile Trp Arg Gly Phe Tyr Ile Ala Gly Asp Pro Ala Leu Ala
450                 455                 460

Tyr Gly Tyr Ala Gln Asp Gln Glu Pro Asp Ala Arg Gly Arg Ile Arg
465                 470                 475                 480

Asn Gly Ala Leu Leu Arg Val Tyr Val Pro Arg Ser Ser Leu Pro Gly
            485                 490                 495

Phe Tyr Arg Thr Ser Leu Thr Leu Ala Ala Pro Glu Ala Ala Gly Glu
        500                 505                 510

Val Glu Arg Leu Ile Gly His Pro Leu Pro Leu Arg Leu Asp Ala Ile
    515                 520                 525

Thr Gly Pro Glu Glu Glu Gly Gly Arg Leu Glu Thr Ile Leu Gly Trp
530                 535                 540

Pro Leu Ala Glu Arg Thr Val Val Ile Pro Ser Ala Ile Pro Thr Asp
545                 550                 555                 560

Pro Arg Asn Val Gly Gly Asp Leu Asp Pro Ser Ser Ile Pro Asp Lys
            565                 570                 575

Glu Gln Ala Ile Ser Ala Leu Pro Asp Tyr Ala Ser Gln Pro Gly Lys
        580                 585                 590

Pro Pro Arg Glu Asp Leu Lys
        595

<210> SEQ ID NO 36
<211> LENGTH: 1791
<212> TYPE: DNA
<213> ORGANISM: Artificial Sequence
<220> FEATURE:
<223> OTHER INFORMATION: Synthetic polynucleotide

<400> SEQUENCE: 36
atgcaggagc agctggtgga gtccggggga ggcctggtcc agcctggggc atccctgaca      60
ctcacctgca cagcctctgg aatcgacttc agtcgctact acatgtgttg ggtccgccag     120

```
gctccaggga agggactgga ggggatcgca tgtatttata ttggtggtag tggtagcact    180
tactacgcga gctgggcgaa aggccgattc accatctcca aagcctcgtc gaccacggtg    240
actctgcaaa tgaccagtct gacagccgcg gacacggcca cttatttctg tgcgagaggg    300
actaatctta attatatttt taggttgtgg ggcccaggca ccctggtcac cgtctcctca    360
ggcggaggcg gatcaggtgg tggcggatct ggaggtggcg aagcgatgt tgtgatgacc    420 cagactccat ctcccgtgtc tgcagctgtg ggaggcacag tcaccatcaa gtgccaggcc    480
agtcagagca ttaataatgg tttagcctgg tatcagcaga aaccagggca gcctcccagg    540
ctcctgatct attctgcatc caatctggaa tctggggtcc catcgcggtt caaaggcagt    600
ggatctggga cagagttcac tctcaccatc agcgacctgg agtgtgacga tgctgccact    660
tactattgtc aatgtatttg ggatggtaat agttatgtta atgctttcgg cggagggacc    720
gaggtggtgg tcaaagcttc cggaggtccc gagggcggca gcctggccgc gctgaccgcg    780
caccaggctt gccacctgcc gctggagact ttcacccgtc atcgccagcc gcgcggctgg    840
gaacaactgg agcagtgcgg ctatccggtg cagcggctgg tcgccctcta cctggcggcg    900
cggctgtcgt ggaaccaggt cgaccaggtg atccgcaacg ccctggccag ccccggcagc    960
ggcggcgacc tgggcgaagc gatccgcgag cagccggagc aggcccgtct ggccctgacc    1020
ctggccgccg ccgagagcga gcgcttcgtc cggcagggca ccggcaacga cgaggccggc    1080
gcggccaacg gcccggcgga cagcggcgac gccctgctgg agcgcaacta tcccactggc    1140
gcggagttcc tcggcgacgg cggcgacgtc agcttcagca cccgcggcac gcagaactgg    1200
acggtggagc ggctgctcca ggcgcaccgc caactggagg agcgcggcta tgtgttcgtc    1260
ggctaccacg gcaccttcct cgaagcggcg caaagcatcg tcttcggcgg ggtgcgcgcg    1320
cgcagccagg acctcgacgc gatctggcgc ggtttctata tcgccggcga tccggcgctg    1380
gcctacggct acgcccagga ccaggaaccc gacgcacgcg gccggatccg caacggtgcc    1440
ctgctgcggg tctatgtgcc gcgctcgagc ctgccgggct ctaccgcac cagcctgacc    1500 ctggccgcgc cggaggcggc gggcgaggtc aacggctga tcggccatcc gctgccgctg    1560
cgcctggacg ccatcaccgg ccccgaggag gaaggcgggc gcctggagac cattctcggc    1620
tggccgctgg ccgagcgcac cgtggtgatt ccctcggcga tccccaccga cccgcgcaac    1680
gtcggcggcg acctcgaccc gtccagcatc cccgacaagg aacaggcgat cagcgccctg    1740
ccggactacg ccagccagcc cggcaaaccg ccgcgcgagg acctgaagta a             1791
```

<210> SEQ ID NO 37
<211> LENGTH: 596
<212> TYPE: PRT
<213> ORGANISM: Artificial Sequence
<220> FEATURE:
<223> OTHER INFORMATION: Synthetic polypeptide

<400> SEQUENCE: 37

```
Met Gln Glu Gln Leu Val Glu Ser Gly Gly Gly Leu Val Gln Pro Gly
1               5                   10                  15

Ala Ser Leu Thr Leu Thr Cys Thr Ala Ser Gly Ile Asp Phe Ser Arg
            20                  25                  30

Tyr Tyr Met Cys Trp Val Arg Gln Ala Pro Gly Lys Gly Leu Glu Gly
        35                  40                  45

Ile Ala Cys Ile Tyr Ile Gly Gly Ser Gly Ser Thr Tyr Tyr Ala Ser
    50                  55                  60
```

```
Trp Ala Lys Gly Arg Phe Thr Ile Ser Lys Ala Ser Ser Thr Thr Val
 65                  70                  75                  80

Thr Leu Gln Met Thr Ser Leu Thr Ala Ala Asp Thr Ala Thr Tyr Phe
                 85                  90                  95

Cys Ala Arg Gly Thr Asn Leu Asn Tyr Ile Phe Arg Leu Trp Gly Pro
            100                 105                 110

Gly Thr Leu Val Thr Val Ser Ser Gly Gly Gly Ser Gly Gly Gly
            115                 120                 125

Gly Ser Gly Gly Gly Ser Asp Val Val Met Thr Gln Thr Pro Ser
    130                 135                 140

Pro Val Ser Ala Ala Val Gly Gly Thr Val Thr Ile Lys Cys Gln Ala
145                 150                 155                 160

Ser Gln Ser Ile Asn Asn Gly Leu Ala Trp Tyr Gln Gln Lys Pro Gly
                165                 170                 175

Gln Pro Pro Arg Leu Leu Ile Tyr Ser Ala Ser Asn Leu Glu Ser Gly
            180                 185                 190

Val Pro Ser Arg Phe Lys Gly Ser Gly Ser Gly Thr Glu Phe Thr Leu
            195                 200                 205

Thr Ile Ser Asp Leu Glu Cys Asp Asp Ala Ala Thr Tyr Tyr Cys Gln
    210                 215                 220

Cys Ile Trp Asp Gly Asn Ser Tyr Val Asn Ala Phe Gly Gly Gly Thr
225                 230                 235                 240

Glu Val Val Val Lys Ala Ser Gly Gly Pro Glu Gly Gly Ser Leu Ala
                245                 250                 255

Ala Leu Thr Ala His Gln Ala Cys His Leu Pro Leu Glu Thr Phe Thr
            260                 265                 270

Arg His Arg Gln Pro Arg Gly Trp Glu Gln Leu Glu Gln Cys Gly Tyr
    275                 280                 285

Pro Val Gln Arg Leu Val Ala Leu Tyr Leu Ala Ala Arg Leu Ser Trp
            290                 295                 300

Asn Gln Val Asp Gln Val Ile Arg Asn Ala Leu Ala Ser Pro Gly Ser
305                 310                 315                 320

Gly Gly Asp Leu Gly Glu Ala Ile Arg Glu Gln Pro Glu Gln Ala Arg
                325                 330                 335

Leu Ala Leu Thr Leu Ala Ala Ala Glu Ser Glu Arg Phe Val Arg Gln
            340                 345                 350

Gly Thr Gly Asn Asp Glu Ala Gly Ala Ala Asn Gly Pro Ala Asp Ser
    355                 360                 365

Gly Asp Ala Leu Leu Glu Arg Asn Tyr Pro Thr Gly Ala Glu Phe Leu
    370                 375                 380

Gly Asp Gly Gly Asp Val Ser Phe Ser Thr Arg Gly Thr Gln Asn Trp
385                 390                 395                 400

Thr Val Glu Arg Leu Leu Gln Ala His Arg Gln Leu Glu Glu Arg Gly
                405                 410                 415

Tyr Val Phe Val Gly Tyr His Gly Thr Phe Leu Glu Ala Ala Gln Ser
            420                 425                 430

Ile Val Phe Gly Gly Val Arg Ala Arg Ser Gln Asp Leu Asp Ala Ile
            435                 440                 445

Trp Arg Gly Phe Tyr Ile Ala Gly Asp Pro Ala Leu Ala Tyr Gly Tyr
    450                 455                 460

Ala Gln Asp Gln Glu Pro Asp Ala Arg Gly Arg Ile Arg Asn Gly Ala
465                 470                 475                 480

Leu Leu Arg Val Tyr Val Pro Arg Ser Ser Leu Pro Gly Phe Tyr Arg
```

```
              485                 490                 495
Thr Ser Leu Thr Leu Ala Ala Pro Glu Ala Ala Gly Glu Val Glu Arg
            500                 505                 510

Leu Ile Gly His Pro Leu Pro Leu Arg Leu Asp Ala Ile Thr Gly Pro
            515                 520                 525

Glu Glu Glu Gly Gly Arg Leu Glu Thr Ile Leu Gly Trp Pro Leu Ala
            530                 535                 540

Glu Arg Thr Val Val Ile Pro Ser Ala Ile Pro Thr Asp Pro Arg Asn
545                 550                 555                 560

Val Gly Gly Asp Leu Asp Pro Ser Ser Ile Pro Asp Lys Glu Gln Ala
                565                 570                 575

Ile Ser Ala Leu Pro Asp Tyr Ala Ser Gln Pro Gly Lys Pro Pro Arg
                580                 585                 590

Glu Asp Leu Lys
            595

<210> SEQ ID NO 38
<211> LENGTH: 1803
<212> TYPE: DNA
<213> ORGANISM: Artificial Sequence
<220> FEATURE:
<223> OTHER INFORMATION: Synthetic polynucleotide

<400> SEQUENCE: 38
atgcaggagc agctggagga gtccggggga gacctggtca agccgggggc atccctgaca      60
ctcacctgca cagcctctgg attctccttc agcagcagct actggatatg ctgggtccgc     120
caggctccag ggaaggggct ggagtggatc gcatgcattt atgctggtga tggtggtgcc     180
acctatgacg cgagctgggt gaatggccga ttctccatct ccaaaacctc gtcgaccacg     240
gtgactctgc aaatgaccag tctgacagcc gcggacacgg ccacctattt ctgtgcgaga     300
aagggtgctg ctcctactac ttattactat tttaatttgt ggggcccagg caccctggtc     360
accgtctcct caggcggagg cggatcaggt ggtggcggat ctggaggtgg cggaagcgcc     420
tatgatatga cccagactcc agcctccgtg tctgcagctg tgggaggcac agtcaccatc     480
aagtgccagg ccagtcagag cattagcact gcattagcct ggtatcagca gaaaccaggg     540
cagcctccca aggtcctgat ctatgctgca tccaatctgg catctggggt ctcatcgcgg     600
ttcaaaggca gtggatctgg gacagagttc actctcacca tcagcgacct ggagtgtgcc     660
gatgctgcca cttactattg tcaacaggct gctaccatta ttaatgttga taatgttttc     720
ggcggaggga ccgaggtggt ggtcaaagct tccggaggtc cgagggcgg cagcctggcc     780 gcgctgaccg cgcaccaggc ttgccacctg ccgctggaga ctttcacccg tcatcgccag     840
ccgcgcggct gggaacaact ggagcagtgc ggctatccgg tgcagcggct ggtcgccctc     900
tacctggcgg cgcggctgtc gtggaaccag gtcgaccagg tgatccgcaa cgccctggcc     960
agccccggca gcggcggcga cctgggcgaa gcgatccgcg agcagccgga gcaggcccgt    1020
ctggccctga ccctggccgc cgccgagagc gagcgcttcg tccggcaggg caccggcaac    1080
gacgaggccg gcgcggccaa cggcccggcg gacagcggcg acgccctgct ggagcgcaac    1140
tatcccactg gcgcggagtt cctcggcgac ggcggcgacg tcagcttcag cacccgcggc    1200
acgcagaact ggacggtgga gcggctgctc caggcgcacc gccaactgga ggagcgcggc    1260
tatgtgttcg tcggctacca cggcaccttc ctcgaagcgg cgcaaagcat cgtcttcggc    1320
ggggtgcgcg cgcgcagcca ggacctcgac gcgatctggc gcggtttcta tatcgccggc    1380
```

-continued

```
gatccggcgc tggcctacgg ctacgcccag gaccaggaac ccgacgcacg cggccggatc   1440
cgcaacggtg ccctgctgcg ggtctatgtg ccgcgctcga gcctgccggg cttctaccgc   1500
accagcctga ccctggccgc gccggaggcg gcgggcgagg tcgaacggct gatcggccat   1560
ccgctgccgc tgcgcctgga cgccatcacc ggccccgagg aggaaggcgg gcgcctggag   1620
accattctcg gctggccgct ggccgagcgc accgtggtga ttccctcggc gatccccacc   1680
gacccgcgca acgtcggcgg cgacctcgac ccgtccagca tccccgacaa ggaacaggcg   1740
atcagcgccc tgccggacta cgccagccag cccggcaaac cgccgcgcga ggacctgaag   1800
taa                                                                 1803
```

<210> SEQ ID NO 39
<211> LENGTH: 600
<212> TYPE: PRT
<213> ORGANISM: Artificial Sequence
<220> FEATURE:
<223> OTHER INFORMATION: Synthetic polypeptide

<400> SEQUENCE: 39

```
Met Gln Glu Gln Leu Glu Glu Ser Gly Gly Asp Leu Val Lys Pro Gly
1               5                   10                  15

Ala Ser Leu Thr Leu Thr Cys Thr Ala Ser Gly Phe Ser Phe Ser Ser
            20                  25                  30

Ser Tyr Trp Ile Cys Trp Val Arg Gln Ala Pro Gly Lys Gly Leu Glu
        35                  40                  45

Trp Ile Ala Cys Ile Tyr Ala Gly Asp Gly Ala Thr Tyr Asp Ala
    50                  55                  60

Ser Trp Val Asn Gly Arg Phe Ser Ile Ser Lys Thr Ser Ser Thr Thr
65                  70                  75                  80

Val Thr Leu Gln Met Thr Ser Leu Thr Ala Ala Asp Thr Ala Thr Tyr
                85                  90                  95

Phe Cys Ala Arg Lys Gly Ala Ala Pro Thr Thr Tyr Tyr Tyr Phe Asn
            100                 105                 110

Leu Trp Gly Pro Gly Thr Leu Val Thr Val Ser Ser Gly Gly Gly Gly
        115                 120                 125

Ser Gly Gly Gly Gly Ser Gly Gly Gly Ser Ala Tyr Asp Met Thr
    130                 135                 140

Gln Thr Pro Ala Ser Val Ser Ala Ala Val Gly Gly Thr Val Thr Ile
145                 150                 155                 160

Lys Cys Gln Ala Ser Gln Ser Ile Ser Thr Ala Leu Ala Trp Tyr Gln
                165                 170                 175

Gln Lys Pro Gly Gln Pro Pro Lys Val Leu Ile Tyr Ala Ala Ser Asn
            180                 185                 190

Leu Ala Ser Gly Val Ser Ser Arg Phe Lys Gly Ser Gly Ser Gly Thr
        195                 200                 205

Glu Phe Thr Leu Thr Ile Ser Asp Leu Glu Cys Ala Asp Ala Ala Thr
    210                 215                 220

Tyr Tyr Cys Gln Gln Ala Ala Thr Ile Ile Asn Val Asp Asn Val Phe
225                 230                 235                 240

Gly Gly Gly Thr Glu Val Val Val Lys Ala Ser Gly Gly Pro Glu Gly
                245                 250                 255

Gly Ser Leu Ala Ala Leu Thr Ala His Gln Ala Cys His Leu Pro Leu
            260                 265                 270

Glu Thr Phe Thr Arg His Arg Gln Pro Arg Gly Trp Glu Gln Leu Glu
        275                 280                 285
```

```
Gln Cys Gly Tyr Pro Val Gln Arg Leu Val Ala Leu Tyr Leu Ala Ala
    290                 295                 300

Arg Leu Ser Trp Asn Gln Val Asp Gln Val Ile Arg Asn Ala Leu Ala
305                 310                 315                 320

Ser Pro Gly Ser Gly Asp Leu Gly Glu Ala Ile Arg Glu Gln Pro
                325                 330                 335

Glu Gln Ala Arg Leu Ala Leu Thr Leu Ala Ala Glu Ser Glu Arg
            340                 345                 350

Phe Val Arg Gln Gly Thr Gly Asn Asp Glu Ala Gly Ala Ala Asn Gly
        355                 360                 365

Pro Ala Asp Ser Gly Asp Ala Leu Leu Glu Arg Asn Tyr Pro Thr Gly
    370                 375                 380

Ala Glu Phe Leu Gly Asp Gly Asp Val Ser Phe Ser Thr Arg Gly
385                 390                 395                 400

Thr Gln Asn Trp Thr Val Glu Arg Leu Leu Gln Ala His Arg Gln Leu
                405                 410                 415

Glu Glu Arg Gly Tyr Val Phe Val Gly Tyr His Gly Thr Phe Leu Glu
            420                 425                 430

Ala Ala Gln Ser Ile Val Phe Gly Gly Val Arg Ala Arg Ser Gln Asp
        435                 440                 445

Leu Asp Ala Ile Trp Arg Gly Phe Tyr Ile Ala Gly Asp Pro Ala Leu
    450                 455                 460

Ala Tyr Gly Tyr Ala Gln Asp Gln Glu Pro Asp Ala Arg Gly Arg Ile
465                 470                 475                 480

Arg Asn Gly Ala Leu Leu Arg Val Tyr Val Pro Arg Ser Ser Leu Pro
                485                 490                 495

Gly Phe Tyr Arg Thr Ser Leu Thr Leu Ala Ala Pro Glu Ala Ala Gly
            500                 505                 510

Glu Val Glu Arg Leu Ile Gly His Pro Leu Pro Leu Arg Leu Asp Ala
        515                 520                 525

Ile Thr Gly Pro Glu Glu Glu Gly Gly Arg Leu Glu Thr Ile Leu Gly
    530                 535                 540

Trp Pro Leu Ala Glu Arg Thr Val Val Ile Pro Ser Ala Ile Pro Thr
545                 550                 555                 560

Asp Pro Arg Asn Val Gly Gly Asp Leu Asp Pro Ser Ser Ile Pro Asp
                565                 570                 575

Lys Glu Gln Ala Ile Ser Ala Leu Pro Asp Tyr Ala Ser Gln Pro Gly
            580                 585                 590

Lys Pro Pro Arg Glu Asp Leu Lys
        595                 600
```

MESOTHELIN DOMAIN-SPECIFIC MONOCLONAL ANTIBODIES AND USE THEREOF

CROSS REFERENCE TO RELATED APPLICATIONS

This is a continuation of U.S. patent application Ser. No. 14/421,599, filed Feb. 13, 2015, which is the U.S. National Stage of International Application No. PCT/US2013/055273, filed Aug. 16, 2013, published in English under PCT Article 21(2), which claims the benefit of U.S. Provisional Application No. 61/691,719, filed Aug. 21, 2012. The above-referenced applications are herein incorporated by reference in their entirety.

FIELD

This disclosure concerns monoclonal antibodies specific for mesothelin, particularly monoclonal antibodies raised against fragments of mesothelin, and their use for the diagnosis and treatment of cancer.

BACKGROUND

Human mesothelin is a 40 kDa cell-surface glycosylphosphatidylinositol (GPI)-linked glycoprotein. The protein is synthesized as a 70 kD precursor which is then proteolytically processed. The 30 kD amino terminus of mesothelin is secreted and is referred to as megakaryocyte potentiating factor (Yamaguchi et al., *J. Biol. Chem.* 269:805 808, 1994). The 40 kD carboxyl terminus remains bound to the membrane as mature mesothelin (Chang et al., *Natl. Acad. Sci. USA* 93:136 140, 1996).

Mesothelin is present at relatively low levels in mesothelial cells of the pleura, peritoneum and pericardium of healthy individuals, but is highly expressed in a number of different cancers, including mesotheliomas, stomach cancer, squamous cell carcinomas, prostate cancer, pancreatic cancer, lung cancer, cholangiocarcinoma, breast cancer and ovarian cancer (Hassan et al., *Clin. Cancer Res.* 10:3937-3942, 2004; McGuire et al., *N. Engl. J. Med.* 334:1-6, 1996; Argani et aL, *Clin. Cancer Res.* 7:3862-3868, 2001; Hassan et al., *Appl. Immunohistochem. Mol. Morphol.* 13:243-247, 2005; Li et al., *Mol. Cancer Ther.* 7:286-296, 2008; Yu et al., *J Cancer* 1:141-1749, 2010; Tchou et al., *Breast Cancer Res Treat* 133(2):799-804, 2012; U.S. Pat. No. 7,081,518). In particular, it has been reported that a majority of serous carcinomas of the ovary and adenocarcinomas of the pancreas express high levels of mesothelin (Yen et al., *Clin. Cancer Res.* 12:827-831, 2006). In addition, high levels of mesothelin have been detected in greater than 55% of lung cancers and greater than 70% of ovarian cancers (Hassan et al., *Appl. Immunohistochem. Mol. Morphol.* 13:243-247, 2005; Ho et al., *Clin. Cancer Res.* 13(5):1571-1575, 2007). The limited expression of mesothelin on normal cells makes it a viable target for tumor immunotherapy.

Mesothelin can also be used as a marker for diagnosis and prognosis of certain types of cancer because trace amounts of mesothelin can be detected in the blood of some patients with mesothelin-positive cancers (Cristaudo et al., *Clin. Cancer Res.* 13:5076-5081, 2007). It has been reported that mesothelin may be released into serum through deletion at its carboxyl terminus or by proteolytic cleavage from its membrane bound form (Hassan et al., *Clin. Cancer Res.* 10:3937-3942, 2004). An increase in the soluble form of mesothelin was detectable several years before malignant mesotheliomas occurred among workers exposed to asbestos (Creaney and Robinson, *Hematol. Oncol. Clin. North Am.* 19:1025-1040, 2005). Furthermore, patients with ovarian, pancreatic, and lung cancers also have elevated soluble mesothelin in serum (Cristaudo et al., *Clin. Cancer Res.* 13:5076-5081, 2007; Hassan et al., *Clin. Cancer Res.* 12:447-453, 2006; Croso et al., *Cancer Detect. Prev.* 30:180-187, 2006).

SUMMARY

Disclosed herein is a panel of monoclonal antibodies that bind with high affinity to full-length mesothelin and/or mesothelin fragments. The antibodies provided herein include immunoglobulin molecules, such as IgG antibodies, as well as antibody fragments. Further provided are compositions including the antibodies that bind, for example specifically bind, to mesothelin, nucleic acid molecules encoding these antibodies, expression vectors comprising the nucleic acid molecules, and isolated host cells that express the nucleic acid molecules. Also provided are immunoconjugates comprising the antibodies disclosed herein and an effector molecule, such as a toxin.

The antibodies and compositions provided herein can be used for a variety of purposes, such as for confirming the diagnosis of a cancer that expresses mesothelin, for example mesothelioma, prostate cancer, lung cancer, stomach cancer, squamous cell carcinoma, pancreatic cancer, cholangiocarcinoma, breast cancer or ovarian cancer. Thus, provided herein is a method of confirming the diagnosis of cancer in a subject by contacting a sample from the subject diagnosed with cancer with a monoclonal antibody that binds mesothelin, and detecting binding of the antibody to the sample. An increase in binding of the antibody to the sample relative to binding of the antibody to a control sample confirms the cancer diagnosis. In some embodiments, the method further includes contacting a second antibody that specifically recognizes the mesothelin-specific antibody with the sample, and detecting binding of the second antibody.

Similarly, provided herein is a method of detecting a cancer that expresses mesothelin in a subject. The method includes contacting a sample from the subject with a monoclonal antibody described herein, and detecting binding of the antibody to the sample. An increase in binding of the antibody to the sample relative to a control sample detects cancer in the subject. In some embodiments, the methods further comprise contacting a second antibody that specifically recognizes the mesothelin-specific antibody with the sample, and detecting binding of the second antibody.

Further provided is a method of treating a subject with cancer, for example mesothelioma, prostate cancer, lung cancer, stomach cancer, squamous cell carcinoma, pancreatic cancer, cholangiocarcinoma, breast cancer or ovarian cancer, by selecting a subject with a cancer that expresses mesothelin and administering to the subject a therapeutically effective amount of a monoclonal antibody specific for mesothelin, or an immunoconjugate comprising the antibody.

Also provided is a method for inhibiting tumor growth or metastasis in a subject by selecting a subject with a cancer that expresses mesothelin and administering to the subject a therapeutically effective amount of an antibody, immunoconjugate or composition disclosed herein.

The foregoing and other objects, features, and advantages of the invention will become more apparent from the following detailed description, which proceeds with reference to the accompanying figures.

BRIEF DESCRIPTION OF THE DRAWINGS

FIGS. 8A and 8B are immunoblots showing binding of YP158 to mesothelin in cancer cells and tissues. (FIG. 8A) Immunoblot analysis of mesothelin proteins in human liver cancer cell lines. Forty µg of whole cell lysate was loaded for each sample except A431 and H9 (only 2 µg of total protein was loaded). (FIG. 8B) Immunoblot analysis of mesothelin proteins in cancer specimens. OVCAR3 (a human ovarian cancer cell line) and H9 (A431.MSLN+) were used as positive controls. A431 (MSLN−) was used as a negative control. MSLN: mesothelin (~40 kDa); Precursor: ~70 kDa.

SEQUENCE LISTING

Figure 1:
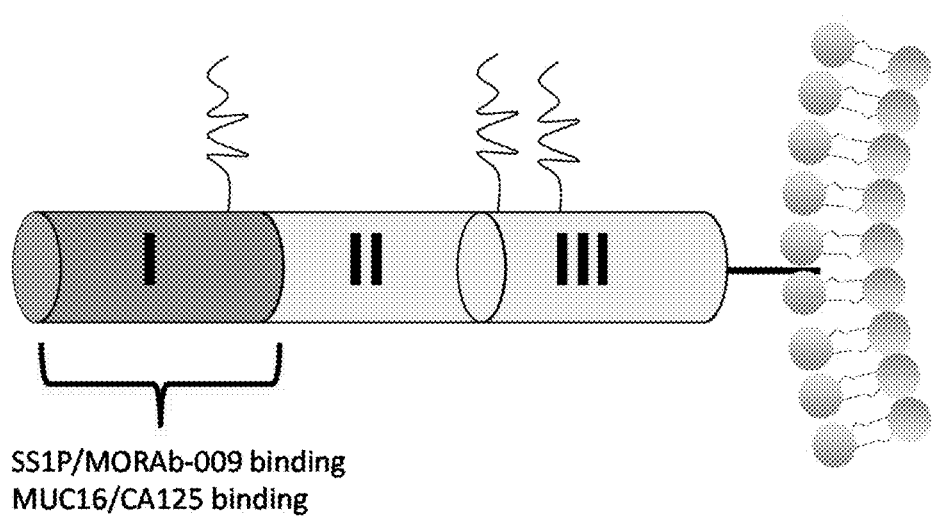
FIG. 1 is a schematic of the structure of mesothelin. Current anti-mesothelin therapeutic antibodies and immunotoxins (including SS1P and MORAb-009) recognize epitopes within the highly immunogenic N-terminal Region I of cell surface mesothelin, which also binds mucin MUC16/CA125.
Figure 2A:
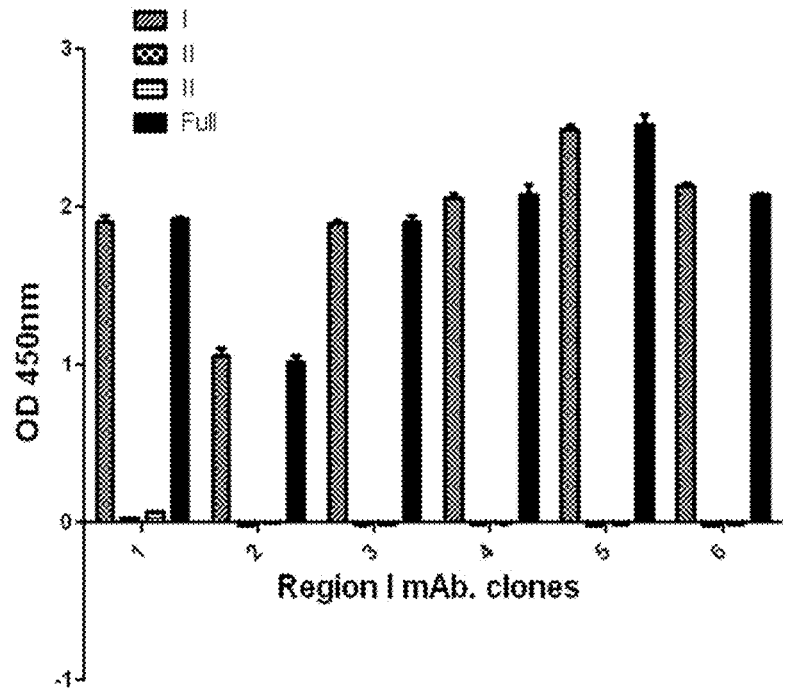
FIGS. 2A-2D are graphs showing characterization of domain-specific rabbit monoclonal antibodies (mAbs) by ELISA. ELISA plates were coated with 5 µg/mL of full-length mesothelin (Full), Region I (residues 296-390), Region II (residues 391-486) and Region III (residues 487-598) fragments. Rabbit hybridoma supernatants of Region I mAb clones (FIG. 2A), Region II mAb clones (FIG. 2B), Region III mAb clones (FIG. 2C) and conformation-sensitive mAb clones (FIG. 2D) were added into the ELISA plates and rabbit mAb binding to mesothelin or its fragments was detected by a goat anti-rabbit IgG light chain-specific HRP conjugate.
Figure 2B:
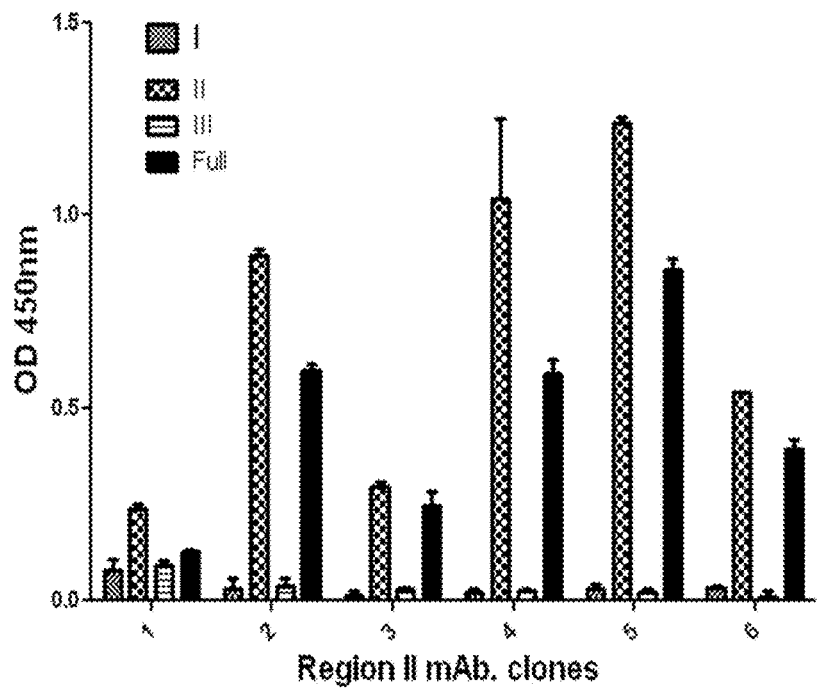
Figure 2C:
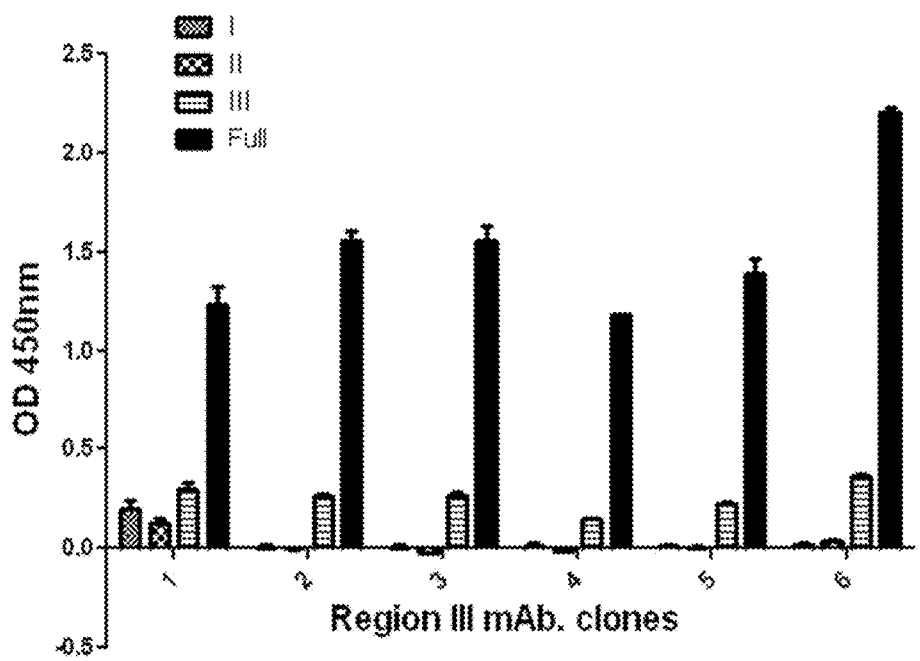
Figure 2D:
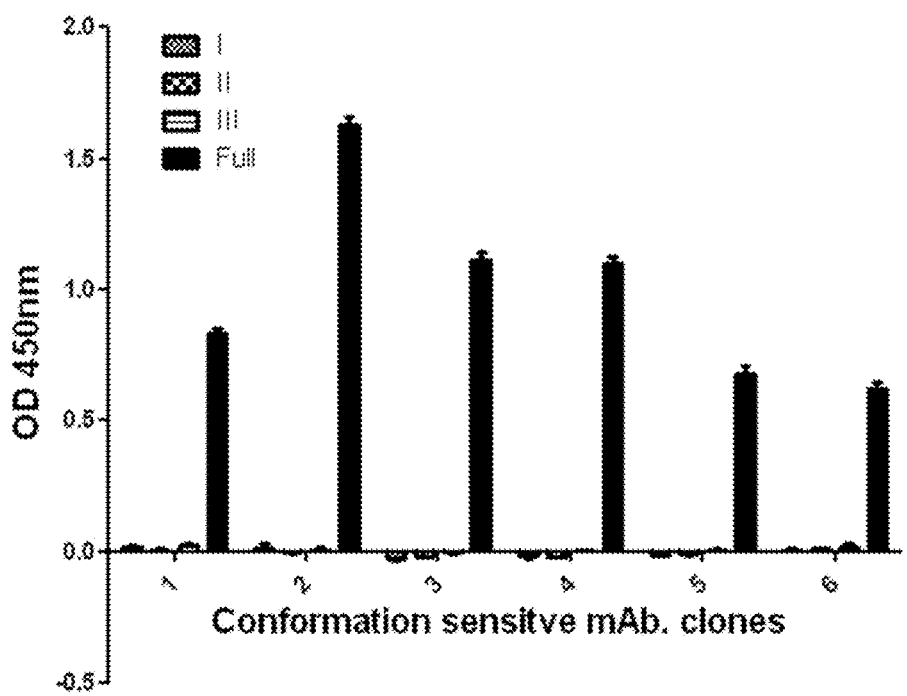
Figure 3A:
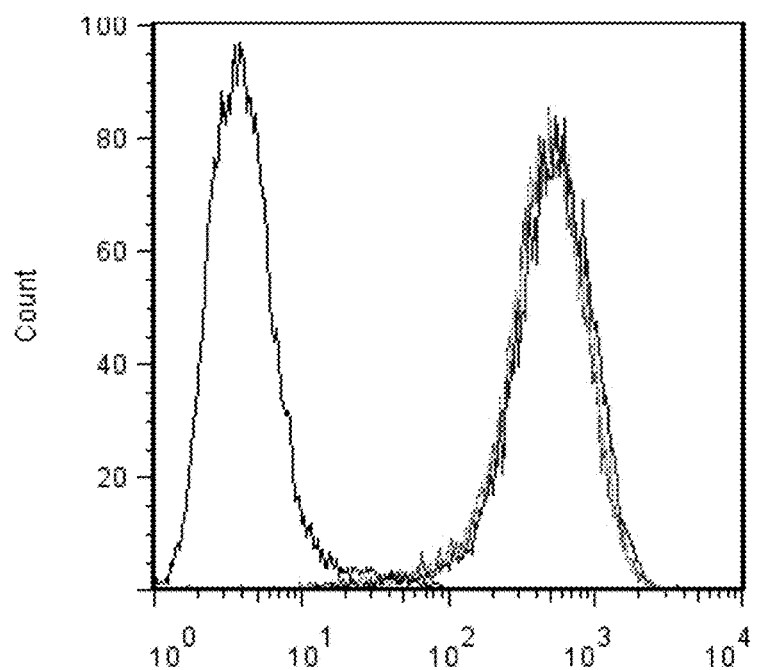
FIGS. 3A-3D are flow cytometry plots showing binding of rabbit mAbs to the NCI-H226 (mesothelioma) cell line. NCI-H226 cells ($1\times10^6$) were incubated with rabbit hybridoma supernatant (1:2 dilutions in FACS buffer) of Region I binders (FIG. 3A), confirmation-sensitive binders (FIG. 3B), Region III binders (FIG. 3C) and Region II binders (FIG. 3D). The binding of rabbit mAbs to cell surface mesothelin was detected by a goat anti-rabbit IgG PE conjugate.
Figure 3B:
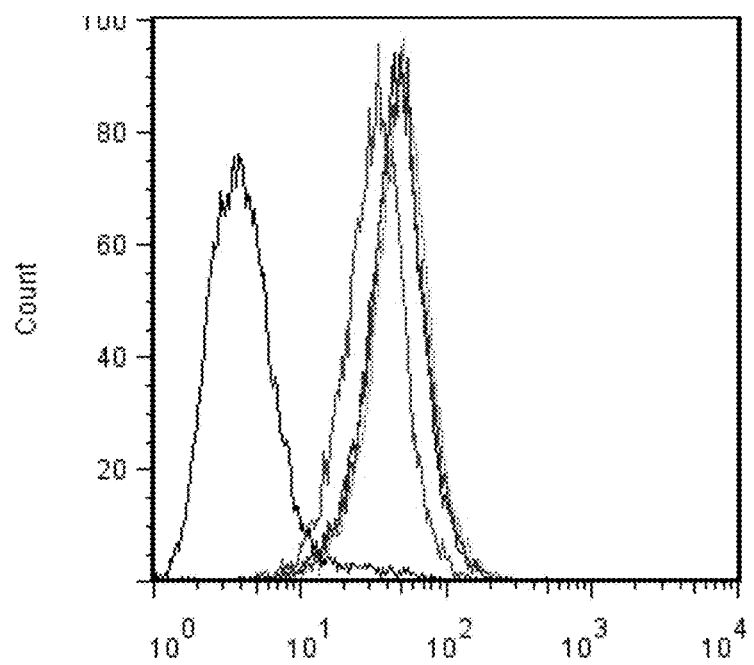
Figure 3C:
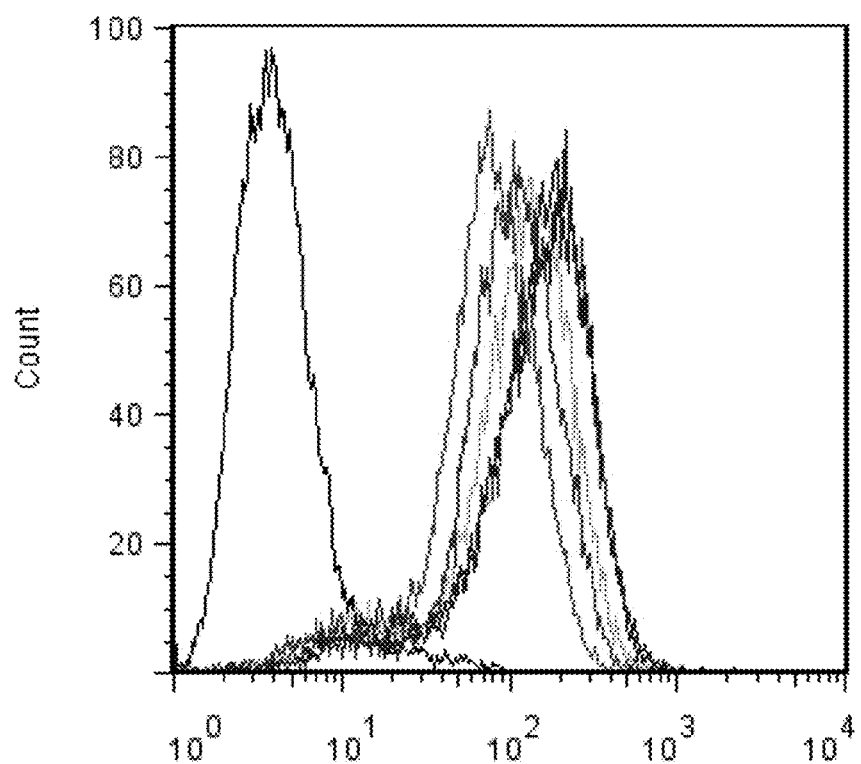
Figure 3D:
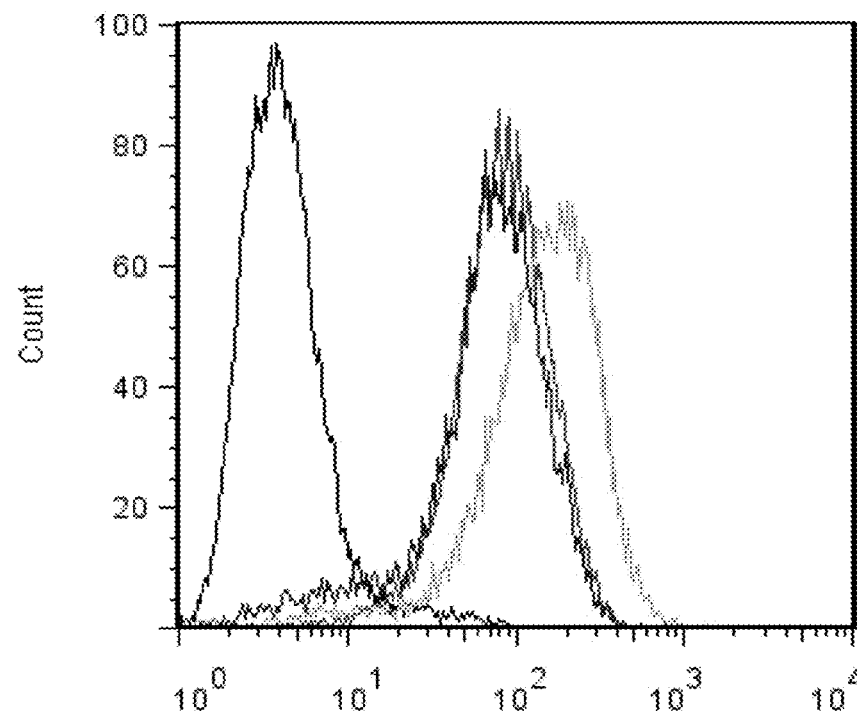

The nucleic and amino acid sequences listed in the accompanying sequence listing are shown using standard letter abbreviations for nucleotide bases, and three letter code for amino acids, as defined in 37 C.F.R. 1.822. Only one strand of each nucleic acid sequence is shown, but the complementary strand is understood as included by any reference to the displayed strand. The Sequence Listing is submitted as an ASCII text file, created on Apr. 26, 2016, 78.7 KB, which is incorporated by reference herein. In the accompanying sequence listing:

SEQ ID NO: 1 is the amino acid sequence of *Pseudomonas* exotoxin (PE).

SEQ ID NO: 2 is the amino acid sequence of PE38.
SEQ ID NO: 3 is the amino acid sequence of PE-LR.
SEQ ID NO: 4 is the amino acid sequence of PE-LR/6X.
SEQ ID NO: 5 is the amino acid sequence of PE with reduced immunogenicity.
SEQ ID NO: 6 is the amino acid sequence of PE-LR/8M.
SEQ ID NO: 7 is the amino acid sequence of human mesothelin.
SEQ ID NO: 8 is the nucleotide sequence of the YP223 VH domain.
SEQ ID NO: 9 is the amino acid sequence of the YP223 VH domain.
SEQ ID NO: 10 is the nucleotide sequence of the YP223 VL domain.
SEQ ID NO: 11 is the amino acid sequence of the YP223 VL domain.
SEQ ID NO: 12 is the nucleotide sequence of the YP218 VH domain.
SEQ ID NO: 13 is the amino acid sequence of the YP218 VH domain.
SEQ ID NO: 14 is the nucleotide sequence of the YP218 VL domain.
SEQ ID NO: 15 is the amino acid sequence of the YP218 VL domain.
SEQ ID NO: 16 is the nucleotide sequence of the YP3 VH domain.
SEQ ID NO: 17 is the amino acid sequence of the YP3 VH domain.
SEQ ID NO: 18 is the nucleotide sequence of the YP3 VL domain.
SEQ ID NO: 19 is the amino acid sequence of the YP3 VL domain.
SEQ ID NO: 20 is the nucleotide sequence of the YP187 clone 1 VH domain.
SEQ ID NO: 21 is the amino acid sequence of the YP187 clone 1 VH domain.
SEQ ID NO: 22 is the nucleotide sequence of the YP187 VL domain.
SEQ ID NO: 23 is the amino acid sequence of the YP187 VL domain.
SEQ ID NO: 24 is the nucleotide sequence of the YP158 VH domain.
SEQ ID NO: 25 is the amino acid sequence of the YP158 VH domain.
SEQ ID NO: 26 is the nucleotide sequence of the YP158 VL domain.
SEQ ID NO: 27 is the amino acid sequence of the YP158 VL domain.
SEQ ID NO: 28 is the nucleotide sequence of the YP187 clone 2 VH domain.
SEQ ID NO: 29 is the amino acid sequence of the YP187 clone 2 VH domain.
SEQ ID NO: 30 is the nucleotide sequence of the YP218scFv-PE38 immunotoxin.
SEQ ID NO: 31 is the amino acid sequence of the YP218scFv-PE38 immunotoxin.
SEQ ID NO: 32 is the nucleotide sequence of the humanized YP218scFv-PE38 immunotoxin.
SEQ ID NO: 33 is the amino acid sequence of the humanized YP218scFv-PE38 immunotoxin.
SEQ ID NO: 34 is the nucleotide sequence of the YP223scFv-PE38 immunotoxin.
SEQ ID NO: 35 is the amino acid sequence of the YP223scFv-PE38 immunotoxin.
SEQ ID NO: 36 is the nucleotide sequence of the YP3scFv-PE38 immunotoxin.
SEQ ID NO: 37 is the amino acid sequence of the YP3scFv-PE38 immunotoxin.
SEQ ID NO: 38 is the nucleotide sequence of the YP187scFv-PE38 immunotoxin.
SEQ ID NO: 39 is the amino acid sequence of the YP187scFv-PE38 immunotoxin.

DETAILED DESCRIPTION

I. Abbreviations

CAR chimeric antigen receptor
CDR complementarity determining region
CTL cytotoxic T lymphocyte
ELISA enzyme-linked immunosorbent assay
EM effector molecule
FACS fluorescence activated cell sorting
GPI glycosylphosphatidylinositol
HRP horseradish peroxidase
Ig immunoglobulin
Kd dissociation constant
mAb monoclonal antibody
PE *Pseudomonas* exotoxin
PE phycoerythrin
VH variable heavy
VL variable light II. Terms and Methods Unless otherwise noted, technical terms are used according to conventional usage. Definitions of common terms in molecular biology may be found in Benjamin Lewin, *Genes V*, published by Oxford University Press, 1994 (ISBN 0-19-854287-9); Kendrew et al. (eds.), *The Encyclopedia of Molecular Biology*, published by Blackwell Science Ltd., 1994 (ISBN 0-632-02182-9); and Robert A. Meyers (ed.), *Molecular Biology and Biotechnology: a Comprehensive Desk Reference*, published by VCH Publishers, Inc., 1995 (ISBN 1-56081-569-8).

In order to facilitate review of the various embodiments of the disclosure, the following explanations of specific terms are provided:

Antibody: A polypeptide ligand comprising at least a light chain or heavy chain immunoglobulin variable region which recognizes and binds (such as specifically recognizes and specifically binds) an epitope of an antigen, such as mesothelin, or a fragment thereof. Immunoglobulin molecules are composed of a heavy and a light chain, each of which has a variable region, termed the variable heavy ($V_H$) region and the variable light ($V_L$) region. Together, the $V_H$ region and the $V_L$ region are responsible for binding the antigen recognized by the antibody.

Antibodies include intact immunoglobulins and the variants and portions of antibodies well known in the art, such as single-domain antibodies (e.g. VH domain antibodies), Fab fragments, Fab' fragments, F(ab)'$_2$ fragments, single chain Fv proteins ("scFv"), and disulfide stabilized Fv proteins ("dsFv"). A scFv protein is a fusion protein in which a light chain variable region of an immunoglobulin and a heavy chain variable region of an immunoglobulin are bound by a linker, while in dsFvs, the chains have been mutated to introduce a disulfide bond to stabilize the association of the chains. The term "antibody" also includes genetically engineered forms such as chimeric antibodies (for example, humanized murine antibodies) and heteroconjugate antibodies (such as bispecific antibodies). See also, *Pierce Catalog and Handbook*, 1994-1995 (Pierce Chemical Co., Rockford, Ill.); Kuby, J., Immunology, 3' Ed., W. H. Freeman & Co., New York, 1997.

Typically, a naturally occurring immunoglobulin has heavy (H) chains and light (L) chains interconnected by disulfide bonds. There are two types of light chain, lambda (λ) and kappa (κ). There are five main heavy chain classes (or isotypes) which determine the functional activity of an antibody molecule: IgM, IgD, IgG, IgA and IgE.

Each heavy and light chain contains a constant region and a variable region, (the regions are also known as "domains"). In combination, the heavy and the light chain variable regions specifically bind the antigen. Light and heavy chain variable regions contain a "framework" region interrupted by three hypervariable regions, also called "complementarity-determining regions" or "CDRs." The extent of the framework region and CDRs has been defined according to Kabat et al. (see, Kabat et al., *Sequences of Proteins of Immunological Interest*, U.S. Department of Health and Human Services, 1991) and the ImMunoGeneTics database (IMGT) (see, Lefranc, *Nucleic Acids Res* 29:207-9, 2001). The Kabat database is maintained online. The sequences of the framework regions of different light or heavy chains are relatively conserved within a species, such as humans. The framework region of an antibody, that is the combined framework regions of the constituent light and heavy chains, serves to position and align the CDRs in three-dimensional space.

The CDRs are primarily responsible for binding to an epitope of an antigen. The CDRs of each chain are typically referred to as CDR1, CDR2, and CDR3, numbered sequentially starting from the N-terminus, and are often identified by the chain in which the particular CDR is located. Thus, a $V_H$ CDR3 (or H-CDR3) is located in the variable domain of the heavy chain of the antibody in which it is found, whereas a $V_L$ CDR1 (or L-CDR1) is the CDR1 from the variable domain of the light chain of the antibody in which it is found. An antibody that binds mesothelin, for example, will have a specific $V_H$ region and the $V_L$ region sequence, and thus specific CDR sequences. Antibodies with different specificities (i.e. different combining sites for different antigens) have different CDRs. Although it is the CDRs that vary from antibody to antibody, only a limited number of amino acid positions within the CDRs are directly involved in antigen binding. These positions within the CDRs are called specificity determining residues (SDRs).

References to "$V_H$" or "VH" refer to the variable region of an immunoglobulin heavy chain, including that of an Fv, scFv, dsFv or Fab. References to "$V_L$" or "VL" refer to the variable region of an immunoglobulin light chain, including that of an Fv, scFv, dsFv or Fab.

A "monoclonal antibody" is an antibody produced by a single clone of B-lymphocytes or by a cell into which the light and/or heavy chain genes of a single antibody have been transfected. Monoclonal antibodies are produced by methods known to those of skill in the art, for instance by making hybrid antibody-forming cells from a fusion of myeloma cells with immune spleen cells. Monoclonal antibodies include humanized monoclonal antibodies.

A "chimeric antibody" contains structural elements from two or more different antibody molecules, often from different animal species. For example, a chimeric antibody can have framework residues from one species, such as human, and CDRs (which generally confer antigen binding) from another species, such as a murine antibody that specifically binds mesothelin.

A "human" antibody (also called a "fully human" antibody) is an antibody that includes human framework regions and all of the CDRs from a human immunoglobulin. In one example, the framework and the CDRs are from the same originating human heavy and/or light chain amino acid sequence. However, frameworks from one human antibody can be engineered to include CDRs from a different human antibody. A "humanized" immunoglobulin is an immunoglobulin including a human framework region and one or more CDRs from a non-human (for example a mouse, rabbit, rat, or synthetic) immunoglobulin. The non-human immunoglobulin providing the CDRs is termed a "donor," and the human immunoglobulin providing the framework is termed an "acceptor." In one embodiment, all the CDRs are from the donor immunoglobulin in a humanized immunoglobulin. Constant regions need not be present, but if they are, they must be substantially identical to human immunoglobulin constant regions, i.e., at least about 85-90%, such as about 95% or more identical. Hence, all parts of a humanized immunoglobulin, except possibly the CDRs, are substantially identical to corresponding parts of natural human immunoglobulin sequences. A "humanized antibody" is an antibody comprising a humanized light chain and a humanized heavy chain immunoglobulin. A humanized antibody binds to the same antigen as the donor antibody that provides the CDRs. The acceptor framework of a humanized immunoglobulin or antibody may have a limited number of substitutions by amino acids taken from the donor framework. Humanized or other monoclonal antibodies can have additional conservative amino acid substitutions which have substantially no effect on antigen binding or other immunoglobulin functions. Humanized immunoglobulins can be constructed by means of genetic engineering (see for example, U.S. Pat. No. 5,585,089).

Binding affinity: Affinity of an antibody for an antigen. In one embodiment, affinity is calculated by a modification of the Scatchard method described by Frankel et al. (*Mol. Immunol.*, 16:101-106, 1979). In another embodiment, binding affinity is measured by an antigen/antibody dissociation rate. In another embodiment, a high binding affinity is measured by a competition radioimmunoassay. In another embodiment, binding affinity is measured by ELISA. An antibody that "specifically binds" an antigen (such as mesothelin) is an antibody that binds the antigen with high affinity and does not significantly bind other unrelated antigens.

Chemotherapeutic agent: Any chemical agent with therapeutic usefulness in the treatment of diseases characterized by abnormal cell growth. Such diseases include tumors, neoplasms, and cancer as well as diseases characterized by hyperplastic growth such as psoriasis. In one embodiment, a chemotherapeutic agent is an agent of use in treating mesothelioma or another tumor, such as stomach cancer, squamous cell carcinomas, prostate cancer, pancreatic cancer, lung cancer, cholangiocarcinoma, breast cancer or ovarian cancer. In one embodiment, a chemotherapeutic agent is a radioactive compound. One of skill in the art can readily identify a chemotherapeutic agent of use (see for example, Slapak and Kufe, *Principles of Cancer Therapy*, Chapter 86 in *Harrison's Principles of Internal Medicine*, 14th edition; Perry et al., Chemotherapy, Ch. 17 in Abeloff, Clinical Oncology $2^{nd}$ ed., © 2000 Churchill Livingstone, Inc; Baltzer, L., Berkery, R. (eds.): Oncology Pocket Guide to Chemotherapy, 2nd ed. St. Louis, Mosby-Year Book, 1995; Fischer, D. S., Knobf, M. F., Durivage, H. J. (eds): *The Cancer Chemotherapy Handbook*, 4th ed. St. Louis, Mosby-Year Book, 1993). Combination chemotherapy is the administration of more than one agent to treat cancer. One example is the administration of an antibody (or immunoconjugate) that binds mesothelin used in combination with a radioactive or chemical compound.

Cholangiocarcinoma: A type of cancer that develops in cells that line the bile ducts in the liver.

Conservative variant: "Conservative" amino acid substitutions are those substitutions that do not substantially affect or decrease the affinity of a protein, such as an antibody to mesothelin. For example, a monoclonal antibody that specifically binds mesothelin can include at most about 1, at most about 2, at most about 5, at most about 10, or at most about 15 conservative substitutions and specifically bind a mesothelin polypeptide. The term "conservative variant" also includes the use of a substituted amino acid in place of an unsubstituted parent amino acid, provided that antibody specifically binds mesothelin. Non-conservative substitutions are those that reduce an activity or binding to mesothelin.

Conservative amino acid substitution tables providing functionally similar amino acids are well known to one of ordinary skill in the art. The following six groups are examples of amino acids that are considered to be conservative substitutions for one another:

1) Alanine (A), Serine (S), Threonine (T);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V); and
6) Phenylalanine (F), Tyrosine (Y), Tryptophan (W).

Complementarity determining region (CDR): Amino acid sequences which together define the binding affinity and specificity of the natural Fv region of a native Ig binding site. The light and heavy chains of an Ig each have three CDRs, designated L-CDR1, L-CDR2, L-CDR3 and H-CDR1, H-CDR2, H-CDR3, respectively.

Contacting: Placement in direct physical association; includes both in solid and liquid form.

Cytotoxicity: The toxicity of a molecule, such as an immunotoxin, to the cells intended to be targeted, as opposed to the cells of the rest of an organism. In one embodiment, in contrast, the term "toxicity" refers to toxicity of an immunotoxin to cells other than those that are the cells intended to be targeted by the targeting moiety of the immunotoxin, and the term "animal toxicity" refers to toxicity of the immunotoxin to an animal by toxicity of the immunotoxin to cells other than those intended to be targeted by the immunotoxin.

Degenerate variant: In the context of the present disclosure, a "degenerate variant" refers to a polynucleotide encoding a mesothelin polypeptide or an antibody that binds mesothelin that includes a sequence that is degenerate as a result of the genetic code. There are 20 natural amino acids, most of which are specified by more than one codon. Therefore, all degenerate nucleotide sequences are included as long as the amino acid sequence of the mesothelin polypeptide or antibody that binds mesothelin encoded by the nucleotide sequence is unchanged.

Diagnostic: Identifying the presence or nature of a pathologic condition, such as, but not limited to, cancer. Diagnostic methods differ in their sensitivity and specificity. The "sensitivity" of a diagnostic assay is the percentage of diseased individuals who test positive (percent of true positives). The "specificity" of a diagnostic assay is one minus the false positive rate, where the false positive rate is defined as the proportion of those without the disease who test positive. While a particular diagnostic method may not provide a definitive diagnosis of a condition, it suffices if the method provides a positive indication that aids in diagnosis. "Prognostic" is the probability of development (e.g., severity) of a pathologic condition, such as cancer or metastasis.

Effector molecule: The portion of a chimeric molecule that is intended to have a desired effect on a cell to which the chimeric molecule is targeted. Effector molecule is also known as an effector moiety (EM), therapeutic agent, or diagnostic agent, or similar terms.

Therapeutic agents include such compounds as nucleic acids, proteins, peptides, amino acids or derivatives, glycoproteins, radioisotopes, lipids, carbohydrates, or recombinant viruses. Nucleic acid therapeutic and diagnostic moieties include antisense nucleic acids, derivatized oligonucleotides for covalent cross-linking with single or duplex DNA, and triplex forming oligonucleotides. Alternatively, the molecule linked to a targeting moiety, such as an anti-mesothelin antibody, may be an encapsulation system, such as a liposome or micelle that contains a therapeutic composition such as a drug, a nucleic acid (such as an antisense nucleic acid), or another therapeutic moiety that can be shielded from direct exposure to the circulatory system. Means of preparing liposomes attached to antibodies are well known to those of skill in the art (see, for example, U.S. Pat. No. 4,957,735; and Connor et al., *Pharm Ther* 28:341-365, 1985). Diagnostic agents or moieties include radioisotopes and other detectable labels. Detectable labels useful for such purposes are also well known in the art, and include radioactive isotopes such as $^{35}$S, $^{13}$C, $^{13}$N, $^{15}$O, $^{18}$F, $^{19}$F, $^{99m}$Tc, $^{131}$I, $^{3}$H, $^{14}$C, $^{15}$N, $^{90}$Y, $^{99}$Tc, $^{111}$In and $^{125}$I, fluorophores, chemiluminescent agents, and enzymes.

Epitope: An antigenic determinant. These are particular chemical groups or peptide sequences on a molecule that are antigenic, i.e. that elicit a specific immune response. An antibody specifically binds a particular antigenic epitope on a polypeptide, such as mesothelin.

Framework region: Amino acid sequences interposed between CDRs. Framework regions include variable light and variable heavy framework regions. The framework regions serve to hold the CDRs in an appropriate orientation for antigen binding.

Host cells: Cells in which a vector can be propagated and its DNA expressed. The cell may be prokaryotic or eukaryotic. The term also includes any progeny of the subject host cell. It is understood that all progeny may not be identical to the parental cell since there may be mutations that occur during replication. However, such progeny are included when the term "host cell" is used.

Hybridoma: A hybrid cell for the production of monoclonal antibodies. A hybridoma is produced by fusion of an antibody-producing cell (such as a B cell obtained from an immunized animal, for example a mouse, rat or rabbit) and a myeloma cell.

Immune response: A response of a cell of the immune system, such as a B cell, T cell, or monocyte, to a stimulus. In one embodiment, the response is specific for a particular antigen (an "antigen-specific response"). In one embodiment, an immune response is a T cell response, such as a CD4$^+$ response or a CD8$^+$ response. In another embodiment, the response is a B cell response, and results in the production of specific antibodies.

Immunoconjugate: A covalent linkage of an effector molecule to an antibody or functional fragment thereof. The effector molecule can be a detectable label or an immunotoxin. Specific, non-limiting examples of toxins include, but are not limited to, abrin, ricin, *Pseudomonas* exotoxin (PE, such as PE35, PE37, PE38, and PE40), diphtheria toxin (DT), botulinum toxin, or modified toxins thereof, or other toxic agents that directly or indirectly inhibit cell growth or kill cells. For example, PE and DT are highly toxic compounds that typically bring about death through liver toxicity. PE and DT, however, can be modified into a form for use as an immunotoxin by removing the native targeting component of the toxin (such as the domain Ia of PE and the B chain of DT) and replacing it with a different targeting moiety, such as an antibody. A "chimeric molecule" is a targeting moiety, such as a ligand or an antibody, conjugated (coupled) to an effector molecule. The term "conjugated" or "linked" refers to making two polypeptides into one contiguous polypeptide molecule. In one embodiment, an antibody is joined to an effector molecule. In another embodiment, an antibody joined to an effector molecule is further joined to a lipid or other molecule to a protein or peptide to increase its half-life in the body. The linkage can be either by chemical or recombinant means. In one embodiment, the linkage is chemical, wherein a reaction between the antibody moiety and the effector molecule has produced a covalent bond formed between the two molecules to form one molecule. A peptide linker (short peptide sequence) can optionally be included between the antibody and the effector molecule. Because immunoconjugates were originally prepared from two molecules with separate functionalities, such as an antibody and an effector molecule, they are also sometimes referred to as "chimeric molecules." The term "chimeric molecule," as used herein, therefore refers to a targeting moiety, such as a ligand or an antibody, conjugated (coupled) to an effector molecule.

Isolated: An "isolated" biological component, such as a nucleic acid, protein (including antibodies) or organelle, has been substantially separated or purified away from other biological components in the environment (such as a cell) in which the component naturally occurs, i.e., other chromosomal and extra-chromosomal DNA and RNA, proteins and organelles. Nucleic acids and proteins that have been "isolated" include nucleic acids and proteins purified by standard purification methods. The term also embraces nucleic acids and proteins prepared by recombinant expression in a host cell as well as chemically synthesized nucleic acids.

Label: A detectable compound or composition that is conjugated directly or indirectly to another molecule, such as an antibody or a protein, to facilitate detection of that molecule. Specific, non-limiting examples of labels include fluorescent tags, enzymatic linkages, and radioactive isotopes. In one example, a "labeled antibody" refers to incorporation of another molecule in the antibody. For example, the label is a detectable marker, such as the incorporation of a radiolabeled amino acid or attachment to a polypeptide of biotinyl moieties that can be detected by marked avidin (for example, streptavidin containing a fluorescent marker or enzymatic activity that can be detected by optical or colorimetric methods). Various methods of labeling polypeptides and glycoproteins are known in the art and may be used. Examples of labels for polypeptides include, but are not limited to, the following: radioisotopes or radionucleotides (such as $^{35}S$, $^{13}C$, $^{13}N$, $^{15}O$, $^{18}F$, $^{19}F$, $^{99m}Tc$, $^{131}I$, $^{3}H$, $^{14}C$, $^{15}N$, $^{90}Y$, $^{99}Tc$, $^{111}In$ and $^{125}I$), fluorescent labels (such as fluorescein isothiocyanate (FITC), rhodamine, lanthanide phosphors), enzymatic labels (such as horseradish peroxidase, beta-galactosidase, luciferase, alkaline phosphatase), chemiluminescent markers, biotinyl groups, predetermined polypeptide epitopes recognized by a secondary reporter (such as a leucine zipper pair sequences, binding sites for secondary antibodies, metal binding domains, epitope tags), or magnetic agents, such as gadolinium chelates. In some embodiments, labels are attached by spacer arms of various lengths to reduce potential steric hindrance.

Linker: In some cases, a linker is a peptide within an antibody binding fragment (such as an Fv fragment) which serves to indirectly bond the variable heavy chain to the variable light chain. "Linker" can also refer to a peptide serving to link a targeting moiety, such as an antibody, to an effector molecule, such as a cytotoxin or a detectable label.

The terms "conjugating," "joining," "bonding" or "linking" refer to making two polypeptides into one contiguous polypeptide molecule, or to covalently attaching a radionuclide or other molecule to a polypeptide, such as an scFv. In the specific context, the terms include reference to joining a ligand, such as an antibody moiety, to an effector molecule. The linkage can be either by chemical or recombinant means. "Chemical means" refers to a reaction between the antibody moiety and the effector molecule such that there is a covalent bond formed between the two molecules to form one molecule.

Lung cancer: Cancer that forms in tissues of the lung, usually in the cells lining air passages. The two main types are small cell lung cancer and non-small cell lung cancer. These types are diagnosed based on how the cells look under a microscope.

Mammal: This term includes both human and non-human mammals. Similarly, the term "subject" includes both human and veterinary subjects.

Mesothelin: A 40 kDa cell-surface glycosylphosphatidylinositol (GPI)-linked glycoprotein. The human mesothelin protein is synthesized as a 69 kD precursor which is then proteolytically processed. The 30 kD amino terminus of mesothelin is secreted and is referred to as megakaryocyte potentiating factor (Yamaguchi et al., *J. Biol. Chem.* 269:805 808, 1994). The 40 kD carboxyl terminus remains bound to the membrane as mature mesothelin (Chang et al., Natl. *Acad. Sci.* USA 93:136 140, 1996). Exemplary nucleic acid and amino acid sequences of mesothelin are as described in PCT Publication No. WO 97/25,068; U.S. Pat. No. 6,083, 502; Chang and Pastan, *Int. J. Cancer* 57:90, 1994; Chang and Pastan, *Proc. Natl. Acad. Sci USA* 93:136, 1996; Brinkmann et al., *Int. J. Cancer* 71:638, 1997; and Chowdhury et al., *Mol. Immunol.* 34:9, 1997. The amino acid sequence of human mesothelin is set forth herein as SEQ ID NO: 7. Mesothelin also refers to mesothelin proteins or polypeptides which remain intracellular as well as secreted and/or isolated extracellular mesothelin protein.

Mesothelioma: A type of neoplasm derived from the lining cells of the pleura and peritoneum which grows as a thick sheet covering the viscera, and is composed of spindle cells or fibrous tissue which may enclose gland-like spaces lined by cuboidal cells. Mesotheliomas often originate in the tissue lining the lung, heart or abdomen. In some cases, mesotheliomas are caused by exposure to asbestos.

MORAb-009: A chimeric (mouse/human) monoclonal IgG/K with high affinity and specificity for mesothelin. The VH and VL regions of mouse anti-mesothelin scFv were obtained by panning a phage display library made from splenic mRNA of a mouse immunized with mesothelin cDNA on mesothelin-positive cells. The VH and VL regions were grafted in frame with human IgG1 and kappa constant regions (Hassan and Ho, *Eur J Cancer* 44(1):46-53, 2008).

Neoplasia, malignancy, cancer or tumor: A neoplasm is an abnormal growth of tissue or cells that results from excessive cell division. Neoplastic growth can produce a tumor. The amount of a tumor in an individual is the "tumor burden" which can be measured as the number, volume, or weight of the tumor. A tumor that does not metastasize is referred to as "benign." A tumor that invades the surrounding tissue and/or can metastasize is referred to as "malignant." Examples of hematological tumors include leukemias, including acute leukemias (such as acute lymphocytic leukemia, acute myelocytic leukemia, acute myelogenous leukemia and myeloblastic, promyelocytic, myelomonocytic, monocytic and erythroleukemia), chronic leukemias (such as chronic myelocytic (granulocytic) leukemia, chronic myelogenous leukemia, and chronic lymphocytic leukemia), polycythemia vera, lymphoma, Hodgkin's disease, non-Hodgkin's lymphoma (indolent and high grade forms), multiple myeloma, Waldenstrom's macroglobulinemia, heavy chain disease, myelodysplastic syndrome, hairy cell leukemia and myelodysplasia.

Examples of solid tumors, such as sarcomas and carcinomas, include fibrosarcoma, myxosarcoma, liposarcoma, chondrosarcoma, osteogenic sarcoma, and other sarcomas, synovioma, mesothelioma, cholangiocarcinoma, Ewing's tumor, leiomyosarcoma, rhabdomyosarcoma, colon carcinoma, lymphoid malignancy, pancreatic cancer, breast cancer, lung cancers, ovarian cancer, prostate cancer, hepatocellular carcinoma, squamous cell carcinoma, basal cell carcinoma, adenocarcinoma, sweat gland carcinoma, medullary thyroid carcinoma, papillary thyroid carcinoma, pheochromocytomas sebaceous gland carcinoma, papillary carcinoma, papillary adenocarcinomas, medullary carcinoma, bronchogenic carcinoma, renal cell carcinoma, hepatoma, bile duct carcinoma, choriocarcinoma, Wilms' tumor, cervical cancer, testicular tumor, seminoma, bladder carcinoma, and CNS tumors (such as a glioma, astrocytoma, medulloblastoma, craniopharyogioma, ependymoma, pinealoma, hemangioblastoma, acoustic neuroma, oligodendroglioma, menangioma, melanoma, neuroblastoma and retinoblastoma).

In several examples, the caner is mesothelioma, stomach cancer, squamous cell carcinomas, prostate cancer, pancreatic cancer, lung cancer, cholangiocarcinoma, breast cancer or ovarian cancer.

Operably linked: A first nucleic acid sequence is operably linked with a second nucleic acid sequence when the first nucleic acid sequence is placed in a functional relationship with the second nucleic acid sequence. For instance, a promoter, such as the CMV promoter, is operably linked to a coding sequence if the promoter affects the transcription or expression of the coding sequence. Generally, operably linked DNA sequences are contiguous and, where necessary to join two protein-coding regions, in the same reading frame.

Ovarian cancer: Cancer that forms in tissues of the ovary (one of a pair of female reproductive glands in which the ova, or eggs, are formed). Most ovarian cancers are either ovarian epithelial carcinomas (cancer that begins in the cells on the surface of the ovary) or malignant germ cell tumors (cancer that begins in egg cells).

Pancreatic cancer: A disease in which malignant (cancer) cells are found in the tissues of the pancreas. Also called exocrine cancer.

Pharmaceutical agent: A chemical compound or composition capable of inducing a desired therapeutic or prophylactic effect when properly administered to a subject or a cell.

Pharmaceutically acceptable carriers: The pharmaceutically acceptable carriers of use are conventional. *Remington's Pharmaceutical Sciences*, by E. W. Martin, Mack Publishing Co., Easton, Pa., 15th Edition, 1975, describes compositions and formulations suitable for pharmaceutical delivery of the antibodies disclosed herein.

In general, the nature of the carrier will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. For solid compositions (such as powder, pill, tablet, or capsule forms), conventional non-toxic solid carriers can include, for example, pharmaceutical grades of mannitol, lactose, starch, or magnesium stearate. In addition to biologically neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

Preventing, treating or ameliorating a disease: "Preventing" a disease refers to inhibiting the full development of a disease. "Treating" refers to a therapeutic intervention that ameliorates a sign or symptom of a disease or pathological condition after it has begun to develop, such as a reduction in tumor burden or a decrease in the number of size of metastases. "Ameliorating" refers to the reduction in the number or severity of signs or symptoms of a disease, such as cancer.

Prostate cancer: Cancer that forms in tissues of the prostate (a gland in the male reproductive system found below the bladder and in front of the rectum). Prostate cancer usually occurs in older men.

Purified: The term purified does not require absolute purity; rather, it is intended as a relative term. Thus, for example, a purified peptide preparation is one in which the peptide or protein is more enriched than the peptide or protein is in its natural environment within a cell. In one embodiment, a preparation is purified such that the protein or peptide represents at least 50% of the total peptide or protein content of the preparation. Substantial purification denotes purification from other proteins or cellular components. A substantially purified protein is at least 60%, 70%, 80%, 90%, 95% or 98% pure. Thus, in one specific, non-limiting example, a substantially purified protein is 90% free of other proteins or cellular components.

Recombinant: A recombinant nucleic acid is one that has a sequence that is not naturally occurring or has a sequence that is made by an artificial combination of two otherwise separated segments of sequence. This artificial combination is often accomplished by chemical synthesis or by the artificial manipulation of isolated segments of nucleic acids, for example, by genetic engineering techniques.

Recombinant toxins: Chimeric proteins in which a cell targeting moiety is fused to a toxin (Pastan et al., *Science*, 254:1173-1177, 1991). If the cell targeting moiety is the Fv portion of an antibody, the molecule is termed a recombinant immunotoxin (Chaudhary et al., *Nature*, 339:394-397, 1989). The toxin moiety is genetically altered so that it cannot bind to the toxin receptor present on most normal cells. Recombinant immunotoxins selectively kill cells which are recognized by the antigen binding domain. These recombinant toxins and immunotoxins can be used to treat cancer, for example, a cancer in which mesothelin is expressed.

Sample (or biological sample): A biological specimen containing genomic DNA, RNA (including mRNA), protein, or combinations thereof, obtained from a subject. Examples include, but are not limited to, peripheral blood, tissue, cells, urine, saliva, tissue biopsy, fine needle aspirate, surgical specimen, and autopsy material. In one example, a sample includes a tumor biopsy, such as a tumor biopsy.

Sequence identity: The similarity between amino acid or nucleic acid sequences is expressed in terms of the similarity between the sequences, otherwise referred to as sequence identity. Sequence identity is frequently measured in terms of percentage identity (or similarity or homology); the higher the percentage, the more similar the two sequences are. Homologs or variants of a polypeptide or nucleic acid molecule will possess a relatively high degree of sequence identity when aligned using standard methods.

Methods of alignment of sequences for comparison are well known in the art. Various programs and alignment algorithms are described in: Smith and Waterman, *Adv. Appl. Math.* 2:482, 1981; Needleman and Wunsch, *J. Mol. Biol.* 48:443, 1970; Pearson and Lipman, *Proc. Natl. Acad. Sci. U.S.A.* 85:2444, 1988; Higgins and Sharp, *Gene* 73:237, 1988; Higgins and Sharp, *CABIOS* 5:151, 1989; Corpet et al., *Nucleic Acids Research* 16:10881, 1988; and Pearson and Lipman, *Proc. Natl. Acad. Sci. U.S.A.* 85:2444, 1988. Altschul et al., *Nature Genet.* 6:119, 1994, presents a detailed consideration of sequence alignment methods and homology calculations.

The NCBI Basic Local Alignment Search Tool (BLAST) (Altschul et al., *J. Mol. Biol.* 215:403, 1990) is available from several sources, including the National Center for Biotechnology Information (NCBI, Bethesda, Md.) and on the internet, for use in connection with the sequence analysis programs blastp, blastn, blastx, tblastn and tblastx. A description of how to determine sequence identity using this program is available on the NCBI website on the internet.

Homologs and variants of a $V_L$ or a $V_H$ of an antibody that specifically binds mesothelin or a fragment thereof are typically characterized by possession of at least about 75%, for example at least about 80%, 90%, 95%, 96%, 97%, 98% or 99% sequence identity counted over the full length alignment with the amino acid sequence of the antibody using the NCBI Blast 2.0, gapped blastp set to default parameters. For comparisons of amino acid sequences of greater than about 30 amino acids, the Blast 2 sequences function is employed using the default BLOSUM62 matrix set to default parameters, (gap existence cost of 11, and a per residue gap cost of 1). When aligning short peptides (fewer than around 30 amino acids), the alignment should be performed using the Blast 2 sequences function, employing the PAM30 matrix set to default parameters (open gap 9, extension gap 1 penalties). Proteins with even greater similarity to the reference sequences will show increasing percentage identities when assessed by this method, such as at least 80%, at least 85%, at least 90%, at least 95%, at least 98%, or at least 99% sequence identity. When less than the entire sequence is being compared for sequence identity, homologs and variants will typically possess at least 80% sequence identity over short windows of 10-20 amino acids, and may possess sequence identities of at least 85% or at least 90% or 95% depending on their similarity to the reference sequence. Methods for determining sequence identity over such short windows are available at the NCBI website on the internet. One of skill in the art will appreciate that these sequence identity ranges are provided for guidance only; it is entirely possible that strongly significant homologs could be obtained that fall outside of the ranges provided.

Squamous cell carcinoma: A malignant neoplasm derived from stratified squamous epithelium, but which may also occur in sites such as bronchial mucosa where glandular or columnar epithelium is normally present. Squamous cell carcinoma is the most common type of skin cancer.

SS1P: A recombinant immunotoxin consisting of an anti-mesothelin Fv (the same Fv as MORAb-009) linked to a truncated *Pseudomonas* exotoxin that mediates cell killing (Chowdhury and Pastan, *Nat Biotechnol* 17:568-572, 1999; Pastan et al., *Nat Rev Cancer* 6:559-565, 2006). SS1P, also known as CAT-5001, is cytotoxic to cell lines expressing mesothelin, causes complete regression of mesothelin expressing tumor xenografts in nude mice, and is cytotoxic to cells obtained from human cancer patients (Hassan et al., *Clin Cancer Res* 10:3937-3942, 2001; Hassan et al., *Clin Cancer Res* 8:3520-3526, 2002).

Stomach cancer: Cancer that forms in tissues lining the stomach. Also called gastric cancer.

Subject: Living multi-cellular vertebrate organisms, a category that includes both human and veterinary subjects, including human and non-human mammals.

Synthetic: Produced by artificial means in a laboratory, for example a monoclonal antibody produced by hybridoma technology or expressed from a cDNA construct.

Therapeutically effective amount: A quantity of a specific substance sufficient to achieve a desired effect in a subject being treated. For instance, this can be the amount necessary to inhibit or suppress growth of a tumor. In one embodiment, a therapeutically effective amount is the amount necessary to eliminate, reduce the size, or prevent metastasis of a tumor. When administered to a subject, a dosage will generally be used that will achieve target tissue concentrations (for example, in tumors) that has been shown to achieve a desired in vitro effect.

Toxin: A molecule that is cytotoxic for a cell. Toxins include abrin, ricin, *Pseudomonas* exotoxin (PE), diphtheria toxin (DT), botulinum toxin, saporin, restrictocin or gelonin, or modified toxins thereof. For example, PE and DT are highly toxic compounds that typically bring about death through liver toxicity. PE and DT, however, can be modified into a form for use as an immunotoxin by removing the native targeting component of the toxin (such as domain Ia of PE or the B chain of DT) and replacing it with a different targeting moiety, such as an antibody.

Vector: A nucleic acid molecule as introduced into a host cell, thereby producing a transformed host cell. A vector may include nucleic acid sequences that permit it to replicate in a host cell, such as an origin of replication. A vector may also include one or more selectable marker genes and other genetic elements known in the art.

Unless otherwise explained, all technical and scientific terms used herein have the same meaning as commonly understood by one of ordinary skill in the art to which this disclosure belongs. The singular terms "a," "an," and "the" include plural referents unless context clearly indicates otherwise. "Comprising A or B" means including A, or B, or A and B. It is further to be understood that all base sizes or amino acid sizes, and all molecular weight or molecular mass values, given for nucleic acids or polypeptides are approximate, and are provided for description. Although methods and materials similar or equivalent to those described herein can be used in the practice or testing of the present disclosure, suitable methods and materials are described below.

All publications, patent applications, patents, and other references mentioned herein are incorporated by reference in their entirety. In case of conflict, the present specification, including explanations of terms, will control. In addition, the materials, methods, and examples are illustrative only and not intended to be limiting.

III. Introduction

Monoclonal antibodies (mAbs) against mesothelin are currently being evaluated and clinically developed for the treatment of mesothelioma and several other forms of cancer. However, almost all of the existing mesothelin mAbs (including MORAb-009) currently being evaluated in pre-clinical or clinical studies recognize Region I, the highly immunogenic N-terminus of cell surface mesothelin, which also binds mucin MUC16/CA125. Autoantibodies, or soluble MUC16/CA125 proteins in patients may sequester anti-Region I mAbs, limiting their anti-cancer efficacy. In addition, when measuring soluble mesothelin for follow-up of patients in clinical trials treated with MORAb-009, the FDA-approved MesoMark™ kit fails to detect serum mesothelin because it forms a complex with MORAb-009 and the epitope of MORAb-009 overlaps that of the anti-Region I antibody used in MesoMark™. Thus, it is desirable to generate and evaluate mAbs against all of the potentially functional sub-domains of mesothelin for anti-tumor activity and diagnostic value.

Rabbit hybridoma technology and a panel of truncated mesothelin domain fragments were used to identify anti-mesothelin mAbs that specifically bind an epitope that is not part of Region I. Four rabbit mAbs (YP187, YP223, YP218 and YP3) were identified with high, subnanomolar affinity for either Region II (391-486), Region III (487-581) or a native conformation. SS1P, a recombinant immunotoxin consisting of an anti-mesothelin Fv linked to a truncated *Pseudomonas* exotoxin, does not compete with the binding of these antibodies to mesothelin in ELISA, thus these new rabbit mAbs recognize epitopes different from the MORAb-009/SS1P site. Flow cytometry analysis demonstrated that the rabbit mAbs also bind native mesothelin on cancer cells.

Immunotoxins comprising rabbit scFv YP187, YP223, YP218 or YP3 fused to PE38 were capable of binding mesothelin-expressing cells and inducing cytotoxicity. YP218scFv-PE38 exhibited the highest binding affinity, therefore the cytotoxicity of this immunotoxin was further evaluated against four mesothelioma patient primary cells and in a mouse model of mesothelioma. The results demonstrated that YP218scFv-PE38 was 2- to 5-fold more potent than SS1P against primary patient mesothelioma cells and was more effective against tumor relapse than SS1P in vivo.

Further disclosed herein is the identification of a high-affinity rabbit mAb that binds Region I of mesothelin (YP158). YP158 binds native mesothelin protein in cancer cells and tissues with very high affinity and specificity.

IV. Rabbit Monoclonal Antibodies Specific for Mesothelin

Disclosed herein is a panel of rabbit anti-mesothelin monoclonal antibodies (mAbs) that bind specific regions of mesothelin. In one aspect of the present disclosure, the rabbit mAbs bind an epitope that is not part of Region I. In particular, the identified mAbs (YP187, YP223, YP218 and YP3) bind either Region II (391-486), Region III (487-581) or a native conformation of mesothelin with subnanomolar affinity. These antibodies do not compete for binding with the mesothelin-specific immunotoxin SS1P or mesothelin-specific antibody MORAb-009. In another aspect, disclosed is a high-affinity rabbit mAb that binds Region I of mesothelin (YP158). YP158 binds native mesothelin protein in cancer cells and tissues with high affinity and specificity.

The nucleotide and amino acid sequences of the VH and VL domains of YP223, YP218, YP3, YP187 and YP158 are shown below.

YP223 VH Nucleotide Sequence
(SEQ ID NO: 8)
CAGGAGCAGCTGGAGGAGTCCGGGGGAGACCTGGTCCAGCCTGAGGGATC
CCTGACACTCACCTGCAAAGCCTCTGGGTTAGACTTCAGTAGCAGCTACT
GGATATGTTGGGTCCGCCAGGCTCCAGGGAAGGGGCTGGAGTGGATCGGG
TGTCGTCATACTTTTACTGCTAACACATGGTCCGCGAGCTGGGTGAATGG
CCCGGTTCACCATCTCCAGAAGCACCAGCCTAGGCACGGTGGATCTGAAAA
TGACCAGTCTGACAGCCGCGGACACGGCCACCTATTTCTGTGCCAGAGAT
GAATCTAATAATGATGGTTGGGATTTTAAGTTGTGGGGCCCAGGCACCCT
GGTCACCGTCTCCTCA YP223 VH Amino Acid Sequence
(SEQ ID NO: 9)
QEQLEESGGDLVQPEGSLTLTCKASGLDFSSSYWICWVRQAPGKGLEWIG
CRHTFTANTWSASWVNGRFTISRSTSLGTVDLKMTSLTAADTATYFCARD
ESNNDGWDFKLWGPGTLVTVSS YP223 VL Nucleotide Sequence
(SEQ ID NO: 10)
GCCTATGATATGACCCAGACTCCAGCCTCCGTGTCTGCAGCTGTGGGAGG
CACAGTCACCATCAAGTGCCAGGCCAGTCAGAGCATTAGTAACTACTTAG
CCTGGTATCAGCAGAAACCAGGGCAGCCTCCCAAGCTCCTGATCTACCAG
GCATCCACTCTGGCACCTGGGGTCTCATCGCGGTTCAAAGGCAGTGGATC
TGGGACAGAATTCACTCTCACCATCAGCGGCGTGGAGTGTGCCGATGCTG
CCACTTACTACTGTCAACAGGGTTATACTAGTAGTAATGTTGAGAATGTT
TTCGGCGGAGGGACCGGGGTGGTGGTC YP223 VL Amino Acid Sequence
(SEQ ID NO: 11)
AYDMTQTPASVSAAVGGTVTIKCQASQSISNYLAWYQQKPGQPPKLLIYQ
ASTLAPGVSSRFKGSGSGTEFTLTISGVECADAATYYCQQGYTSSNVENV
FGGGTGVVV

TABLE 1

Amino acid positions of the YP223 VH (SEQ ID NO: 9) CDRs and YP223 VL (SEQ ID NO: 11) CDRs

|  | H-CDR1 | H-CDR2 | H-CDR3 | L-CDR1 | L-CDR2 | L-CDR3 |
|---|---|---|---|---|---|---|
| Kabat | 31-36 | 51-67 | 100-111 | 24-34 | 50-56 | 89-100 |
| IMGT | 27-34 | 52-59 | 98-111 | 27-32 | 50-52 | 89-100 |

YP218 VH Nucleotide Sequence
(SEQ ID NO: 12)
CAGCAGCAGCTGGAGGAGTCCGGGGGAGGCCTGGTCAAGCCTGAGGGATC
CCTGACACTCACCTGCAAAGCCTCTGGATTCGACCTCGGTTTCTACTTTT
ACGCCTGTTGGGTCCGCCAGGCTCCAGGGAAGGGCCTGGAGTGGATCGCA
TGCATTTATACTGCTGGTAGTGGTAGCACGTACTACGCGAGCTGGGCGAA
AGGCCGATTCACCATCTCCAAAGCCTCGTCGACCACGGTGACTCTGCAAA
TGACCAGTCTGGCAGCCGCGGACACGGCCACCTATTTCTGTGCGAGATCT
ACTGCTAATACTAGAAGTACTTATTATCTTAACTTGTGGGGCCCAGGCAC

CCTGGTCACCGTCTCCTCA

YP218 VH Amino Acid Sequence
(SEQ ID NO: 13)
QQQLEESGGGLVKPEGSLTLTCKASGFDLGFYFYACWVRQAPGKGLEWIA
CIYTAGSGSTYYASWAKGRFTISKASSTTVTLQMTSLAAADTATYFCARS
TANTRSTYYLNLWGPGTLVTVSS YP218 VL Nucleotide Sequence
(SEQ ID NO: 14)
GACGTCGTGATGACCCAGACTCCAGCCTCCGTGTCTGAACCTGTGGGAGG
CACAGTCACCATCAAGTGCCAGGCCAGTCAGAGGATTAGTAGTTACTTAT
CCTGGTATCAGCAGAAACCAGGGCAGCGTCCCAAGCTCCTGATCTTTGGT
GCATCCACTCTGGCATCTGGGGTCCCCTCGCGGTTCAAAGGCAGTGGATC
TGGGACAGAATACACTCTCACCATCAGCGACCTGGAGTGTGCCGATGCTG
CCACTTACTACTGTCAGAGTTATGCTTATTTTGATAGTAATAATTGGCAT
GCTTTCGGCGGAGGGACCGAGGTGGTGGTC YP218 VL Amino Acid Sequence
(SEQ ID NO: 15)
DVVMTQTPASVSEPVGGTVTIKCQASQRISSYLSWYQQKPGQRPKLLIFG
ASTLASGVPSRFKGSGSGTEYTLTISDLECADAATYYCQSYAYFDSNNWH
AFGGGTEVVV

TABLE 2

Amino acid positions of the YP218 VH (SEQ ID NO: 13) CDRs and YP218 VL (SEQ ID NO: 15) CDRs

| | H-CDR1 | H-CDR2 | H-CDR3 | L-CDR1 | L-CDR2 | L-CDR3 |
|---|---|---|---|---|---|---|
| Kabat | 31-36 | 51-68 | 100-112 | 24-34 | 50-56 | 89-101 |
| IMGT | 27-34 | 52-59 | 98-112 | 27-32 | 50-52 | 89-101 |

YP3 VH Nucleotide Sequence
(SEQ ID NO: 16)
CAGGAGCAGCTGGTGGAGTCCGGGGGAGGCCTGGTCCAGCCTGGGGCATC
CCTGACACTCACCTGCACAGCCTCTGGAATCGACTTCAGTCGCTACTACA
TGTGTTGGGTCCGCCAGGCTCCAGGGAAGGGACTGGAGGGGATCGCATGT
ATTTATATTGGTGGTAGTGGTAGCACTTACTACGCGAGCTGGGCAAAGG
CCGATTCACCATCTCCAAAGCCTCGTCGACCACGGTGACTCTGCAAATGA
CCAGTCTGACAGCCGCGGACACGGCCACTTATTTCTGTGCGAGAGGGACT
AATCTTAATTATATTTTTAGGTTGTGGGGCCCAGGCACCCTGGTCACCGT
CTCCTCA YP3 VH Amino Acid Sequence
(SEQ ID NO: 17)
QEQLVESGGGLVQPGASLTLTCTASGIDFSRYYMCWVRQAPGKGLEGIAC
IYIGGSGSTYYASWAKGRFTISKASSTTVTLQMTSLTAADTATYFCARGT
NLNYIFRLWGPGTLVTVSS YP3 VL Nucleotide Sequence
(SEQ ID NO: 18)
GATGTTGTGATGACCCAGACTCCATCTCCCGTGTCTGCAGCTGTGGGAGG
CACAGTCACCATCAAGTGCCAGGCCAGTCAGAGCATTAATAATGGTTTAG CCTGGTATCAGCAGAAACCAGGGCAGCCTCCCAGGCTCCTGATCTATTCT
GCATCCAATCTGGAATCTGGGGTCCCATCGCGGTTCAAAGGCAGTGGATC
TGGGACAGAGTTCACTCTCACCATCAGCGACCTGGAGTGTGACGATGCTG
CCACTTACTATTGTCAATGTATTTGGGATGGTAATAGTTATGTTAATGCT
TTCGGCGGAGGGACCGAGGTGGTGGTC YP3 VL Amino Acid Sequence
(SEQ ID NO: 19)
DVVMTQTPSPVSAAVGGTVTIKCQASQSINNGLAWYQQKPGQPPRLLIYS
ASNLESGVPSRFKGSGSGTEFTLTISDLECDDAATYYCQCIWDGNSYVNA
FGGGTEVVV

TABLE 3

Amino acid positions of the YP3 VH (SEQ ID NO: 17) CDRs and YP3 VL (SEQ ID NO: 19) CDRs

| | H-CDR1 | H-CDR2 | H-CDR3 | L-CDR1 | L-CDR2 | L-CDR3 |
|---|---|---|---|---|---|---|
| Kabat | 31-35 | 50-67 | 99-108 | 24-34 | 50-56 | 89-100 |
| IMGT | 26-33 | 51-58 | 97-108 | 27-32 | 50-52 | 89-100 |

YP187 clone 1 VH Nucleotide Sequence
(SEQ ID NO: 20)
CAGTCGTTGGAGGAGTCCGGGGGAGACCTGGTCAAGCCTGGGGCATCCCT
GACACTCACCTGCAAAGCCTCTGGATTCGACTTCAGTAGCAATGCAATGT
GCTGGGTCCGCCAGGCTCCAGGGAAGGGGCTGGAGTGGATCGCATGCATT
TATGTTGGTGATGGCAACACATACTACGCGAGCTGGGCGAAAGGCCGATT
TACCATCTCCAAAACCTCGTCGACCACGGTGACTCTGCAAATGACCAGTC
TGACAGCCGCGGACACGGCCACCTATTTCTGTGCGAGGGGATATGCTAGT
TATGGTAGTGATTATTATTGGGACTACTTTAAGTTGTGGGGCCCA YP187 clone 1 VH Amino Acid Sequence
(SEQ ID NO: 21)
QSLEESGGDLVKPGASLTLTCKASGFDFSSNAMCWVRQAPGKGLEWIACI
YVGDGNTYYASWAKGRFTISKTSSTTVTLQMTSLTAADTATYFCARGYAS
YGSDYYWDYFKLWGP YP187 clone 2 VH Nucleotide Sequence
(SEQ ID NO: 28)
CAGGAGCAGCTGGAGGAGTCCGGGGGAGACCTGGTCAAGCCGGGGCATC
CCTGACACTCACCTGCACAGCCTCTGGATTCTCCTTCAGCAGCAGCTACT
GGATATGCTGGGTCCGCCAGGCTCCAGGGAAGGGGCTGGAGTGGATCGCA
TGCATTTATGCTGGTGATGGTGGTGCCACCTATGACGCGAGCTGGGTGAA
TGGCCGATTCTCCATCTCCAAAACCTCGTCGACCACGGTGACTCTGCAAA
TGACCAGTCTGACAGCCGCGGACACGGCCACCTATTTCTGTGCGAGAAAG
GGTGCTGCTCCTACTACTTATTACTATTTTAATTTGTGGGGCCCAGGCAC
CCTGGTCACCGTCTCCTCA YP187 clone 2 VH Amino Acid Sequence
(SEQ ID NO: 29)
QEQLEESGGDLVKPGASLTLTCTASGFSFSSSYWICWVRQAPGKGLEWIA
CIYAGDGGATYDASWVNGRFSISKTSSTTVTLQMTSLTAADTATYFCARK

```
GAAPTTYYYFNLWGPGTLVTVSS

YP187 VL Nucleotide Sequence
                                      (SEQ ID NO: 22)
GCCTATGATATGACCCAGACTCCAGCCTCCGTGTCTGCAGCTGTGGGAGG

CACAGTCACCATCAAGTGCCAGGCCAGTCAGAGCATTAGCACTGCATTAG

CCTGGTATCAGCAGAAACCAGGGCAGCCTCCCAAGGTCCTGATCTATGCT

GCATCCAATCTGGCATCTGGGGTCTCATCGCGGTTCAAAGGCAGTGGATC

TGGGACAGAGTTCACTCTCACCATCAGCGACCTGGAGTGTGCCGATGCTG

CCACTTACTATTGTCAACAGGCTGCTACCATTATTAATGTTGATAATGTT

TTCGGCGGAGGGACCGAGGTGGTGGTC

YP187 VL Amino Acid Sequence
                                      (SEQ ID NO: 23)
AYDMTQTPASVSAAVGGTVTIKCQASQSISTALAWYQQKPGQPPKVLIYA

ASNLASGVSSRFKGSGSGTEFTLTISDLECADAATYYCQQAATIINVDNV

FGGGTEVVV
```

TABLE 4A

Amino acid positions of the YP187 clone 1 VH (SEQ ID NO: 21)
CDRs and YP187 VL (SEQ ID NO: 23) CDRs

|       | H-CDR1 | H-CDR2 | H-CDR3 | L-CDR1 | L-CDR2 | L-CDR3 |
|-------|--------|--------|--------|--------|--------|--------|
| Kabat | 31-35  | 50-66  | 98-113 | 24-34  | 50-56  | 89-100 |
| IMGT  | 25-33  | 51-57  | 96-113 | 27-32  | 50-52  | 89-100 |

TABLE 4B

Amino acid positions of the YP187 clone 2 VH (SEQ ID NO: 29)

|       | H-CDR1 | H-CDR2 | H-CDR3  |
|-------|--------|--------|---------|
| Kabat | 31-36  | 51-68  | 100-112 |
| IMGT  | 26-34  | 52-60  | 98-112  |

```
YP158 VH Nucleotide Sequence
                                      (SEQ ID NO: 24)
CAGTCGTTGGAGGAGTCCGGGGGAGACCTGGTCAAGCCTGGGGCATCCCT

GACACTCACCTGCACAGCCTCTGGATTCTCCTTCAGTGGCGACTACTACA

TGTGCTGGGTCCGCCAGGCTCCAGGGAAGGGGCTGGAGTGGATCGCATGC

ATTGGTGGTGGTAGTAATACTGCCACCTACTACGCGACCTGGGCGAAAGG

CCGATTCACCATCTCCAAAACCTCGTCGACCACGGTGACTCTGCAAATGA

CCAGTCTGACAGCCGCGGACACGGCCACCTATTTCTGTGCGAGAGATCTC

GGTTTTGTTGATTATGCTTTGGAATTGTGGGGCCCAGGCACCCTGGTCAC

CGTCTCCTCA

YP158 VH Amino Acid Sequence
                                      (SEQ ID NO: 25)
QSLEESGGDLVKPGASLTLTCTASGFSFSGDYYMCWVRQAPGKGLEWIAC

IGGGSNTATYYATWAKGRFTISKTSSTTVTLQMTSLTAADTATYFCARDL

GFVDYALELWGPGTLVTVSS

YP158 VL Nucleotide Sequence
                                      (SEQ ID NO: 26)
GACATTGTGATGACCCAGACTCCAGCCTCTGTGGAGGTAGCTGTGGGAGG

CACAGTCACCATCAAGTGCCAGGCCAGTGAAAACATGTACAACTCTTTAG

CCTGGTATCAGCAGAAACCAGGGCAGCCTCCCAAGCTCCTGATCTACAGG

GCATCCACTCTGGAATCTGGGGTCCCATCGCGGTTCAAAGGCAGTGGATC

TGGGACAGAGTACACTCTCACCATCAGCGACCTGGAGTGTGCCGATGCTG

CCACTTACTACTGTCAATGTACTTTTTATAGTCATAATAATAATTATGGT

GGTGCTTTCGGCGGAGGGACCGAGGTGGTGGTC

YP158 VL Amino Acid Sequence
                                      (SEQ ID NO: 27)
DIVMTQTPASVEVAVGGTVTIKCQASENMYNSLAWYQQKPGQPPKLLIYR

ASTLESGVPSRFKGSGSGTEYTLTISDLECADAATYYCQCTFYSHNNNYG

GAFGGGTEVVV
```

TABLE 5

Amino acid positions of the YP158 VH (SEQ ID NO: 25) CDRs and
YP 158 VL (SEQ ID NO: 27) CDRs

|       | H-CDR1 | H-CDR2 | H-CDR3  | L-CDR1 | L-CDR2 | L-CDR3  |
|-------|--------|--------|---------|--------|--------|---------|
| Kabat | 30-35  | 50-67  | 99-109  | 24-34  | 50-56  | 89-102  |
| IMGT  | 25-33  | 51-59  | 97-109  | 27-32  | 50-52  | 89-102  |

Provided herein are isolated monoclonal antibodies that bind (for example, specifically bind) mesothelin, such as cell-surface or soluble mesothelin. In some embodiments, the VH domain of the antibody comprises at least a portion of the amino acid sequence set forth herein as SEQ ID NO: 9 (YP223), SEQ ID NO: 13 (YP218), SEQ ID NO: 17 (YP3), SEQ ID NO: 21 (YP187 clone 1), SEQ ID NO: 29 (YP187 clone 2) or SEQ ID NO: 25 (YP158), such as one or more (such as all three) CDR sequences from SEQ ID NO: 9, 13, 17, 21, 29 or 25, as determined by IMGT. In other embodiments, the antibodies comprise one or more (such as all three) CDR sequences from SEQ ID NO: 9, 13, 17, 21, 29 or 25, as determined using the Kabat method.

In some embodiments, the VL domain of the antibody comprises at least a portion of the amino acid sequence set forth herein as SEQ ID NO: 11 (YP223), SEQ ID NO: 15 (YP218), SEQ ID NO: 19 (YP3), SEQ ID NO: 23 (YP187) or SEQ ID NO: 27 (YP158), such as one or more (such as all three) CDR sequences from SEQ ID NO: 11, 15, 19, 23 or 27, as determined by IMGT. In other embodiments, the antibodies comprise one or more (such as all three) CDR sequences from SEQ ID NO: 11, 15, 19, 23 or 27, as determined using the Kabat method.

In some embodiments, the VH domain of the antibody that binds mesothelin comprises amino acid residues 27-34, 52-59 and 98-111 of SEQ ID NO: 9; and/or the VL domain of the antibody comprises amino acid residues 27-32, 50-52 and 89-100 of SEQ ID NO: 11. In other embodiments, the VH domain of the antibody comprises amino acid residues 31-36, 51-67 and 100-111 of SEQ ID NO: 9; and/or the VL domain of the antibody comprises amino acid residues 24-34, 50-56 and 89-100 of SEQ ID NO: 11. In some examples, the amino acid sequence of the VH domain is at least 90%, at least 95%, at least 96%, at least 97%, at least 98% or at least 99% identical to SEQ ID NO: 9; and/or the amino acid sequence of the VL domain is at least 90%, at least 95%, at least 96%, at least 97%, at least 98% or at least 99% identical to SEQ ID NO: 11. In particular examples, the VH domain of the antibody comprises SEQ ID NO: 9 and/or the VL domain of the antibody comprises SEQ ID NO: 11.

In some embodiments, the VH domain of the antibody comprises amino acid residues 27-34, 52-59 and 98-112 of SEQ ID NO: 13; and/or the VL domain of the antibody comprises amino acid residues 27-32, 50-52 and 89-101 of SEQ ID NO: 15. In other embodiments, the VH domain of the antibody comprises amino acid residues 31-36, 51-68 and 100-112 of SEQ ID NO: 13; and/or the VL domain of the antibody comprises amino acid residues 24-34, 50-56 and 89-101 of SEQ ID NO: 15. In some examples, the amino acid sequence of the VH domain is at least 90%, at least 95%, at least 96%, at least 97%, at least 98% or at least 99% identical to SEQ ID NO: 13; and/or the amino acid sequence of the VL domain is at least 90%, at least 95%, at least 96%, at least 97%, at least 98% or at least 99% identical to SEQ ID NO: 15. In particular examples, the VH domain of the antibody comprises SEQ ID NO: 13 and/or the VL domain of the antibody comprises SEQ ID NO: 15.

In some embodiments, the VH domain of the antibody comprises amino acid residues 26-33, 51-58 and 97-108 of SEQ ID NO: 17; and/or the VL domain of the antibody comprises amino acid residues 27-32, 50-52 and 89-100 of SEQ ID NO: 19. In other embodiments, the VH domain of the antibody comprises amino acid residues 31-35, 50-67 and 99-108 of SEQ ID NO: 17; and/or the VL domain of the antibody comprises amino acid residues 24-34, 50-56 and 89-100 of SEQ ID NO: 19. In some examples, the amino acid sequence of the VH domain is at least 90%, at least 95%, at least 96%, at least 97%, at least 98% or at least 99% identical to SEQ ID NO: 17; and/or the amino acid sequence of the VL domain is at least 90%, at least 95%, at least 96%, at least 97%, at least 98% or at least 99% identical to SEQ ID NO: 19. In particular examples, the VH domain of the antibody comprises SEQ ID NO: 17 and/or the VL domain of the antibody comprises SEQ ID NO: 19.

In some embodiments, the VH domain of the antibody comprises amino acid residues 25-33, 51-57 and 96-113 of SEQ ID NO: 21, or amino acid residues 26-34, 52-60 and 98-112 of SEQ ID NO: 29; and/or the VL domain of the antibody comprises amino acid residues 27-32, 50-52 and 89-100 of SEQ ID NO: 23. In other embodiments, the VH domain of the antibody comprises amino acid residues 31-35, 50-66 and 98-113 of SEQ ID NO: 21, or amino acid residues 31-36, 51-68 and 100-112 of SEQ ID NO: 29; and/or the VL domain of the antibody comprises amino acid residues 24-34, 50-56 and 89-100 of SEQ ID NO: 23. In some examples, the amino acid sequence of the VH domain is at least 90%, at least 95%, at least 96%, at least 97%, at least 98% or at least 99% identical to SEQ ID NO: 21 or SEQ ID NO: 29; and/or the amino acid sequence of the VL domain is at least 90%, at least 95%, at least 96%, at least 97%, at least 98% or at least 99% identical to SEQ ID NO: 23. In particular examples, the VH domain of the antibody comprises SEQ ID NO: 21 or SEQ ID NO: 29 and/or the VL domain of the antibody comprises SEQ ID NO: 23.

In some embodiments, the VH domain of the antibody comprises amino acid residues 25-33, 51-59 and 97-109 of SEQ ID NO: 25; and/or the VL domain of the antibody comprises amino acid residues 27-32, 50-52 and 89-102 of SEQ ID NO: 27. In other embodiments, the VH domain of the antibody comprises amino acid residues 30-35, 50-67 and 99-109 of SEQ ID NO: 25; and/or the VL domain of the antibody comprises amino acid residues 24-34, 50-56 and 89-102 of SEQ ID NO: 27. In some examples, the amino acid sequence of the VH domain is at least 90%, at least 95%, at least 96%, at least 97%, at least 98% or at least 99% identical to SEQ ID NO: 25; and/or the amino acid sequence of the VL domain is at least 90%, at least 95%, at least 96%, at least 97%, at least 98% or at least 99% identical to SEQ ID NO: 27. In particular examples, the VH domain of the antibody comprises SEQ ID NO: 25 and/or the VL domain of the antibody comprises SEQ ID NO: 27.

Also provided are isolated monoclonal antibodies that bind, such as specifically bind, mesothelin, wherein the antibody comprises a VH domain comprising the amino acid sequence of SEQ ID NO: 9, SEQ ID NO: 13, SEQ ID NO: 17, SEQ ID NO: 21, SEQ ID NO: 29 or SEQ ID NO: 25; and/or a VL domain comprising the amino acid sequence of SEQ ID NO: 11, SEQ ID NO: 15, SEQ ID NO: 19, SEQ ID NO: 23 or SEQ ID NO: 27.

In some embodiments, the VH domain of the antibody comprises SEQ ID NO: 9 and/or the VL domain of the antibody comprises SEQ ID NO: 11.

In some embodiments, the VH domain of the antibody comprises SEQ ID NO: 13 and/or the VL domain of the antibody comprises SEQ ID NO: 15.

In some embodiments, the VH domain of the antibody comprises SEQ ID NO: 17 and/or the VL domain of the antibody comprises SEQ ID NO: 19.

In some embodiments, the VH domain of the antibody comprises SEQ ID NO: 21 and/or the VL domain of the antibody comprises SEQ ID NO: 23.

In some embodiments, the VH domain of the antibody comprises SEQ ID NO: 29 and/or the VL domain of the antibody comprises SEQ ID NO: 23.

In some embodiments, the VH domain of the antibody comprises SEQ ID NO: 25 and/or the VL domain of the antibody comprises SEQ ID NO: 27.

In some embodiments, the monoclonal antibodies that bind, such as specifically bind, mesothelin are humanized antibodies.

In some embodiments, the monoclonal antibody that binds, such as specifically binds, mesothelin is a Fab fragment, a Fab' fragment, a F(ab)'$_2$ fragment, a single chain variable fragment (scFv), or a disulfide stabilized variable fragment (dsFv). In other embodiments, the antibody is an immunoglobulin molecule. In particular examples, the antibody is an IgG.

In some embodiments, the disclosed antibodies bind mesothelin (soluble or cell-surface mesothelin) with a dissociation constant ($K_d$) of about 1 nM or less. In several embodiments, the monoclonal antibodies bind mesothelin with a binding affinity of about 1 nM, about 0.9 nM, about 0.8 nM, about 0.7 nM, about 0.6 nM, about 0.5 nM, about 0.4 nM, about 0.3 nM, about 0.2 nM, about 0.15 nM or about 0.1 nM.

The monoclonal antibodies disclosed herein can be labeled, such as with a fluorescent, enzymatic, or radioactive label.

Further provided herein are compositions comprising a therapeutically effective amount of the disclosed antibodies and a pharmaceutically acceptable carrier.

Immunoconjugates comprising the monoclonal antibodies disclosed herein and an effector molecule are also provided. The effector molecule can be, for example, a toxin or a detectable label. In some embodiments, the immunoconjugate comprises the VH and/or VL domain of one of the anti-mesothelin antibodies disclosed herein and a toxin, such as PE or a variant therefore, such as PE38. In particular examples, the immunoconjugate comprises the VH and VL of YP223, YP218, YP3, YP187 or YP158 fused to PE38. In some examples, the toxin is PE38 comprising the amino acid sequence of SEQ ID NO: 2. In particular non-limiting examples, the immunoconjugate comprises the amino acid sequence of SEQ ID NO: 31, SEQ ID NO: 33, SEQ ID NO: 35, SEQ ID NO: 37 or SEQ ID NO: 39. Examples of immunoconjugates are discussed in greater detail in section VI below.

Also provided herein are compositions comprising a therapeutically effective amount of the immunoconjugates disclosed herein and a pharmaceutically acceptable carrier.

Further provided herein are isolated nucleic acid molecules encoding the disclosed monoclonal antibodies. In some embodiments, the nucleotide sequence encoding the VH domain of the monoclonal antibody comprises at least a portion of SEQ ID NO: 8, SEQ ID NO: 12, SEQ ID NO: 16, SEQ ID NO: 20, SEQ ID NO: 28 or SEQ ID NO: 24, such as the portion encoding one or more CDRs of SEQ ID NO: 8, SEQ ID NO: 12, SEQ ID NO: 16, SEQ ID NO: 20, SEQ ID NO: 28 or SEQ ID NO: 24. In some examples, the VH domain of the monoclonal antibody comprises the nucleotide sequence of SEQ ID NO: 8, SEQ ID NO: 12, SEQ ID NO: 16, SEQ ID NO: 20, SEQ ID NO: 28 or SEQ ID NO: 24. In some embodiments, the nucleotide sequence encoding the VL domain of the monoclonal antibody comprises at least a portion of SEQ ID NO: 10, SEQ ID NO: 14, SEQ ID NO: 18, SEQ ID NO: 22 or SEQ ID NO: 26, such as a portion encoding one or more CDRs of SEQ ID NO: 10, SEQ ID NO: 14, SEQ ID NO: 18, SEQ ID NO: 22 or SEQ ID NO: 26. In some examples, the VL domain of the human monoclonal antibody comprises the nucleotide sequence of SEQ ID NO: 10, SEQ ID NO: 14, SEQ ID NO: 18, SEQ ID NO: 22 or SEQ ID NO: 26.

In some examples, the isolated nucleic acid molecule is operably linked to a promoter.

Also provided are expression vectors comprising the isolated nucleic acid molecules disclosed herein. Isolated host cells comprising the nucleic acid molecules or vectors are also provided herein. In some examples, the host cell is a T cell, such as a cytotoxic T lymphocyte (CTL).

V. Antibodies and Antibody Fragments

The monoclonal antibodies disclosed herein can be of any isotype. The monoclonal antibody can be, for example, an IgM or an IgG antibody, such as IgG$_1$ or an IgG$_2$. The class of an antibody that specifically binds mesothelin can be switched with another (for example, IgG can be switched to IgM), according to well-known procedures. Class switching can also be used to convert one IgG subclass to another, such as from IgG$_1$ to IgG$_2$.

Antibody fragments are also encompassed by the present disclosure, such as single-domain antibodies (e.g., VH domain antibodies), Fab, F(ab')2, and Fv. These antibody fragments retain the ability to selectively bind with the antigen. These fragments include:

(1) Fab, the fragment which contains a monovalent antigen-binding fragment of an antibody molecule, can be produced by digestion of whole antibody with the enzyme papain to yield an intact light chain and a portion of one heavy chain;

(2) Fab', the fragment of an antibody molecule can be obtained by treating whole antibody with pepsin, followed by reduction, to yield an intact light chain and a portion of the heavy chain; two Fab' fragments are obtained per antibody molecule;

(3) (Fab')$_2$, the fragment of the antibody that can be obtained by treating whole antibody with the enzyme pepsin without subsequent reduction; F(ab')2 is a dimer of two Fab' fragments held together by two disulfide bonds;

(4) Fv, a genetically engineered fragment containing the variable region of the light chain and the variable region of the heavy chain expressed as two chains;

(5) Single chain antibody (such as scFv), a genetically engineered molecule containing the variable region of the light chain, the variable region of the heavy chain, linked by a suitable polypeptide linker as a genetically fused single chain molecule;

(6) A dimer of a single chain antibody (scFV2), defined as a dimer of a scFV (also known as a "miniantibody"); and (7) VH single-domain antibody, an antibody fragment consisting of the heavy chain variable domain.

Methods of making these fragments are known in the art (see for example, Harlow and Lane, *Antibodies: A Laboratory Manual*, Cold Spring Harbor Laboratory, New York, 1988).

In some cases, antibody fragments can be prepared by proteolytic hydrolysis of the antibody or by expression in a host cell (such as *E. coli*) of DNA encoding the fragment. Antibody fragments can be obtained by pepsin or papain digestion of whole antibodies by conventional methods. For example, antibody fragments can be produced by enzymatic cleavage of antibodies with pepsin to provide a 5S fragment denoted F(ab')2. This fragment can be further cleaved using a thiol reducing agent, and optionally a blocking group for the sulfhydryl groups resulting from cleavage of disulfide linkages, to produce 3.5S Fab' monovalent fragments. Alternatively, an enzymatic cleavage using pepsin produces two monovalent Fab' fragments and an Fc fragment directly (see U.S. Pat. No. 4,036,945 and U.S. Pat. No. 4,331,647).

Other methods of cleaving antibodies, such as separation of heavy chains to form monovalent light-heavy chain fragments, further cleavage of fragments, or other enzymatic, chemical, or genetic techniques may also be used, so long as the fragments bind to the antigen that is recognized by the intact antibody.

One of skill will realize that conservative variants of the antibodies can be produced. Such conservative variants employed in antibody fragments, such as dsFv fragments or in scFv fragments, will retain critical amino acid residues necessary for correct folding and stabilizing between the V$_H$ and the V$_L$ regions, and will retain the charge characteristics of the residues in order to preserve the low pI and low toxicity of the molecules Amino acid substitutions (such as at most one, at most two, at most three, at most four, or at most five amino acid substitutions) can be made in the V$_H$ and/or the V$_L$ regions to increase yield. Conservative amino acid substitution tables providing functionally similar amino acids are well known to one of ordinary skill in the art. The following six groups are examples of amino acids that are considered to be conservative substitutions for one another:

1) Alanine (A), Serine (5), Threonine (T);
 2) Aspartic acid (D), Glutamic acid (E);
 3) Asparagine (N), Glutamine (Q);
 4) Arginine (R), Lysine (K);
 5) Isoleucine (I), Leucine (L), Methionine (M), Valine (V); and
 6) Phenylalanine (F), Tyrosine (Y), Tryptophan (W).

VI. Immunoconjugates

The disclosed monoclonal antibodies specific for mesothelin or a fragment thereof can be conjugated to a therapeutic agent or effector molecule Immunoconjugates include, but are not limited to, molecules in which there is a covalent linkage of a therapeutic agent to an antibody. A therapeutic agent is an agent with a particular biological activity directed against a particular target molecule or a cell bearing a target molecule. One of skill in the art will appreciate that therapeutic agents can include various drugs such as vinblastine, daunomycin and the like, cytotoxins such as native or modified *Pseudomonas* exotoxin or Diphtheria toxin, encapsulating agents (such as liposomes) which themselves contain pharmacological compositions, radioactive agents such as $^{125}I$, $^{32}P$, $^{14}C$, $^{3}H$ and $^{35}S$ and other labels, target moieties and ligands.

The choice of a particular therapeutic agent depends on the particular target molecule or cell, and the desired biological effect. Thus, for example, the therapeutic agent can be a cytotoxin that is used to bring about the death of a particular target cell (such as a tumor cell). Conversely, where it is desired to invoke a non-lethal biological response, the therapeutic agent can be conjugated to a non-lethal pharmacological agent or a liposome containing a non-lethal pharmacological agent.

With the therapeutic agents and antibodies described herein, one of skill can readily construct a variety of clones containing functionally equivalent nucleic acids, such as nucleic acids which differ in sequence but which encode the same effector moiety or antibody sequence. Thus, the present disclosure provides nucleic acids encoding antibodies and conjugates and fusion proteins thereof.

Effector molecules can be linked to an antibody of interest using any number of means known to those of skill in the art. Both covalent and noncovalent attachment means may be used. The procedure for attaching an effector molecule to an antibody varies according to the chemical structure of the effector. Polypeptides typically contain a variety of functional groups; such as carboxylic acid (COOH), free amine (—NH$_2$) or sulfhydryl (—SH) groups, which are available for reaction with a suitable functional group on an antibody to result in the binding of the effector molecule. Alternatively, the antibody is derivatized to expose or attach additional reactive functional groups. The derivatization may involve attachment of any of a number of known linker molecules. The linker can be any molecule used to join the antibody to the effector molecule. The linker is capable of forming covalent bonds to both the antibody and to the effector molecule. Suitable linkers are well known to those of skill in the art and include, but are not limited to, straight or branched-chain carbon linkers, heterocyclic carbon linkers, or peptide linkers. Where the antibody and the effector molecule are polypeptides, the linkers may be joined to the constituent amino acids through their side groups (such as through a disulfide linkage to cysteine) or to the alpha carbon amino and carboxyl groups of the terminal amino acids.

In some circumstances, it is desirable to free the effector molecule from the antibody when the immunoconjugate has reached its target site. Therefore, in these circumstances, immunoconjugates will comprise linkages that are cleavable in the vicinity of the target site. Cleavage of the linker to release the effector molecule from the antibody may be prompted by enzymatic activity or conditions to which the immunoconjugate is subjected either inside the target cell or in the vicinity of the target site.

In view of the large number of methods that have been reported for attaching a variety of radiodiagnostic compounds, radiotherapeutic compounds, label (such as enzymes or fluorescent molecules) drugs, toxins, and other agents to antibodies one skilled in the art will be able to determine a suitable method for attaching a given agent to an antibody or other polypeptide.

The antibodies or antibody fragments disclosed herein can be derivatized or linked to another molecule (such as another peptide or protein). In general, the antibodies or portion thereof is derivatized such that the binding to the target antigen is not affected adversely by the derivatization or labeling. For example, the antibody can be functionally linked (by chemical coupling, genetic fusion, noncovalent association or otherwise) to one or more other molecular entities, such as another antibody (for example, a bispecific antibody or a diabody), a detection agent, a pharmaceutical agent, and/or a protein or peptide that can mediate association of the antibody or antibody portion with another molecule (such as a streptavidin core region or a polyhistidine tag).

One type of derivatized antibody is produced by crosslinking two or more antibodies (of the same type or of different types, such as to create bispecific antibodies). Suitable crosslinkers include those that are heterobifunctional, having two distinctly reactive groups separated by an appropriate spacer (such as m-maleimidobenzoyl-N-hydroxysuccinimide ester) or homobifunctional (such as disuccinimidyl suberate). Such linkers are commercially available.

An antibody that binds (for example specifically binds) mesothelin or a fragment thereof can be labeled with a detectable moiety. Useful detection agents include fluorescent compounds, including fluorescein, fluorescein isothiocyanate, rhodamine, 5-dimethylamine-1-napthalenesulfonyl chloride, phycoerythrin, lanthanide phosphors and the like. Bioluminescent markers are also of use, such as luciferase, Green fluorescent protein (GFP), Yellow fluorescent protein (YFP). An antibody can also be labeled with enzymes that are useful for detection, such as horseradish peroxidase, β-galactosidase, luciferase, alkaline phosphatase, glucose oxidase and the like. When an antibody is labeled with a detectable enzyme, it can be detected by adding additional reagents that the enzyme uses to produce a reaction product that can be discerned. For example, when the agent horseradish peroxidase is present the addition of hydrogen peroxide and diaminobenzidine leads to a colored reaction product, which is visually detectable. An antibody may also be labeled with biotin, and detected through indirect measurement of avidin or streptavidin binding. It should be noted that the avidin itself can be labeled with an enzyme or a fluorescent label.

An antibody may be labeled with a magnetic agent, such as gadolinium. Antibodies can also be labeled with lanthanides (such as europium and dysprosium), and manganese. Paramagnetic particles such as superparamagnetic iron oxide are also of use as labels. An antibody may also be labeled with a predetermined polypeptide epitopes recognized by a secondary reporter (such as leucine zipper pair sequences, binding sites for secondary antibodies, metal binding domains, epitope tags). In some embodiments, labels are attached by spacer arms of various lengths to reduce potential steric hindrance.

An antibody can also be labeled with a radiolabeled amino acid. The radiolabel may be used for both diagnostic and therapeutic purposes. For instance, the radiolabel may be used to detect mesothelin by x-ray, emission spectra, or other diagnostic techniques. Examples of labels for polypeptides include, but are not limited to, the following radioisotopes or radionucleotides: $^{3}H$, $^{14}C$, $^{15}N$, $^{35}S$, $^{90}Y$, $^{99}Tc$, $^{111}In$, $^{125}I$, $^{131}I$.

An antibody can also be derivatized with a chemical group such as polyethylene glycol (PEG), a methyl or ethyl group, or a carbohydrate group. These groups may be useful to improve the biological characteristics of the antibody, such as to increase serum half-life or to increase tissue binding.

Toxins can be employed with the monoclonal antibodies described herein to produce immunotoxins. Exemplary toxins include ricin, abrin, diphtheria toxin and subunits thereof, as well as botulinum toxins A through F. These toxins are readily available from commercial sources (for example, Sigma Chemical Company, St. Louis, Mo.). Contemplated toxins also include variants of the toxins described herein (see, for example, see, U.S. Pat. Nos. 5,079,163 and 4,689,401). In one embodiment, the toxin is *Pseudomonas* exotoxin (PE) (U.S. Pat. No. 5,602,095). As used herein "*Pseudomonas* exotoxin" refers to a full-length native (naturally occurring) PE or a PE that has been modified. Such modifications can include, but are not limited to, elimination of domain Ia, various amino acid deletions in domains Ib, II and III, single amino acid substitutions and the addition of one or more sequences at the carboxyl terminus (for example, see Siegall et al., *J. Biol. Chem.* 264:14256-14261, 1989).

PE employed with the monoclonal antibodies described herein can include the native sequence, cytotoxic fragments of the native sequence, and conservatively modified variants of native PE and its cytotoxic fragments. Cytotoxic fragments of PE include those which are cytotoxic with or without subsequent proteolytic or other processing in the target cell. Cytotoxic fragments of PE include PE40, PE38, and PE35. For additional description of PE and variants thereof, see for example, U.S. Pat. Nos. 4,892,827; 5,512,658; 5,602,095; 5,608,039; 5,821,238; and 5,854,044; PCT Publication No. WO 99/51643; Pai et al., *Proc. Natl. Acad. Sci. USA* 88:3358-3362, 1991; Kondo et al., *J. Biol. Chem.* 263:9470-9475, 1988; Pastan et al., *Biochim. Biophys. Acta* 1333:C1-C6, 1997.

```
The full-length PE sequence is set forth herein
as SEQ ID NO: 1:
AEEAFDLWNECAKACVLDLKDGVRSSRMSVDPAIADTNGQGVLHYSMVLE

GGNDALKLAIDNALSITSDGLTIRLEGGVEPNKPVRYSYTRQARGSWSLN

WLVPIGHEKPSNIKVFIHELNAGNQLSHMSPIYTIEMGDELLAKLARDAT

FFVRAHESNEMQPTLAISHAGVSVVMAQTQPRREKRWSEWASGKVLCLLD

PLDGVYNYLAQQRCNLDDTWEGKIYRVLAGNPAKHDLDIKPTVISHRLHF

PEGGSLAALTAHQACHLPLETFTRHRQPRGWEQLEQCGYPVQRLVALYLA

ARLSWNQVDQVIRNALASPGSGGDLGEAIREQPEQARLALTLAAAESERF

VRQGTGNDEAGAANADVVSLTCPVAAGECAGPADSGDALLERNYPTGAEF

LGDGGDVSFSTRGTQNWTVERLLQAHRQLEERGYVFVGYHGTFLEAAQSI

VFGGVRARSQDLDAIWRGFYIAGDPALAYGYAQDQEPDARGRIRNGALLR

VYVPRSSLPGFYRTSLTLAAPEAAGEVERLIGHPLPLRLDAITGPEEEGG

RLETILGWPLAERTVVIPSAIPTDPRNVGGDLDPSSIPDKEQAISALPDY

ASQPGKPPREDLK

In some examples, the PE is PE38, comprising the
following amino acid sequence:
                                     (SEQ ID NO: 2)
PEGGSLAALTAHQACHLPLETFTRHRQPRGWEQLEQCGYPVQRLVALYLA

ARLSWNQVDQVIRNALASPGSGGDLGEAIREQPEQARLALTLAAAESERF

VRQGTGNDEAGAANGPADSGDALLERNYPTGAEFLGDGGDVSFSTRGTQN
```

-continued

```
WTVERLLQAHRQLEERGYVFVGYHGTFLEAAQSIVFGGVRARSQDLDAIW

RGFYIAGDPALAYGYAQDQEPDARGRIRNGALLRVYVPRSSLPGFYRTSL

TLAAPEAAGEVERLIGHPLPLRLDAITGPEEEGGRLETILGWPLAERTVV

IPSAIPTDPRNVGGDLDPSSIPDKEQAISALPDYASQPGKPPREDLK
```

Also contemplated herein are protease-resistant PE variants and PE variants with reduced immunogenicity, such as, but not limited to, PE-LR, PE-6X, PE-8X, PE-LR/6X and PE-LR/8X (see, for example, Weldon et al., *Blood* 113(16):3792-3800, 2009; Onda et al., *Proc Natl Acad Sci USA* 105(32):11311-11316, 2008; and PCT Publication Nos. WO 2007/016150, WO 2009/032954 and WO 2011/032022, which are herein incorporated by reference).

In some examples, the PE is a variant that is resistant to lysosomal degradation, such as PE-LR (Weldon et al., *Blood* 113(16):3792-3800, 2009; PCT Publication No. WO 2009/032954) having the following amino acid sequence:

```
                                     (SEQ ID NO: 3)
RHRQPRGWEQLPTGAEFLGDGGDVSFSTRGTQNWTVERLLQAHRQLEERG

YVFVGYHGTFLEAAQSIVFGGVRARSQDLDAIWRGFYIAGDPALAYGYAQ

DQEPDARGRIRNGALLRVYVPRSSLPGFYRTSLTLAAPEAAGEVERLIGH

PLPLRLDAITGPEEEGGRLETILGWPLAERTVVIPSAIPTDPRNVGGDLD

PSSIPDKEQAISALPDYASQPGKPPREDLK
```

In other examples, the PE is a variant designated PE-LR/6X (PCT Publication No. WO 2011/032022) having the following amino acid sequence:

```
                                     (SEQ ID NO: 4)
RHRQPRGWEQLPTGAEFLGDGGDVSFSTRGTQNWTVERLLQAHRQLEEGG

YVFVGYHGTFLEAAQSIVFGGVRARSQDLDAIWAGFYIAGDPALAYGYAQ

DQEPDAAGRIRNGALLRVYVPRSSLPGFYATSLTLAAPEAAGEVERLIGH

PLPLRLDAITGPEESGGRLETILGWPLAERTVVIPSAIPTDPRNVGGDLD

PSSIPDSEQAISALPDYASQPGKPPREDLK
```

In other examples, the PE variant is PE with reducing immunogenicity, such as a PE with the following sequence:

```
RHRQPRGWEQLPTGAEFLGDGGXVSFSTRGTQNWTVERLLQAHRQLEEXG

YVFVGYHGTFLEAAQSIVFGGVRARSQDLDAIWXGFYIAGDPALAYGYAQ

DQEPDAXGRIRNGALLRVYVPRSSLPGFYXTSLTLAAPEAAGEVERLIGH

PLPLRLDAITGPEEXGGRLETILGWPLAERTVVIPSAIPTDPRNVGGDLD

PSSIPDXEXAISALPDYASQPGKPPREDLK (X = G, A or S;
SEQ ID NO: 5)
```

In other examples, the PE is a variant designated PE-LR/8M (PCT Publication No. WO 2011/032022) having the following amino acid sequence:

```
                                     (SEQ ID NO: 6)
RHRQPRGWEQLPTGAEFLGDGGAVSFSTRGTQNWTVERLLQAHRQLEEGG

YVFVGYHGTFLEAAQSIVFGGVRARSQDLDAIWAGFYIAGDPALAYGYAQ
```

```
-continued
DQEPDAAGRIRNGALLRVYVPRSSLPGFYATSLTLAAPEAAGEVERLIGH

PLPLRLDAITGPEESGGRLETILGWPLAERTVVIPSAIPTDPRNVGGDLD

PSSIPDSEAAISALPDYASQPGKPPREDLK
```

Substitutions of PE are defined herein by reference to the amino acid sequence of full-length PE set forth herein as SEQ ID NO: 1. Substitutions of PE are described herein by reference to the amino acid residue present at a particular position, followed by the amino acid with which that residue has been replaced in the particular substitution. In this regard, the positions of the amino acid sequence of a particular embodiment of a PE are referred to herein as the positions of the amino acid sequence of the particular embodiment, or as the positions as defined by SEQ ID NO: 1. Thus, substitutions refer to a replacement of an amino acid residue in the amino acid sequence of a particular embodiment of a PE corresponding to the indicated position of the 613-amino acid sequence of SEQ ID NO: 1 with the understanding that the actual positions in the respective amino acid sequence may be different. In the event of multiple substitutions at two or more positions, the two or more substitutions may be the same or different—each amino acid residue of the two or more amino acid residues being substituted can be substituted with the same or different amino acid residue unless explicitly indicated otherwise.

Modification of PE may occur in any previously described variant, including cytotoxic fragments of PE (for example, PE38, PE-LR and PE-LR/8M). Modified PEs may include any substitution(s), as described above, for one or more amino acid residues within one or more T-cell epitopes and/or B cell epitopes of PE.

In particular examples disclosed herein, the immunoconjugate comprises the amino acid sequence of SEQ ID NO: 31, SEQ ID NO: 33, SEQ ID NO: 35, SEQ ID NO: 37 or SEQ ID NO: 39, and/or is encoded by the nucleic acid sequence of SEQ ID NO: 30, SEQ ID NO: 32, SEQ ID NO: 34, SEQ ID NO: 36 or SEQ ID NO: 38.

The antibodies described herein can also be used to target any number of different diagnostic or therapeutic compounds to cells expressing mesothelin on their surface. Thus, an antibody of the present disclosure can be attached directly or via a linker to a drug that is to be delivered directly to cells expressing cell-surface mesothelin. This can be done for therapeutic, diagnostic or research purposes. Therapeutic agents include such compounds as nucleic acids, proteins, peptides, amino acids or derivatives, glycoproteins, radioisotopes, lipids, carbohydrates, or recombinant viruses. Nucleic acid therapeutic and diagnostic moieties include antisense nucleic acids, derivatized oligonucleotides for covalent cross-linking with single or duplex DNA, and triplex forming oligonucleotides.

Alternatively, the molecule linked to an anti-mesothelin antibody can be an encapsulation system, such as a liposome or micelle that contains a therapeutic composition such as a drug, a nucleic acid (for example, an antisense nucleic acid), or another therapeutic moiety that is preferably shielded from direct exposure to the circulatory system. Means of preparing liposomes attached to antibodies are well known to those of skill in the art (see, for example, U.S. Pat. No. 4,957,735; Connor et al., *Pharm. Ther.* 28:341-365, 1985).

Antibodies described herein can also be covalently or non-covalently linked to a detectable label. Detectable labels suitable for such use include any composition detectable by spectroscopic, photochemical, biochemical, immunochemical, electrical, optical or chemical means. Useful labels include magnetic beads, fluorescent dyes (for example, fluorescein isothiocyanate, Texas red, rhodamine, green fluorescent protein, and the like), radiolabels (for example, $^3$H, $^{125}$I, $^{35}$S, $^{14}$C, or $^{32}$P), enzymes (such as horseradish peroxidase, alkaline phosphatase and others commonly used in an ELISA), and colorimetric labels such as colloidal gold or colored glass or plastic (such as polystyrene, polypropylene, latex, and the like) beads.

Means of detecting such labels are well known to those of skill in the art. Thus, for example, radiolabels may be detected using photographic film or scintillation counters, fluorescent markers may be detected using a photodetector to detect emitted illumination. Enzymatic labels are typically detected by providing the enzyme with a substrate and detecting the reaction product produced by the action of the enzyme on the substrate, and colorimetric labels are detected by simply visualizing the colored label.

VII. Compositions and Methods of Use

Compositions are provided that include one or more of the disclosed antibodies that bind (for example specifically bind) mesothelin in a carrier. Compositions comprising immunoconjugates or immunotoxins are also provided. The compositions can be prepared in unit dosage forms for administration to a subject. The amount and timing of administration are at the discretion of the treating clinician to achieve the desired outcome. The antibody can be formulated for systemic or local (such as intra-tumor) administration. In one example, the antibody is formulated for parenteral administration, such as intravenous administration.

The compositions for administration can include a solution of the antibody dissolved in a pharmaceutically acceptable carrier, such as an aqueous carrier. A variety of aqueous carriers can be used, for example, buffered saline and the like. These solutions are sterile and generally free of undesirable matter. These compositions may be sterilized by conventional, well known sterilization techniques. The compositions may contain pharmaceutically acceptable auxiliary substances as required to approximate physiological conditions such as pH adjusting and buffering agents, toxicity adjusting agents and the like, for example, sodium acetate, sodium chloride, potassium chloride, calcium chloride, sodium lactate and the like. The concentration of antibody in these formulations can vary widely, and will be selected primarily based on fluid volumes, viscosities, body weight and the like in accordance with the particular mode of administration selected and the subject's needs.

A typical pharmaceutical composition for intravenous administration includes about 0.1 to 10 mg of antibody per subject per day. Dosages from 0.1 up to about 100 mg per subject per day may be used, particularly if the agent is administered to a secluded site and not into the circulatory or lymph system, such as into a body cavity or into a lumen of an organ. Actual methods for preparing administrable compositions will be known or apparent to those skilled in the art and are described in more detail in such publications as *Remington's Pharmaceutical Science*, 19th ed., Mack Publishing Company, Easton, Pa. (1995).

Antibodies may be provided in lyophilized form and rehydrated with sterile water before administration, although they are also provided in sterile solutions of known concentration. The antibody solution is then added to an infusion bag containing 0.9% sodium chloride, USP, and in some cases administered at a dosage of from 0.5 to 15 mg/kg of body weight. Considerable experience is available in the art in the administration of antibody drugs, which have been marketed in the U.S. since the approval of RITUXAN® in 1997. Antibodies can be administered by slow infusion, rather than in an intravenous push or bolus. In one example, a higher loading dose is administered, with subsequent, maintenance doses being administered at a lower level. For example, an initial loading dose of 4 mg/kg may be infused over a period of some 90 minutes, followed by weekly maintenance doses for 4-8 weeks of 2 mg/kg infused over a 30 minute period if the previous dose was well tolerated.

Controlled release parenteral formulations can be made as implants, oily injections, or as particulate systems. For a broad overview of protein delivery systems see, Banga, A. J., *Therapeutic Peptides and Proteins: Formulation, Processing, and Delivery Systems*, Technomic Publishing Company, Inc., Lancaster, Pa., (1995). Particulate systems include microspheres, microparticles, microcapsules, nanocapsules, nanospheres, and nanoparticles. Microcapsules contain the therapeutic protein, such as a cytotoxin or a drug, as a central core. In microspheres the therapeutic is dispersed throughout the particle. Particles, microspheres, and microcapsules smaller than about 1 μm are generally referred to as nanoparticles, nanospheres, and nanocapsules, respectively. Capillaries have a diameter of approximately 5 μm so that only nanoparticles are administered intravenously. Microparticles are typically around 100 μm in diameter and are administered subcutaneously or intramuscularly. See, for example, Kreuter, J., *Colloidal Drug Delivery Systems*, J. Kreuter, ed., Marcel Dekker, Inc., New York, N.Y., pp. 219-342 (1994); and Tice & Tabibi, *Treatise on Controlled Drug Delivery*, A. Kydonieus, ed., Marcel Dekker, Inc. New York, N.Y., pp. 315-339, (1992).

Polymers can be used for ion-controlled release of the antibody compositions disclosed herein. Various degradable and nondegradable polymeric matrices for use in controlled drug delivery are known in the art (Langer, *Accounts Chem. Res.* 26:537-542, 1993). For example, the block copolymer, polaxamer 407, exists as a viscous yet mobile liquid at low temperatures but forms a semisolid gel at body temperature. It has been shown to be an effective vehicle for formulation and sustained delivery of recombinant interleukin-2 and urease (Johnston et al., *Pharm. Res.* 9:425-434, 1992; and Pec et al., *J. Parent. Sci. Tech.* 44(2):58-65, 1990). Alternatively, hydroxyapatite has been used as a microcarrier for controlled release of proteins (Ijntema et al., *Int. J. Pharm.* 112:215-224, 1994). In yet another aspect, liposomes are used for controlled release as well as drug targeting of the lipid-capsulated drug (Betageri et al., *Liposome Drug Delivery Systems*, Technomic Publishing Co., Inc., Lancaster, Pa. (1993)). Numerous additional systems for controlled delivery of therapeutic proteins are known (see U.S. Pat. No. 5,055,303; U.S. Pat. No. 5,188,837; U.S. Pat. No. 4,235,871; U.S. Pat. No. 4,501,728; U.S. Pat. No. 4,837,028; U.S. Pat. No. 4,957,735; U.S. Pat. No. 5,019,369; U.S. Pat. No. 5,055,303; U.S. Pat. No. 5,514,670; U.S. Pat. No. 5,413,797; U.S. Pat. No. 5,268,164; U.S. Pat. No. 5,004,697; U.S. Pat. No. 4,902,505; U.S. Pat. No. 5,506,206; U.S. Pat. No. 5,271,961; U.S. Pat. No. 5,254,342 and U.S. Pat. No. 5,534,496).

A. Therapeutic Methods

The antibodies, compositions and immunoconjugates disclosed herein can be administered to slow or inhibit the growth of tumor cells or inhibit the metastasis of tumor cells, such as mesothelioma, prostate cancer, lung cancer, stomach cancer, squamous cell carcinoma, pancreatic cancer, cholangiocarcinoma, breast cancer or ovarian cancer. In these applications, a therapeutically effective amount of an antibody is administered to a subject in an amount sufficient to inhibit growth, replication or metastasis of cancer cells, or to inhibit a sign or a symptom of the cancer. Suitable subjects may include those diagnosed with a cancer that expresses mesothelin, such as, but not limited to, mesothelioma, prostate cancer, lung cancer, stomach cancer, squamous cell carcinoma, pancreatic cancer, cholangiocarcinoma, breast cancer or ovarian cancer.

In one non-limiting embodiment, provided herein is a method of treating a subject with cancer by selecting a subject with a cancer that expresses mesothelin and administering to the subject a therapeutically effective amount of an antibody, composition or immunoconjugate disclosed herein.

Also provided herein is a method of inhibiting tumor growth or metastasis by selecting a subject with a cancer that expresses mesothelin and administering to the subject a therapeutically effective amount of an antibody, composition or immunoconjugate disclosed herein.

A therapeutically effective amount of a mesothelin-specific antibody or immunoconjugate will depend upon the severity of the disease and the general state of the patient's health. A therapeutically effective amount of the antibody is that which provides either subjective relief of a symptom(s) or an objectively identifiable improvement as noted by the clinician or other qualified observer.

Administration of the antibodies and immunoconjugates disclosed herein can also be accompanied by administration of other anti-cancer agents or therapeutic treatments (such as surgical resection of a tumor). Any suitable anti-cancer agent can be administered in combination with the antibodies, compositions and immunoconjugates disclosed herein. Exemplary anti-cancer agents include, but are not limited to, chemotherapeutic agents, such as, for example, mitotic inhibitors, alkylating agents, anti-metabolites, intercalating antibiotics, growth factor inhibitors, cell cycle inhibitors, enzymes, topoisomerase inhibitors, anti-survival agents, biological response modifiers, anti-hormones (e.g. anti-androgens) and anti-angiogenesis agents. Other anti-cancer treatments include radiation therapy and other antibodies that specifically target cancer cells.

Non-limiting examples of alkylating agents include nitrogen mustards (such as mechlorethamine, cyclophosphamide, melphalan, uracil mustard or chlorambucil), alkyl sulfonates (such as busulfan), nitrosoureas (such as carmustine, lomustine, semustine, streptozocin, or dacarbazine).

Non-limiting examples of antimetabolites include folic acid analogs (such as methotrexate), pyrimidine analogs (such as 5-FU or cytarabine), and purine analogs, such as mercaptopurine or thioguanine.

Non-limiting examples of natural products include *vinca* alkaloids (such as vinblastine, vincristine, or vindesine), epipodophyllotoxins (such as etoposide or teniposide), antibiotics (such as dactinomycin, daunorubicin, doxorubicin, bleomycin, plicamycin, or mitomycin C), and enzymes (such as L-asparaginase).

Non-limiting examples of miscellaneous agents include platinum coordination complexes (such as cis-diamine-dichloroplatinum II also known as cisplatin), substituted ureas (such as hydroxyurea), methyl hydrazine derivatives (such as procarbazine), and adrenocrotical suppressants (such as mitotane and aminoglutethimide).

Non-limiting examples of hormones and antagonists include adrenocorticosteroids (such as prednisone), progestins (such as hydroxyprogesterone caproate, medroxyprogesterone acetate, and magestrol acetate), estrogens (such as diethylstilbestrol and ethinyl estradiol), antiestrogens (such as tamoxifen), and androgens (such as testerone proprionate and fluoxymesterone). Examples of the most commonly used chemotherapy drugs include Adriamycin, Alkeran, Ara-C, BiCNU, Busulfan, CCNU, Carboplatinum, Cisplatinum, Cytoxan, Daunorubicin, DTIC, 5-FU, Fludarabine, Hydrea, Idarubicin, Ifosfamide, Methotrexate, Mithramycin, Mitomycin, Mitoxantrone, Nitrogen Mustard, Taxol (or other taxanes, such as docetaxel), Velban, Vincristine, VP-16, while some more newer drugs include Gemcitabine (Gemzar), Herceptin, Irinotecan (Camptosar, CPT-11), Leustatin, Navelbine, Rituxan STI-571, Taxotere, Topotecan (Hycamtin), Xeloda (Capecitabine), Zevelin and calcitriol.

Non-limiting examples of immunomodulators that can be used include AS-101 (Wyeth-Ayerst Labs.), bropirimine (Upjohn), gamma interferon (Genentech), GM-CSF (granulocyte macrophage colony stimulating factor; Genetics Institute), IL-2 (Cetus or Hoffman-LaRoche), human immune globulin (Cutter Biological), IMREG (from Imreg of New Orleans, La.), SK&F 106528, and TNF (tumor necrosis factor; Genentech).

Another common treatment for some types of cancer is surgical treatment, for example surgical resection of the cancer or a portion of it. Another example of a treatment is radiotherapy, for example administration of radioactive material or energy (such as external beam therapy) to the tumor site to help eradicate the tumor or shrink it prior to surgical resection.

B. Methods for Diagnosis and Detection

Methods are provided herein for detecting expression of mesothelin in vitro or in vivo. In some cases, mesothelin expression is detected in a biological sample. The sample can be any sample, including, but not limited to, tissue from biopsies, autopsies and pathology specimens. Biological samples also include sections of tissues, for example, frozen sections taken for histological purposes. Biological samples further include body fluids, such as blood, serum, plasma, sputum, spinal fluid or urine. A biological sample is typically obtained from a mammal, such as a human or non-human primate.

In one embodiment, provided is a method of determining if a subject has cancer by contacting a sample from the subject with a monoclonal antibody disclosed herein; and detecting binding of the antibody to the sample. An increase in binding of the antibody to the sample as compared to binding of the antibody to a control sample identifies the subject as having cancer.

In another embodiment, provided is a method of confirming a diagnosis of cancer in a subject by contacting a sample from a subject diagnosed with cancer with a monoclonal antibody disclosed herein; and detecting binding of the antibody to the sample. An increase in binding of the antibody to the sample as compared to binding of the antibody to a control sample confirms the diagnosis of cancer in the subject.

In some examples of the disclosed methods, the monoclonal antibody is directly labeled.

In some examples, the methods further include contacting a second antibody that specifically binds the monoclonal antibody with the sample; and detecting the binding of the second antibody. An increase in binding of the second antibody to the sample as compared to binding of the second antibody to a control sample detects cancer in the subject or confirms the diagnosis of cancer in the subject.

In some cases, the cancer is mesothelioma, prostate cancer, lung cancer, stomach cancer, squamous cell carcinoma, pancreatic cancer, cholangiocarcinoma, breast cancer or ovarian cancer, or any other type of cancer that expresses mesothelin.

In some examples, the control sample is a sample from a subject without cancer. In particular examples, the sample is a blood or tissue sample.

In some cases, the antibody that binds (for example specifically binds) mesothelin is directly labeled with a detectable label. In another embodiment, the antibody that binds (for example, specifically binds) mesothelin (the first antibody) is unlabeled and a second antibody or other molecule that can bind the antibody that specifically binds mesothelin is labeled. As is well known to one of skill in the art, a second antibody is chosen that is able to specifically bind the specific species and class of the first antibody. For example, if the first antibody is a human IgG, then the secondary antibody may be an anti-human-IgG. Other molecules that can bind to antibodies include, without limitation, Protein A and Protein G, both of which are available commercially.

Suitable labels for the antibody or secondary antibody are described above, and include various enzymes, prosthetic groups, fluorescent materials, luminescent materials, magnetic agents and radioactive materials. Non-limiting examples of suitable enzymes include horseradish peroxidase, alkaline phosphatase, beta-galactosidase, or acetylcholinesterase. Non-limiting examples of suitable prosthetic group complexes include streptavidin/biotin and avidin/biotin. Non-limiting examples of suitable fluorescent materials include umbelliferone, fluorescein, fluorescein isothiocyanate, rhodamine, dichlorotriazinylamine fluorescein, dansyl chloride or phycoerythrin. A non-limiting exemplary luminescent material is luminol; a non-limiting exemplary a magnetic agent is gadolinium, and non-limiting exemplary radioactive labels include $^{125}I$, $^{131}I$, $^{35}S$ or $^{3}H$.

In an alternative embodiment, mesothelin can be assayed in a biological sample by a competition immunoassay utilizing mesothelin standards labeled with a detectable substance and an unlabeled antibody that specifically binds mesothelin. In this assay, the biological sample, the labeled mesothelin standards and the antibody that specifically bind mesothelin are combined and the amount of labeled mesothelin standard bound to the unlabeled antibody is determined. The amount of mesothelin in the biological sample is inversely proportional to the amount of labeled mesothelin standard bound to the antibody that specifically binds mesothelin.

The immunoassays and method disclosed herein can be used for a number of purposes. In one embodiment, the antibody that specifically binds mesothelin may be used to detect the production of mesothelin in cells in cell culture. In another embodiment, the antibody can be used to detect the amount of mesothelin in a biological sample, such as a tissue sample, or a blood or serum sample. In some examples, the mesothelin is cell-surface mesothelin. In other examples, the mesothelin is soluble mesothelin (e.g. mesothelin in a cell culture supernatant or soluble mesothelin in a body fluid sample, such as a blood or serum sample).

In one embodiment, a kit is provided for detecting mesothelin in a biological sample, such as a blood sample or tissue sample. For example, to confirm a cancer diagnosis in a subject, a biopsy can be performed to obtain a tissue sample for histological examination. Alternatively, a blood sample can be obtained to detect the presence of soluble mesothelin protein or fragment. Kits for detecting a polypeptide will typically comprise a monoclonal antibody that specifically binds mesothelin, such as any of the antibodies disclosed herein. In some embodiments, an antibody fragment, such as an scFv fragment, a VH domain, or a Fab is included in the kit. In a further embodiment, the antibody is labeled (for example, with a fluorescent, radioactive, or an enzymatic label).

In one embodiment, a kit includes instructional materials disclosing means of use of an antibody that binds mesothelin. The instructional materials may be written, in an electronic form (such as a computer diskette or compact disk) or may be visual (such as video files). The kits may also include additional components to facilitate the particular application for which the kit is designed. Thus, for example, the kit may additionally contain means of detecting a label (such as enzyme substrates for enzymatic labels, filter sets to detect fluorescent labels, appropriate secondary labels such as a secondary antibody, or the like). The kits may additionally include buffers and other reagents routinely used for the practice of a particular method. Such kits and appropriate contents are well known to those of skill in the art.

In one embodiment, the diagnostic kit comprises an immunoassay. Although the details of the immunoassays may vary with the particular format employed, the method of detecting mesothelin in a biological sample generally includes the steps of contacting the biological sample with an antibody which specifically reacts, under immunologically reactive conditions, to a mesothelin polypeptide. The antibody is allowed to specifically bind under immunologically reactive conditions to form an immune complex, and the presence of the immune complex (bound antibody) is detected directly or indirectly.

Methods of determining the presence or absence of a cell surface marker are well known in the art. For example, the antibodies can be conjugated to other compounds including, but not limited to, enzymes, magnetic beads, colloidal magnetic beads, haptens, fluorochromes, metal compounds, radioactive compounds or drugs. The antibodies can also be utilized in immunoassays such as but not limited to radioimmunoassays (RIAs), ELISA, or immunohistochemical assays.

The antibodies can also be used for fluorescence activated cell sorting (FACS). FACS employs a plurality of color channels, low angle and obtuse light-scattering detection channels, and impedance channels, among other more sophisticated levels of detection, to separate or sort cells (see U.S. Pat. No. 5,061,620). Any of the monoclonal antibodies that bind mesothelin, as disclosed herein, can be used in these assays. Thus, the antibodies can be used in a conventional immunoassay, including, without limitation, an ELISA, an RIA, FACS, tissue immunohistochemistry, Western blot or immunoprecipitation.

C. Engineered Cytotoxic T Lymphocytes (CTLs)

The disclosed monoclonal antibodies can also be used to produce CTLs engineered to express chimeric antigen receptors (CARs; also known as chimeric T cell receptors, artificial T cell receptors or chimeric immunoreceptors). Generally, CARs include a binding moiety, an extracellular hinge and spacer element, a transmembrane region and an endodomain that performs signaling functions (Cartellieri et al., *J Biomed Biotechnol* 2010:956304, 2010). In many instances, the binding moiety is an antigen binding fragment of a monoclonal antibody, such as a scFv. Several different endodomains have been used to generate CARs. For example, the endodomain can consist of a signaling chain having an immunoreceptor tyrosine-based activation motif (ITAM), such as CD3ζ or FcεRIγ. In some instances, the endodomain further includes the intracellular portion of at least one additional co-stimulatory domain, such as CD28 and/or CD137.

CTLs expressing CARs can be used to target a specific cell type, such as a tumor cell. Thus, the monoclonal antibodies disclosed herein can be used to engineer CTLs that express a CAR containing an antigen-binding fragment of a mesothelin-specific antibody, thereby targeting the engineered CTLs to mesothelin-expressing tumor cells. Engineered T cells have previously used for adoptive therapy for some types of cancer (see, for example, Park et al., *Mol Ther* 15(4):825-833, 2007). The use of T cells expressing CARs is more universal than standard CTL-based immunotherapy because CTLs expressing CARs are HLA unrestricted and can therefore be used for any patient having a tumor that expressed the target antigen.

Accordingly, provided herein are CARs comprising a mesothelin-specific antibody binding fragment, such as a scFv. Also provided are isolated nucleic acid molecules and vectors encoding the CARs, and host cells, such as CTLs, comprising the nucleic acid molecules or vectors. CTLs expressing CARs comprised of a mesothelin-specific antibody binding fragment can be used for the treatment of cancers that express mesothelin, such as mesothelioma, prostate cancer, lung cancer, stomach cancer, squamous cell carcinoma, pancreatic cancer, cholangiocarcinoma, breast cancer or ovarian cancer. Thus, provided herein are methods of treating a subject with cancer by selecting a subject with a cancer that expresses mesothelin, and administering to the subject a therapeutically effective amount of the CTLs expressing the mesothelin-targeted CARs.

D. Bispecific Antibodies

Bispecific antibodies are recombinant proteins comprised of antigen-binding fragments of two different monoclonal antibodies. Thus, bispecific antibodies bind two different antigens. Bispecific antibodies can be used for cancer immunotherapy by simultaneously targeting both CTLs (such as a CTL receptor component such as CD3) and a tumor antigen. The mesothelin-specific monoclonal antibodies disclosed herein can be used to generate bispecific antibodies that target both mesothelin and CTLs, thereby providing a means to treat mesothelin-expressing cancers.

Provided herein are bispecific monoclonal antibodies comprising a mesothelin-specific monoclonal antibody, or antigen-binding fragment thereof. In some embodiments, the bispecific monoclonal antibody further comprises a monoclonal antibody, or antigen-binding fragment thereof, that specifically binds a component of the T cell receptor, such as CD3. Also provided are isolated nucleic acid molecules and vectors encoding the bispecific antibodies, and host cells comprising the nucleic acid molecules or vectors. Bispecific antibodies comprising a mesothelin-specific antibody, or antigen-binding fragment thereof, can be used for the treatment of cancers that express mesothelin, such as mesothelioma, prostate cancer, lung cancer, stomach cancer, squamous cell carcinoma, pancreatic cancer, cholangiocarcinoma, breast cancer or ovarian cancer. Thus, provided herein are methods of treating a subject with cancer by selecting a subject with a cancer that expresses mesothelin, and administering to the subject a therapeutically effective amount of the mesothelin-targeting bispecific antibody.

The following examples are provided to illustrate certain particular features and/or embodiments. These examples should not be construed to limit the disclosure to the particular features or embodiments described.

EXAMPLES

Example 1: Identification and Characterization of Rabbit Monoclonal Antibodies Specific for Mesothelin This example describes the identification of several rabbit monoclonal antibodies that specifically bind Region II, Region III or a conformational epitope of mesothelin. Characterization of the antibodies confirmed they do not compete for binding with current mesothelin-specific therapeutic antibodies, including SS1P and MORAb-009, which bind Region I of cell-surface mesothelin.

Background

The structure of cell-surface mesothelin is depicted in FIG. 1. All anti-mesothelin therapeutic antibodies generated to date recognize epitopes within the highly immunogenic N-terminal Region I of cell-surface mesothelin, which binds mucin MUC16/CA125. Autoantibodies, or soluble MUC16/CA125 in patients may sequester anti-Region I antibodies, limiting their anti-cancer efficacy. Furthermore, when measuring soluble mesothelin for follow-up of patients in clinical trials treated with MORAb-009 (amatuximab), the FDA approved MesoMark™ kit fails to detect serum mesothelin because it forms a complex with MORAb-009. The epitope of MORAb-009 overlaps that of an anti-Region I antibody used in MesoMark™. Thus, for both diagnostic and therapeutic purposes, it is desirable to identify a high-affinity mesothelin-specific monoclonal antibody that does not bind Region I of mesothelin.

Discovery of Rabbit mAbs Specific for Various Domains of Mesothelin

To identify mesothelin-specific monoclonal antibodies that do not compete for binding with Region I antibodies, 232 rabbit mAbs were selected based on their ELISA binding signal to mesothelin protein. To do this, three mesothelin fragments were produced: Region I (residues 296-390), Region II (residues 391-486) and Region III (residues 487-598) (SEQ ID NO: 7; Kaneko et al., *J Biol Chem* 284: 3739-3749, 2009). The mesothelin fragments were used to select domain-specific rabbit mAbs by ELISA. Of the clones screened, 223 (96%) bound Region I, 5 clones bound Region II and 3 clones bound Region III. In addition, one clone that binds a confirmation sensitive epitope was identified.

Region I, Region II, Region III and confirmation sensitive mAb clones were evaluated by ELISA. ELISA plates were coated with full-length mesothelin, or Region I, Region II or Region III mesothelin fragments. Rabbit hybridoma supernatants were added to the ELISA plates and rabbit mAb binding to mesothelin or its fragments was detected by a goat anti-rabbit IgG light chain-specific HRP conjugate (FIGS. 2A-2D). The results demonstrated that Region I, Region II and Region III specific antibodies were capable of binding their respective mesothelin fragment, as well as full-length mesothelin. Confirmation-sensitive mAb clones bound only full-length mesothelin.

To evaluate binding of the rabbit mAb clones to cell-surface mesothelin, FACS analysis using NCI-H226 cells (a mesothelioma cell line) was performed. NCI-H226 cells ($1\times10^6$) were incubated with rabbit hybridoma supernatant (1:2 dilutions in FACS buffer). The binding of rabbit mAbs to cell surface mesothelin was detected by a goat anti-rabbit IgG PE conjugate. As shown in FIGS. 3A-3D, Region I, Region II, Region III and confirmation-sensitive mAbs clones were all capable of binding cell-surface mesothelin.

Characterization of the High-Affinity mAb Binding Sites

Figure 4:
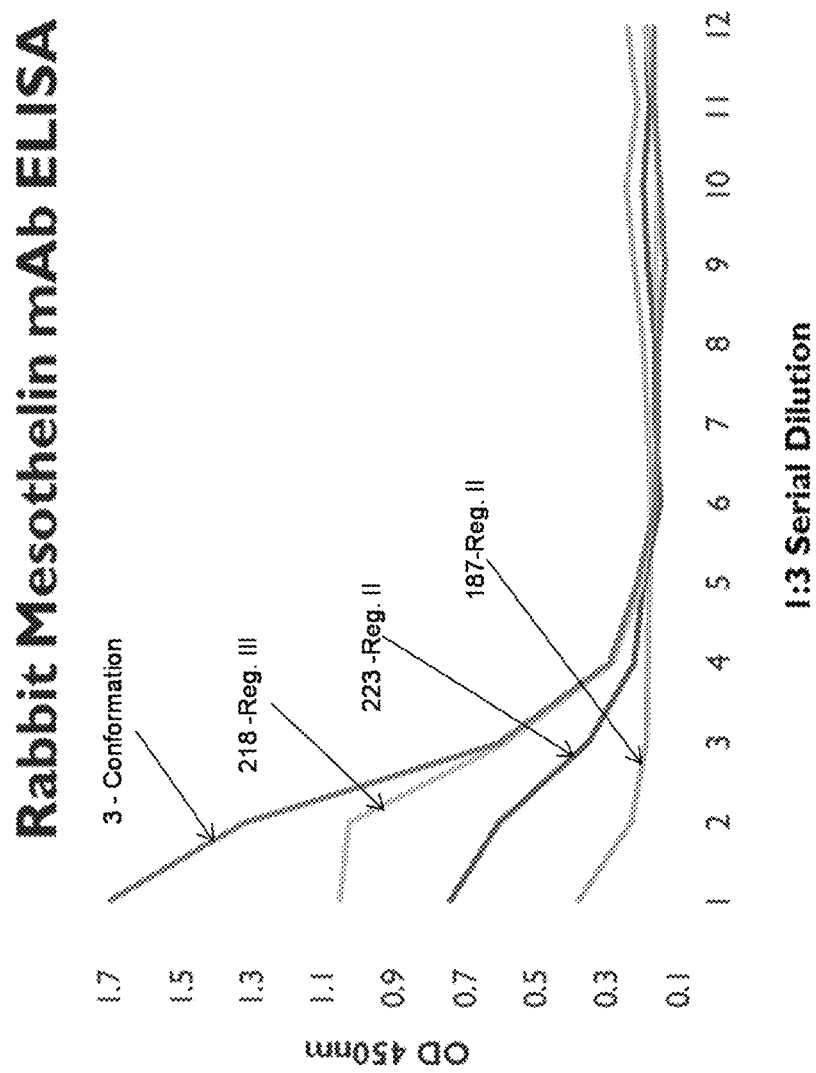
FIG. 4 is a graph showing results of a sandwich ELISA evaluating binding of YP187, YP223, YP218 and YP3 at various dilutions to mesothelin fragments in the presence of the SS1P immunotoxin. ELISA plates were coated with the SS1P immunotoxin (1 µg/ml). Recombinant mesothelin protein (1 µg/ml) was added to the plates. After washing, rabbit mAb supernatant (serially diluted 1:3) was added. Finally, goat anti-rabbit IgG light chain HRP conjugate (1:5000) was added to detect rabbit mAb binding.

Based on the binding data described above, four clones were selected for further analysis:
YP187—Region II binder
YP223—Region II binder
YP218—Region III binder
YP3—confirmation sensitive Sandwich ELISAs were used to determine whether rabbit mAbs bind sites in mesothelin that are different from the SS1P/MORAb-009 (Region I) site. In a first experiment, binding of YP187, YP223, YP218 and YP3 to recombinant mesothelin in the presence of SS1P was evaluated using varying concentrations of each mAb clone. ELISA plates were coated with the SS1P immunotoxin (1 µg/ml). Recombinant mesothelin protein (1 µg/ml) was added to the plates. After washing, rabbit mAb supernatant (serially diluted 1:3) was added and goat anti-rabbit IgG light chain HRP conjugate (1:5000) was used to detect rabbit mAb binding. The results demonstrate that YP187, YP223, YP218 and YP3 all recognize sites different from the SS1P site (FIG. 4).

Figure 5:
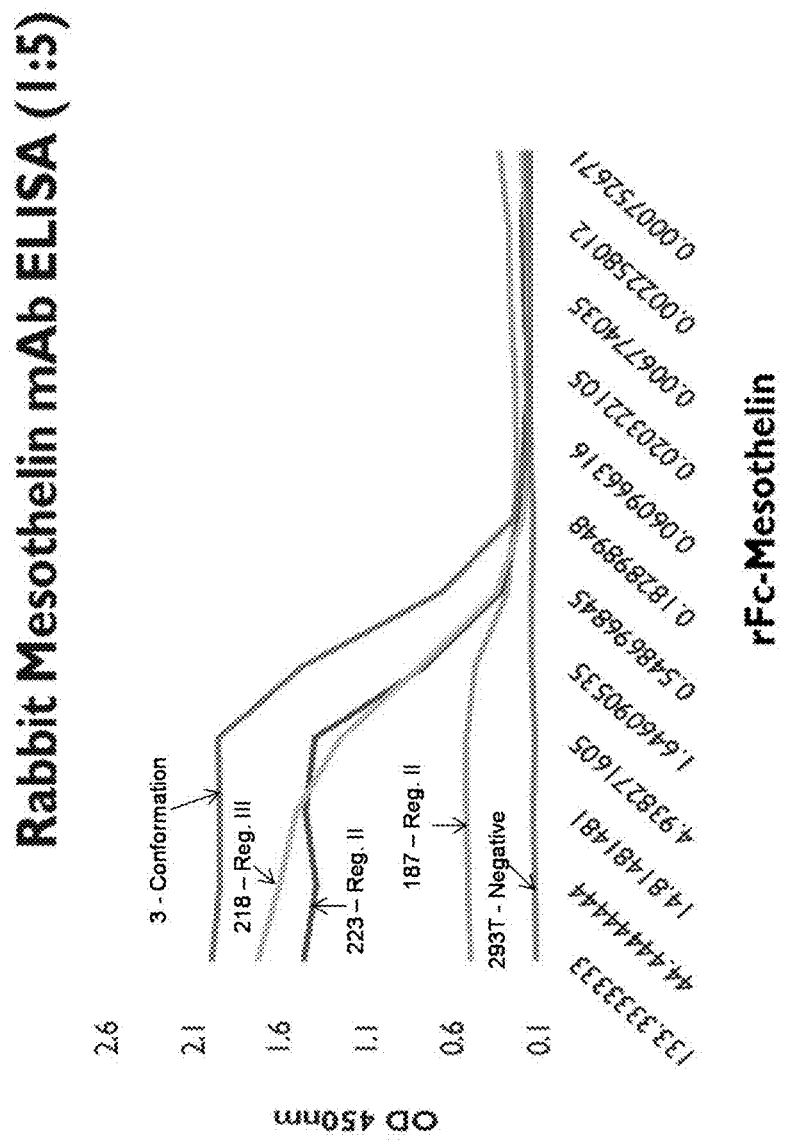
FIG. 5 is a graph showing results of a sandwich ELISA evaluating binding of YP187, YP223, YP218 and YP3 (in the presence of SS1P immunotoxin) to recombinant mesothelin at various concentrations. The SS1P immunotoxin (5 µg/ml) was coated on ELISA plates. Recombinant mesothelin protein, starting from 10 µg/ml, was serially diluted 1:3 and added to the ELISA plates. After washing, rabbit mAb supernatant (1:5) was added. The goat anti-rabbit IgG light chain (1:5000) HRP conjugate was added to detect rabbit mAb binding.

In a second experiment, binding of YP187, YP223, YP218 and YP3 to recombinant mesothelin in the presence of SS1P was evaluated using varying concentrations of recombinant mesothelin. The SS1P immunotoxin (5 µg/ml) was coated on ELISA plates. Recombinant mesothelin protein (starting from 10 µg/ml) was serially diluted 1:3 and added to the ELISA plates. After washing, rabbit mAb supernatant (1:5) was added and goat anti-rabbit IgG light chain (1:5000) HRP conjugate was used to detect rabbit mAb binding. As shown in FIG. 5, YP187, YP223, YP218 and YP3 recognize sites different from the SS1P site. Excluding YP187, all other rabbit mAbs (YP223, YP218 and YP3) bind mesothelin in a dose-dependent manner. The YP187 mAb partially competes with SS1P for mesothelin, indicating that the YP187 site (in Region II) may be close to the SS1P site in Region I.

These results demonstrate that the YP223 (Region II), YP218 (Region III) and YP3 (conformation sensitive) rabbit mAbs do not bind an epitope overlapping the MORAb-009/SS1P site (Region I). The YP187 (Region II) mAb partially competes with SS1P for mesothelin, indicating that the YP187 site may be close to the SS1P site in Region I.

Binding Affinity of Rabbit mAb Clones

Figure 6A:
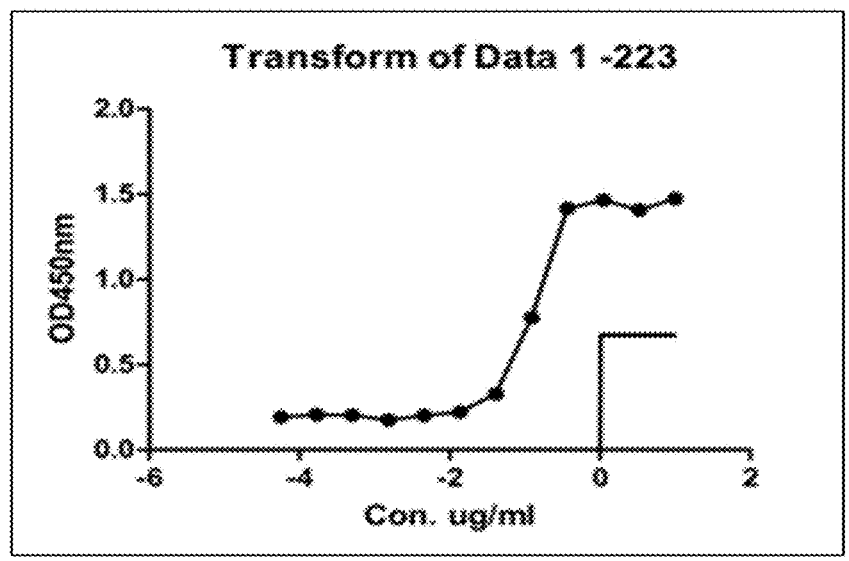
FIGS. 6A-6C are graphs showing mesothelin binding affinity ($K_D$) measurement by ELISA. Various amounts of a rabbit mAbs YP223 (FIG. 6A), YP218 (FIG. 6B) and YP3 (FIG. 6C) were incubated with a fixed amount of mesothelin (1 µg/ml) at room temperature for 1 hour. The plates were then washed and a standard ELISA procedure was carried out to measure rabbit mAb binding on mesothelin. The affinity $K_D$ value was determined by Prism (version 3.02) for Windows (GraphPad software, San Diego, Calif.). $K_D$ values were 0.65 nM, 0.91 nM and 0.42 nM for YP223, YP218 and YP3, respectively.
Figure 6B:
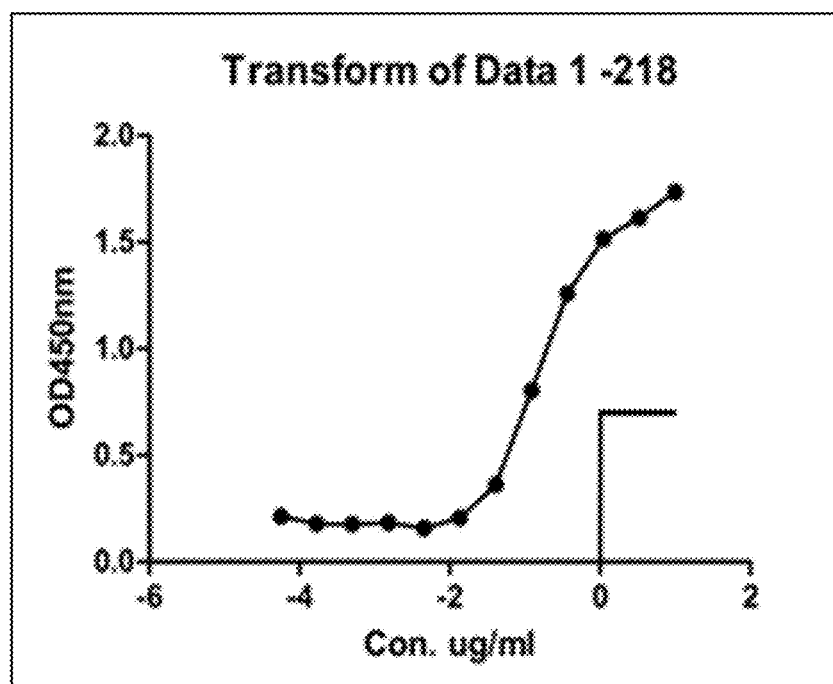
Figure 6C:
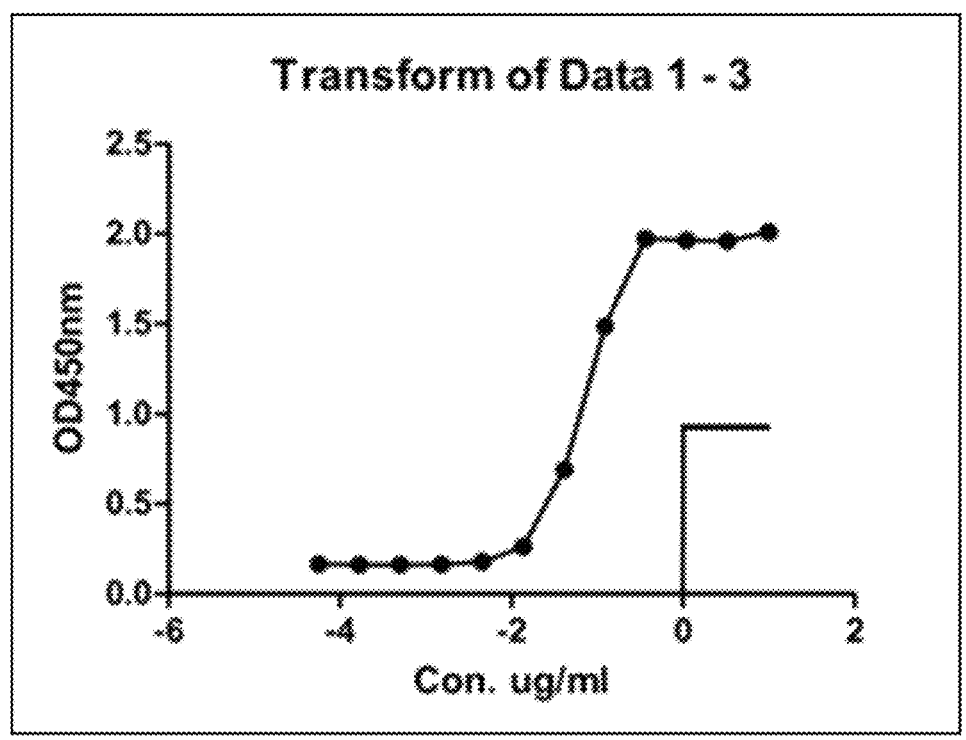

Binding affinity of YP223, YP218 and YP3 for mesothelin was evaluated by ELISA. Various amounts of a rabbit mAb were incubated with a fixed amount of mesothelin (1 µg/ml) at room temperature for 1 hour, after which the plates were washed and a standard ELISA procedure was followed to measure rabbit mAb binding on mesothelin. The affinity Kd value was determined by Prism (version 3.02) for Windows (GraphPad software, San Diego, Calif.). As shown in FIGS. 6A-6C, all rabbit mAbs have high, subnanomolar affinity for mesothelin. In particular, the $K_D$ values were 0.65 nM for YP223, 0.91 nM for YP218 and 0.42 nM for YP3.

Next, a study was performed to evaluate detection of soluble mesothelin proteins in culture supernatant using the rabbit mAb clones. The H9 and K5 cell lines are widely used in xenograft models to evaluate mesothelin-targeted cancer therapy in mice. The K5 cell line expresses a form of mesothelin having a 10-amino acid deletion (residues 411-420) in Region II, while the H9 cell line expresses full-length, wild type mesothelin.

Figure 7A:
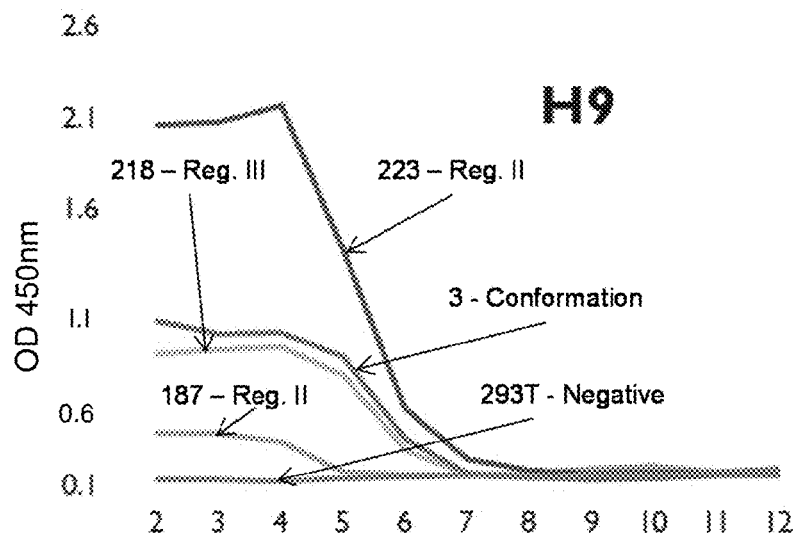
FIGS. 7A-7B are graphs showing detection of soluble mesothelin in culture supernatant by sandwich ELISA. ELISA plates were coated with SS1P (5 µg/ml). H9 (FIG. 7A) or K5 (FIG. 7B) culture supernatant (serially diluted 1:3) was added. After washing, rabbit mAb culture supernatant (1:5) was added. Goat anti-rabbit light chain specific HRP conjugate (1:5000) was used to detect rabbit mAb binding.
Figure 7B:
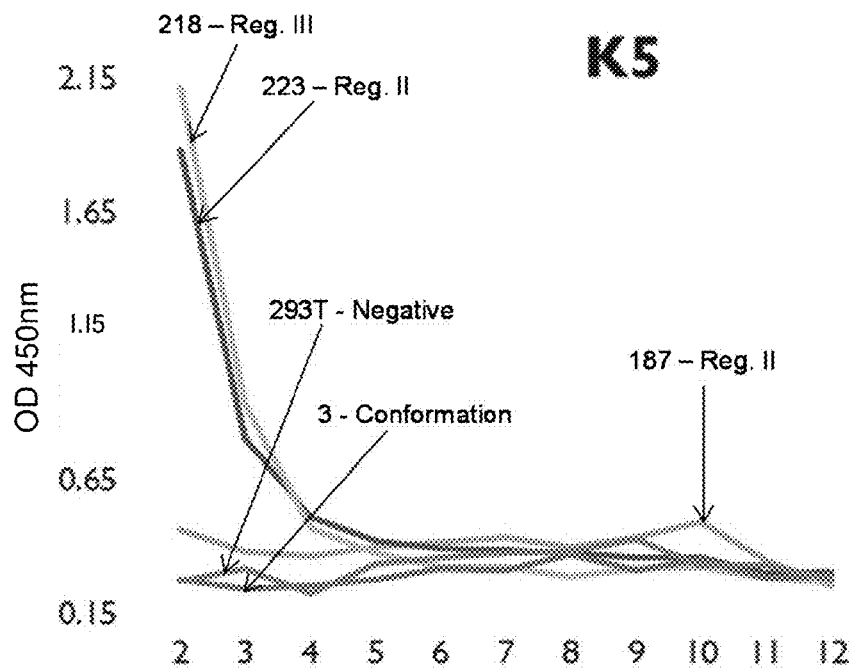

ELISA plates were coated with SS1P (5 µg/ml). H9 or K5 culture supernatant (serially diluted 1:3) was added. After washing, rabbit mAb culture supernatant (1:5) was added. Goat anti-rabbit light chain-specific HRP conjugate (1:5000) was used to detect rabbit mAb binding (FIGS. 7A-7B).

The Region II, Region III, and conformation sensitive mAbs bound wild type mesothelin in the H9 cell line. However, both Region II (YP223) and Region III (YP218) mAbs, but not the conformation sensitive (YP3) mAb, weakly bound the mutant mesothelin with a 10-amino acid deletion expressed by the K5 cell line, indicating YP3 recognizes a native conformation specific to the conformation of wild type mesothelin.

Detection of Soluble Mesothelin by Sandwich ELISA

Figure 10:
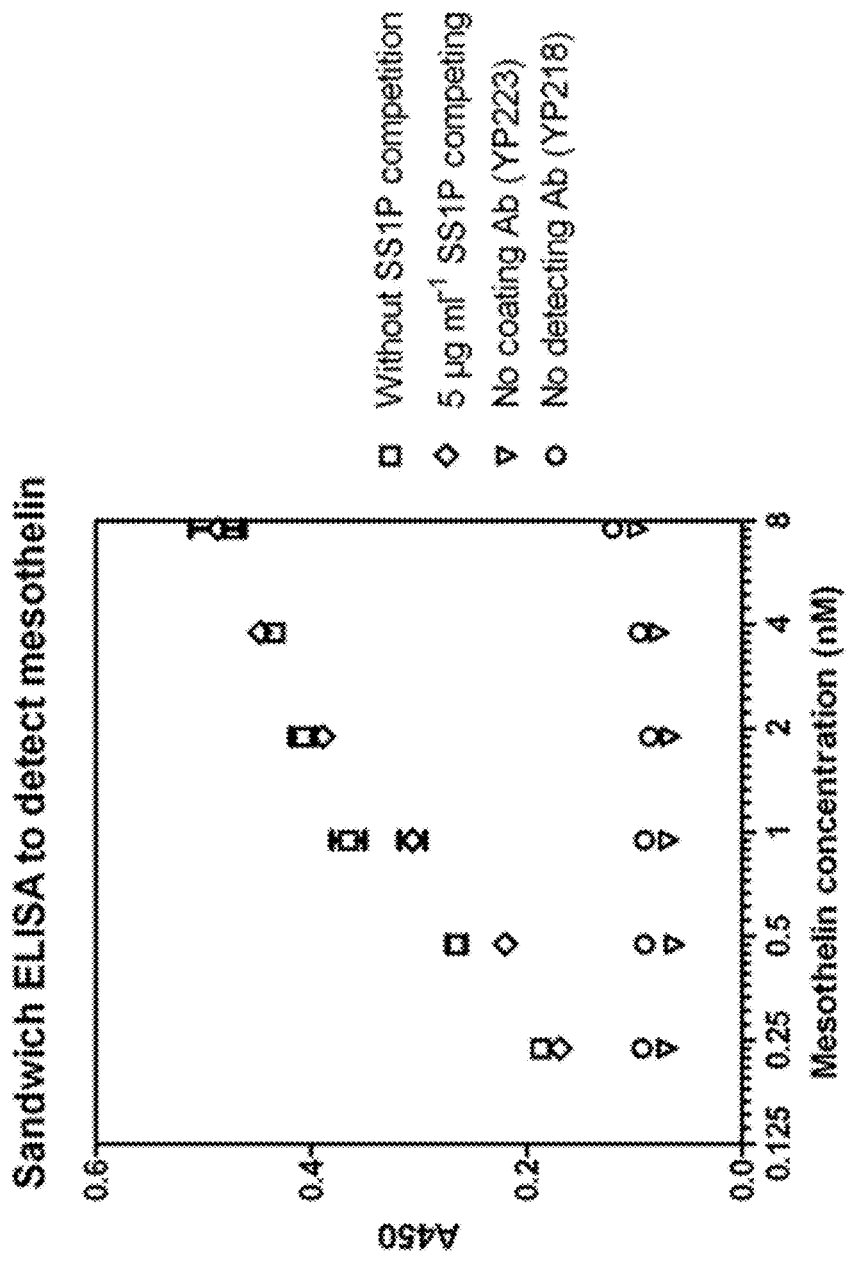
FIG. 10 is a graph showing detection of soluble mesothelin in the presence of SS1P immunotoxin. This assay utilized YP223 (Region II binder) and YP218 (Region III binder) in a sandwich ELISA. Soluble mesothelin was detected even in the presence of SS1P immunotoxin.

Nunc MaxiSorp 96-well flat-bottomed plates were coated overnight with 5 µg/ml of YP223 (Region II binder) in PBS. Purified mesothelin-Fc fusion protein was diluted at different concentrations (from 0.25 to 8 nM) in ELISA buffer (0.01% Tween 20, 10% Pierce SuperBlock) and incubated on a plate for 1 hour at room temperature. For SS1P competition assay, 5 µg/mL SS1P was pre-incubated with mesothelin-Fc fusion protein for 1 hour at room temperature and then the mixtures (SS1P and mesothelin) were added into the plate. To detect soluble mesothelin, plates were then incubated with 5 µg/mL biotinylated YP218 (Region III binder) for 1 hour at room temperature; subsequently a 1:2000 dilution of Streptavidin—HRP (Invitrogen) was added to the plate for 1 hour at room temperature. The plates were washed four times between each coating. Visualization was achieved with 3,3',5,5'-tetramethylbenzidine detection reagent (KPL) and absorbance was read at 450 nm with SpectraMax Plus plate reader (Molecular Devices). The results are shown in FIG. 10.

These results demonstrate the establishment of a new sandwich ELISA method using the YP223 and YP218 rabbit antibodies to measure soluble mesothelin protein in the presence of the SS1P immunotoxin. The presence of SS1P does not affect the binding of YP223 or YP218 to mesothelin. The new sandwich ELISA assay is highly sensitive because (1) its $EC_{50}$ is around 0.5 nM and (2) it can detect 0.2 nM of soluble mesothelin protein.

Example 2: High-Affinity Rabbit mAB Specific for Region I Mesothelin

This example describes the identification and characterization of a rabbit mAb clone that binds Region I of native mesothelin in cancer cells and tissues with high affinity and specificity.

As described in Example 1, 223 rabbit mAb clones were identified that bound mesothelin Region I (residues 296-390). Among the high-affinity binders in this group, YP158 was identified. YP158 is highly specific for mesothelin in cancer cells and tissues.

Figure 9:
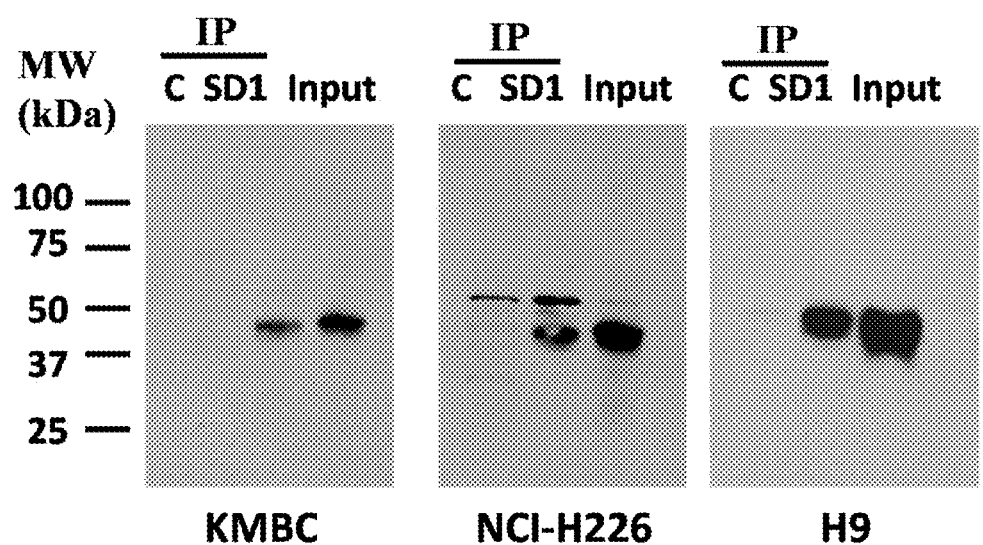
FIG. 9 shows immunoprecipitation of endogenous mesothelin protein in A431/H9 (forced expression of mesothelin in epidermoid carcinoma A431 cells), NCI-H226 (mesothelioma) and KMBC (cholangiocarcinoma) cell extracts. A human mAb (hAb) to mesothelin was used to pull down endogenous mesothelin protein in the cell lysate. YP158 was used to probe native mesothelin in pulldown proteins. C: an irrelevant VH single-domain human Fc fusion; IP: immunoprecipitation; Input: western blot on whole cell lysates before immunoprecipitation.

To evaluate binding of YP158 to human cancer cells, immunoblot analysis using a panel of liver cancer cell lines and cancer specimens was carried out. As shown in FIGS. 8A-8B, YP158 is capable of detecting native mesothelin in cancer cells. The capacity of YP158 to detect native mesothelin in immunoprecipitated complexes was next evaluated. In this experiment, immunoprecipitation of endogenous mesothelin protein in A431/H9 (forced expression of mesothelin in epidermoid carcinoma A431 cell line), NCI-H226 (mesothelioma) and KMBC (cholangiocarcinoma) cell extracts was carried out. A human mAb to mesothelin was used to immunoprecipitate endogenous mesothelin protein in the cell lysate. YP158 was used to probe native mesothelin in the immunoprecipitated proteins (FIG. 9).

These results demonstrate that YP158 binds native mesothelin protein in cancer cells and tissues with very high affinity and specificity.

Example 3: Generation and Characterization of CD22-Specific Immunotoxins

Recombinant immunotoxins were generated using YP3, YP218, YP223 and YP187 scFv fused to *Pseudomonas* exotoxin fragment PE38 (SEQ ID NO: 2), following standard techniques. Briefly, in each immunotoxin construct, the antibody VH domain was fused to the VL domain using a linker sequence encoding the peptide $(Gly_4Ser)_3$ (amino acid residues 125-139 of SEQ ID NO: 31). The antibody VL domain was fused to PE38 using a short linker sequence (ASGG; amino acid residues 251-254 of SEQ ID NO: 31). The nucleotide and amino acid sequences of the YP218scFv-PE38, humanized YP213scFv-PE38, YP223scFv-PE38, YP3scFv-PE38 and YP187scFv-PE38 immunotoxins are set forth herein as SEQ ID NOs: 30-39.

Binding affinity of the YP3scFv-PE38, YP218scFv-PE38 and YP223scFv-PE38 immunotoxins for a panel of tumor cells expressing mesothelin was evaluated by flow cytometry. Cytotoxicity of the YP3scFv-PE38, YP218scFv-PE38 and YP223scFv-PE38 immunotoxins was also evaluated on the mesothelin-expressing tumor cells. Mesothelin-specific immunotoxin SS1P was used as a positive control and the HB21-PE40 immunotoxin was used as a negative control. The results are summarized in Table 6 below. All three immunotoxins bound the mesothelin-positive cell lines with varying affinities, with YP218scFv-PE38 exhibiting the greatest affinity. YP218scFv-PE38 also induced the greatest cytotoxicity of mesothelin-expressing tumor cells.

TABLE 6

Summary of cytotoxicity and affinity of anti-mesothelin immunotoxins on mesothelin-expressing cells

| Cell line | | control | SS1P | YP3ScFv-PE38 | YP218ScFv-PE38 | YP223ScFv-PE38 | HB21-PE40 |
|---|---|---|---|---|---|---|---|
| H9 | IC50 (ng ml$^{-1}$) | >1000 | 0.076 | 1.19 | 0.88 | 44.34 | |
| | Kd (nM) | | | 4.82 | 3.74 | 6.56 | 46.18 |
| OVCAR8 | IC50 (ng ml$^{-1}$) | >1000 | 1.82 | 2.47 | 3.57 | 17.92 | |
| | Kd (nM) | | | 0.60 | 1.39 | 1.74 | 9.93 |
| NCI-ADR-RES | IC50 (ng ml$^{-1}$) | >1000 | 1.20 | 2.27 | 3.28 | 177.12 | 0.12 |
| | Kd (nM) | | | 1.41 | 3.33 | 3.25 | ≥22.86 | 10.82 |
| NCI-H226 | IC50 (ng ml$^{-1}$) | >1000 | 5.29 | 10.11 | 1.58 | 33.73 | |
| | Kd (nM) | | | 1.49 | 5.82 | ≥3.216 | ≥52.52 | |
| L55 | IC50 (ng ml$^{-1}$) | >1000 | 5.89 | 21.89 | 15.81 | 345.53 | 0.57 |
| | Kd (nM) | | | 1.04 | 2.62 | 2.37 | 10.05 | 9.74 |
| EKVX | IC50 (ng ml$^{-1}$) | >500 | 55.38 | 24.86 | 75.54 | >300 | 0.21 |
| | Kd (nM) | | | 1.7 | 1.20 | 1.16 | >157 | 6.28 |

TABLE 6-continued

Summary of cytotoxicity and affinity of anti-mesothelin immunotoxins on mesothelin-expressing cells

| Cell line | | control | SS1P | YP3ScFv-PE38 | YP218ScFv-PE38 | YP223ScFv-PE38 | HB21-PE40 |
|---|---|---|---|---|---|---|---|
| NCI-H322M | IC50 (ng ml$^{-1}$) | >300 | 4.02 | 3.42 | 12.73 | >1000 | 0.31 |
| | Kd (nM) | | 0.44 | 1.04 | 2.02 | 8.65 | 6.05 |
| KMBC | IC50 (ng ml$^{-1}$) | >1000 | 3.39 | 14.11 | 11.91 | 151.56 | |
| | Kd (nM) | | 2.15 | 0.42 | 1.40 | 6.41 | |
| KMCH | IC50 (ng ml$^{-1}$) | >1000 | 7.23 | 14.87 | 39.86 | 215.01 | |
| | Kd (nM) | | 1.26 | 0.68 | 1.72 | 7.58 | |
| Mz-Cha-1 | IC50 (ng ml$^{-1}$) | >1000 | 21.57 | >1000 | >1000 | >1000 | |
| | Kd (nM) | | 1.30 | 4.60 | 3.99 | 29.50 | |
| M30 | IC50 (ng ml$^{-1}$) | >1000 | 7.13 | 16.01 | 18.74 | >1000 | 0.51 |
| | Kd (nM) | | 0.49 | 1.67 | 1.98 | 12.13 | 13 |
| YOU | IC50 (ng ml$^{-1}$) | >1000 | 13.00 | 21.67 | 39.80 | 231.42 | 0.27 |
| | Kd (nM) | | 1.48 | 3.7 | 6.80 | 27.68 | 24.7 |
| A431* | IC50 (ng ml$^{-1}$) | >100 | >300 | >300 | >300 | >300 | |
| H226-GL | IC50 (ng ml$^{-1}$) | >1000 | 1.99 | 1.73 | 0.74 | 51.39 | 0.22 |

*mesothelin negative

Figure 11:
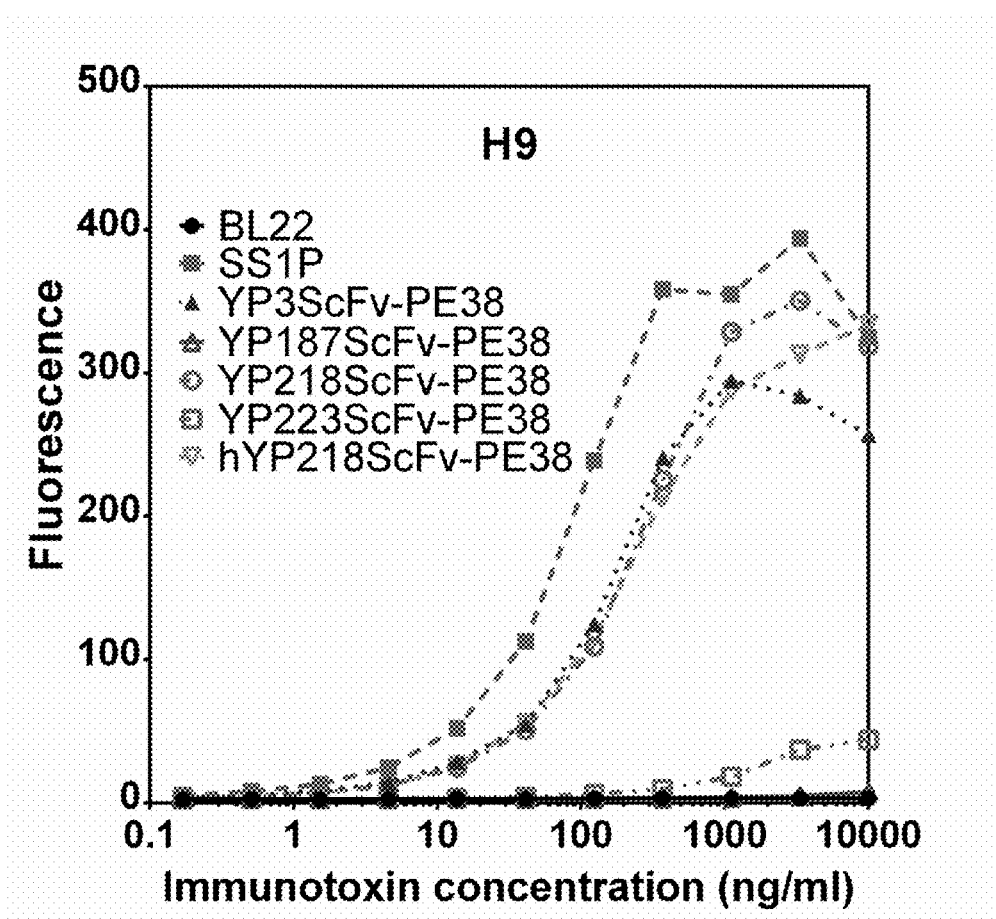
FIG. 11 is a graph showing the binding affinity of anti-mesothelin immunotoxins against mesothelin expressing cells. The binding of immunotoxins on these cell lines was measured by flow cytometry and indicated by fluorescence intensity. hYP218scFv-PE38 is humanized YP218scFv-PE38. The binding affinity of humanized YP218 Fv for H9 cells is similar to that of the original rabbit YP218 Fv ($K_d$=~4 nM).

In addition, binding affinity of YP3scFv-PE38, YP187scFv-PE38, YP218scFv-PE38, its humanized version hYP218scFv-PE38, and YP223scFv-PE38 for H9 cells was evaluated by flow cytometry. The results are shown in FIG. 11 and summarized below in Table 7. Humanization of the YP218scFv-PE38 immunotoxin did not significantly alter its binding affinity for mesothelin-positive H9 cells.

TABLE 7

Binding affinity of immunotoxins for H9 cells

| Immunotoxin | Kd (nM) |
|---|---|
| SS1P | 1.3 |
| YP3ScFv-PE38 | 2.352 |
| YP218ScFv-PE38 | 3.865 |
| YP223ScFv-PE38 | 25.21 |
| YP187ScFv-PE38 | >158 |
| hYP218ScFv-PE38 | 3.607 |

Figure 12:
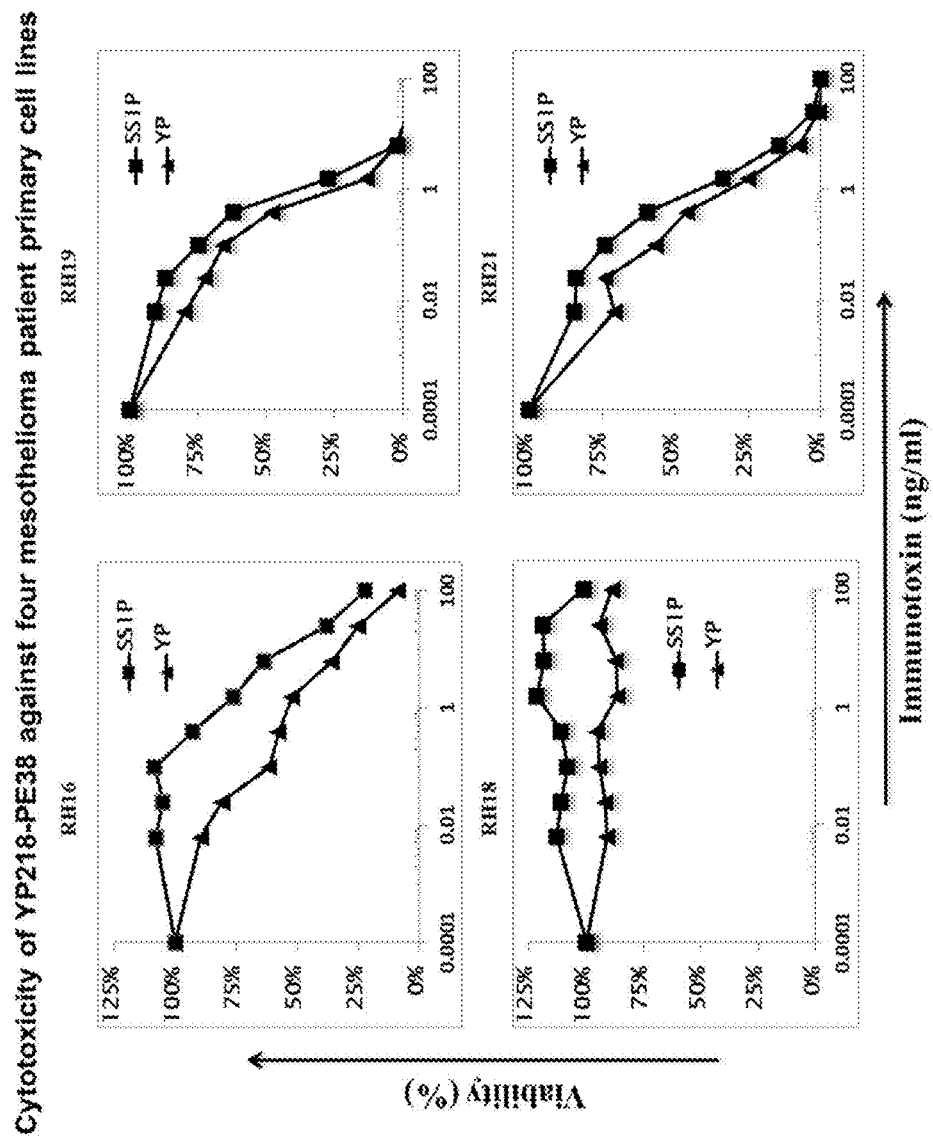
FIG. 12 is a series of graphs showing cytotoxicity of YP218scFv-PE38 against four malignant mesothelioma patient primary cell lines. Out of the four primary cell lines (RH16, RH18, RH19 and RH21), three were sensitive to the anti-mesothelin immunotoxins. Of the three primary lines which were sensitive (RH16, RH19 and RH21), YP218scFv-PE38 was 2- to 5-fold more potent than SS1P.

Next, cytotoxicity of YP218scFv-PE38 against four malignant mesothelioma patient primary cell lines was compared with cytotoxicity of the SS1P immunotoxin. Of the four primary cell lines (RH16, RH18, RH19 and RH21), three were sensitive to the anti-mesothelin immunotoxins. Of the three primary lines that were sensitive (RH16, RH19 and RH21), YP218scFv-PE38 was 2- to 5-fold more potent than SS1P (see FIG. 12 and Table 8).

TABLE 8

Cytotoxicity of YP218scFv-PE38 against four mesothelioma patient primary cell lines

| Malignant Mesothelioma Patient Cells | SS1P IC$_{50}$ (ng/ml) | YP218scFv-PE38 IC$_{50}$ (ng/ml) |
|---|---|---|
| RH16 | 10.4 | 2.0 |
| RH18 | >100 | >100 |
| RH19 | 0.63 | 0.33 |
| RH21 | 0.73 | 0.23 |

Figure 13:
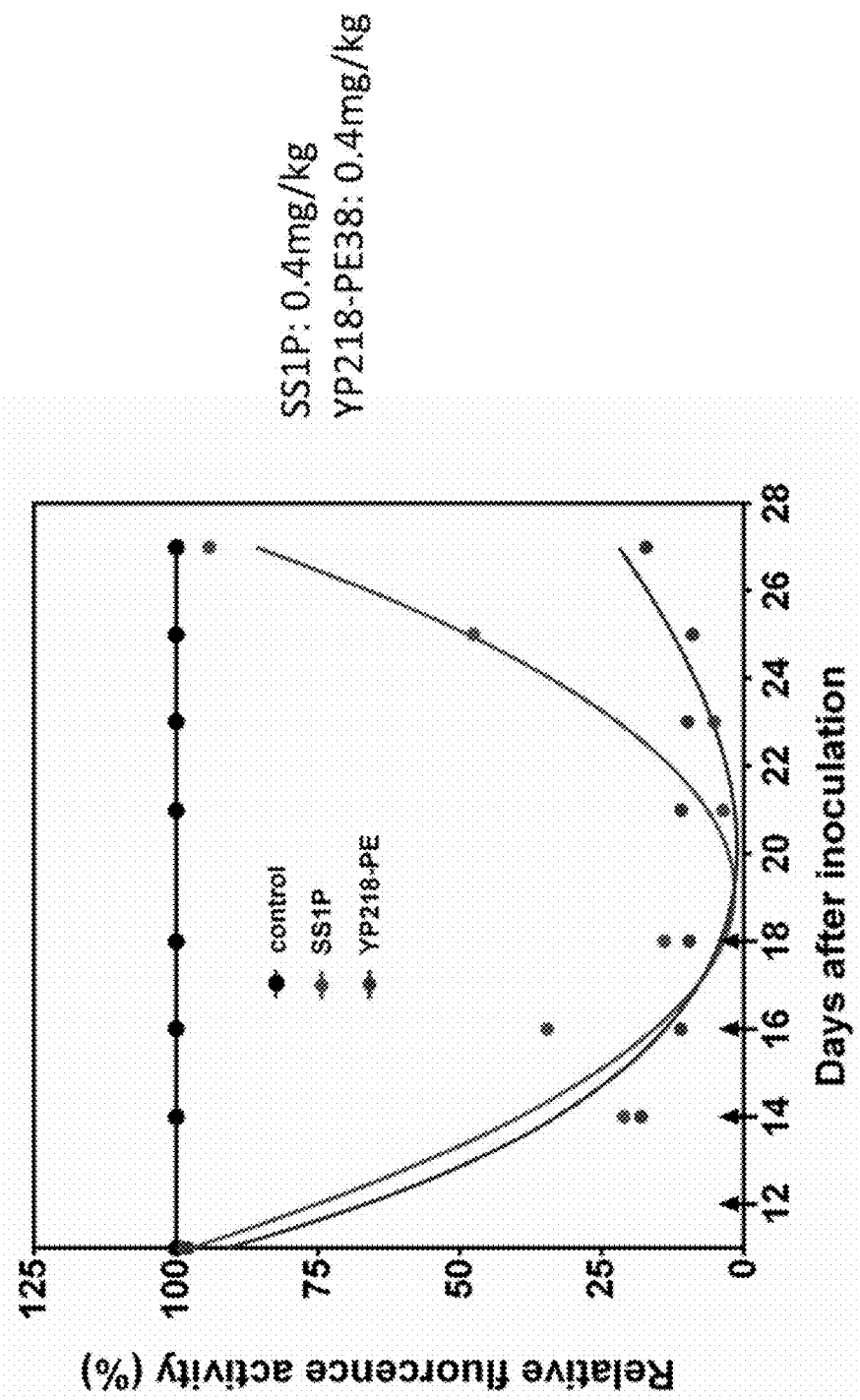
FIG. 13 is a graph showing that the YP218scFv-PE38 immunotoxin was more potent than SS1P in a human malignant mesothelioma model. Six-week female BALB/c nu/nu mice were intraperitoneally inoculated with $3\times10^6$ NCI-H226 mesothelioma cells that stably express high levels of Luc/GFP. Mice were intraperitoneally administered with SS1P (0.4 mg/kg), YP218scFv-PE38 (0.4 mg/kg) or vehicle (PBS) at days 12, 14, 16 and 18. Tumor growth was measured by bioluminescence photometry three times a week. Relative bioluminescence activity was normalized based on the control (vehicle) group. The arrows indicate injections. N=5/group.

The YP218scFv-PE38 was further evaluated in the NCI-H226 human mesothelioma model in nude mice. Six-week female BALB/c nu/nu mice were intraperitoneally inoculated with 3×10$^6$ NCI-H226 mesothelioma cells that stably express high levels of Luc/GFP. Mice were intraperitoneally administered with SS1P (0.4 mg/kg), YP218scFv-PE38 (0.4 mg/kg) or vehicle (PBS) at days 12, 14, 16 and 18. Both SS1P and YP218-PE38 immunotoxins inhibited tumor growth effectively during the treatment. However, remnant mesothelioma tumor cells caused relapse quickly after the SS1P treatment was finished, while the relapse of mesothelioma in the YP218scFv-PE38 group was significantly slower (FIG. 13). Two out of five mice in the YP218scFv-PE38 group were almost tumor free while all the mice in the SS1P group had tumors on Day 25 and Day 27.

Example 4: Mesothelin-Specific Monoclonal Antibodies for Detecting Cancer in a Subject or Confirming the Diagnosis of Cancer in a Subject This example describes the use of mesothelin-specific monoclonal antibodies, such as the rabbit monoclonal antibodies disclosed herein or humanized or labeled versions of these antibodies, for the detection of cancer in a subject. This example further describes the use of these antibodies to confirm the diagnosis of cancer in a subject.

A blood sample is obtained from the patient diagnosed with, or suspected of having a mesothelin-positive cancer (i.e., a cancer that overexpresses mesothelin, such as mesothelioma, prostate cancer, lung cancer, stomach cancer, squamous cell carcinoma, pancreatic cancer, cholangiocarcinoma, breast cancer or ovarian cancer). A blood sample taken from a patient that does not have cancer can be used as a control. An ELISA is performed to detect the presence of soluble mesothelin in the blood sample. Proteins present in the blood samples (the patient sample and control sample) are immobilized on a solid support, such as a 96-well plate, according to methods well known in the art (see, for example, Robinson et al., Lancet 362:1612-1616, 2003). Following immobilization, mesothelin-specific monoclonal antibody directly labeled with a fluorescent marker is applied to the protein-immobilized plate. The plate is washed in an appropriate buffer, such as PBS, to remove any unbound antibody and to minimize non-specific binding of antibody. Fluorescence can be detected using a fluorometric plate reader according to standard methods. An increase in fluorescence intensity of the patient sample, relative to the control sample, indicates the anti-mesothelin antibody specifically bound proteins from the blood sample, thus detecting the presence of mesothelin protein in the sample. Detection of mesothelin protein in the patient sample indicates the patient has a mesothelin-positive cancer, or confirms diagnosis of cancer in the subject.

Example 5: Mesothelin-Specific Monoclonal Antibodies for the Treatment of Cancer This example describes the use of mesothelin-specific monoclonal antibodies, such as the rabbit monoclonal antibodies disclosed herein or humanized versions of these antibodies, for the treatment of cancers that exhibit overexpression of mesothelin (referred to herein as a "mesothelin-positive" cancer), including, but not limited to mesothelioma, prostate cancer, lung cancer, stomach cancer, squamous cell carcinoma, pancreatic cancer, cholangiocarcinoma, breast cancer or ovarian cancer. Patients diagnosed with a mesothelin-positive cancer can be treated according to standard procedures in the art (see, for example, Hassan et al., *Proc. Am. Soc. Clin. Oncol.* 21:29a, 2002; Kreiman et al., *Proc. Am. Soc. Clinl Oncol.* 21:22b, 2002).

In this example, patients diagnosed with a mesothelin-positive cancer are administered an immunoconjugate comprising a mesothelin-specific monoclonal antibody linked to *Pseudomonas* exotoxin (PE). Preparation of PE immunoconjugates has been described (see, for example, U.S. Pat. No. 7,081,518 and U.S. Patent Application Publication No. 2005/0214304). In some patients, the immunoconjugate is administered by intravenous bolus injection every other day for a total of three to six doses. In other patients, the immunoconjugate is administered by continuous intravenous infusion over the course of ten days. The dose of immunoconjugate administered to a patient varies depending on the weight and gender of the patient, and mode and time course of administration. Following treatment, patients are evaluated for cancer progression (including tumor growth and metastasis) and other clinical signs of illness.

In view of the many possible embodiments to which the principles of the disclosed invention may be applied, it should be recognized that the illustrated embodiments are only preferred examples of the invention and should not be taken as limiting the scope of the invention. Rather, the scope of the invention is defined by the following claims. We therefore claim as our invention all that comes within the scope and spirit of these claims.

---

The invention claimed is:

1. An isolated monoclonal antibody that binds mesothelin, wherein:
   (i) the variable heavy (VH) domain of the antibody comprises a complementarity determining region (CDR) 1, a CDR2 and a CDR3 from SEQ ID NO: 13; and the variable light (VL) domain of the antibody comprises a CDR1, a CDR2 and a CDR3 from SEQ ID NO: 15;
   (ii) the VH domain of the antibody comprises a CDR1, a CDR2 and a CDR3 from SEQ ID NO: 9; and the VL domain of the antibody comprises a CDR1, a CDR2 and a CDR3 from SEQ ID NO: 11;
   (iii) the VH domain of the antibody comprises a CDR1, a CDR2 and a CDR3 from SEQ ID NO: 17; and the VL domain of the antibody comprises a CDR1, a CDR2 and a CDR3 from SEQ ID NO: 19;
   (iv) the VH domain of the antibody comprises a CDR1, a CDR2 and a CDR3 from SEQ ID NO: 21, or comprises a CDR1, a CDR2 and a CDR3 from SEQ ID NO: 29; and the VL domain of the antibody comprises a CDR1, a CDR2 and a CDR3 from SEQ ID NO: 23; or
   (v) the VH domain of the antibody comprises a CDR1, a CDR2 and a CDR3 from SEQ ID NO: 25; and the VL domain of the antibody comprises a CDR1, a CDR2 and a CDR3 from SEQ ID NO: 27.

2. The isolated monoclonal antibody of claim 1, wherein:
   (i) the VH domain of the antibody comprises a CDR1 set forth as amino acid residues 31-36 of SEQ ID NO: 13, a CDR2 set forth as amino acid residues 51-68 of SEQ ID NO: 13 and a CDR3 set forth as amino acid residues 100-112 of SEQ ID NO: 13; and the VL domain of the antibody comprises a CDR1 set forth as amino acid residues 24-34 of SEQ ID NO: 15, a CDR2 set forth as amino acid residues 50-56 of SEQ ID NO: 15 and a CDR3 set forth as amino acid residues 89-101 of SEQ ID NO: 15;

(ii) the VH domain of the antibody comprises a CDR1 set forth as amino acid residues 31-36 of SEQ ID NO: 9, a CDR2 set forth as amino acid residues 51-67 of SEQ ID NO: 9 and a CDR3 set forth as amino acid residues 100-111 of SEQ ID NO: 9; and the VL domain of the antibody comprises a CDR1 set forth as amino acid residues 24-34 of SEQ ID NO: 11, a CDR2 set forth as amino acid residues 50-56 of SEQ ID NO: 11 and a CDR3 set forth as amino acid residues 89-100 of SEQ ID NO: 11;

(iii) the VH domain of the antibody comprises a CDR1 set forth as amino acid residues 31-35 of SEQ ID NO: 17, a CDR2 set forth as amino acid residues 50-67 of SEQ ID NO: 17 and a CDR3 set forth as amino acid residues 99-108 of SEQ ID NO: 17; and the VL domain of the antibody comprises a CDR1 set forth as amino acid residues 24-34 of SEQ ID NO: 19, a CDR2 set forth as amino acid residues 50-56 of SEQ ID NO: 19 and a CDR3 set forth as amino acid residues 89-100 of SEQ ID NO: 19;

(iv) the VH domain of the antibody comprises a CDR1 set forth as amino acid residues 31-35 of SEQ ID NO: 21, a CDR2 set forth as amino acid residues 50-66 of SEQ ID NO: 21 and a CDR3 set forth as amino acid residues 98-113 of SEQ ID NO: 21, or comprises a CDR1 set forth as amino acid residues 31-36 of SEQ ID NO: 29, a CDR2 set forth as amino acid residues 51-68 of SEQ ID NO: 29 and a CDR3 set forth as amino acid residues 100-112 of SEQ ID NO: 29; and the VL domain of the antibody comprises a CDR1 set forth as amino acid residues 24-34 of SEQ ID NO: 23, a CDR2 set forth as amino acid residues 50-56 of SEQ ID NO: 23 and a CDR3 set forth as amino acid residues 89-100 of SEQ ID NO: 23; or (v) the VH domain of the antibody comprises a CDR1 set forth as amino acid residues 30-35 of SEQ ID NO: 25, a CDR2 set forth as amino acid residues 50-67 of SEQ ID NO: 25 and a CDR3 set forth as amino acid residues 99-109 of SEQ ID NO: 25; and the VL domain of the antibody comprises a CDR1 set forth as amino acid residues 24-34 of SEQ ID NO: 27, a CDR2 set forth as amino acid residues 50-56 of SEQ ID NO: 27 and a CDR3 set forth as amino acid residues 89 102 of SEQ ID NO: 27.

3. The isolated monoclonal antibody of claim 1, wherein:
(i) the amino acid sequence of the VH domain is at least 90% or at least 95% identical to SEQ ID NO: 13; and the amino acid sequence of the VL domain is at least 90% or at least 95% identical to SEQ ID NO: 15;
(ii) the amino acid sequence of the VH domain is at least 90% or at least 95% identical to SEQ ID NO: 9; and the amino acid sequence of the VL domain is at least 90% or at least 95% identical to SEQ ID NO: 11;
(iii) the amino acid sequence of the VH domain is at least 90% or at least 95% identical to SEQ ID NO: 17; and the amino acid sequence of the VL domain is at least 90% or at least 95% identical to SEQ ID NO: 19;
(iv) the amino acid sequence of the VH domain is at least 90% or at least 95% identical to SEQ ID NO: 21 or SEQ ID NO: 29; and the amino acid sequence of the VL domain is at least 90% or at least 95% identical to SEQ ID NO: 23; or
(v) the amino acid sequence of the VH domain is at least 90% or at least 95% identical to SEQ ID NO: 25; and the amino acid sequence of the VL domain is at least 90% or at least 95% identical to SEQ ID NO: 27.

4. The isolated monoclonal antibody of claim 1, wherein:
(i) the VH domain of the antibody comprises SEQ ID NO: 13 and the VL domain of the antibody comprises SEQ ID NO: 15;
(ii) the VH domain of the antibody comprises SEQ ID NO: 9 and the VL domain of the antibody comprises SEQ ID NO: 11;
(iii) the VH domain of the antibody comprises SEQ ID NO: 17 and the VL domain of the antibody comprises SEQ ID NO: 19;
(iv) the VH domain of the antibody comprises SEQ ID NO: 21 or SEQ ID NO: 29 and the VL domain of the antibody comprises SEQ ID NO: 23; or
(v) the VH domain of the antibody comprises SEQ ID NO: 25 and the VL domain of the antibody comprises SEQ ID NO: 27.

5. The isolated monoclonal antibody of claim 1, wherein the antibody is a Fab fragment, a Fab' fragment, a F(ab)'$_2$ fragment, a single chain variable fragment (scFv), or a disulfide stabilized variable fragment (dsFv).

6. The isolated monoclonal antibody of claim 1, wherein the antibody is an IgG.

7. The isolated monoclonal antibody of claim 1, wherein the antibody is chimeric, synthetic, or humanized.

8. The isolated monoclonal antibody of claim 1, wherein the antibody further comprises a label.

9. The isolated monoclonal antibody of claim 8, wherein the label is a fluorescent, enzymatic, or radioactive label.

10. An isolated immunoconjugate comprising the monoclonal antibody of claim 1 and an effector molecule.

11. The isolated immunoconjugate of claim 10, wherein the effector molecule is a toxin.

12. The isolated immunoconjugate of claim 11, wherein the toxin is *Pseudomonas* exotoxin or a variant thereof.

13. The isolated immunoconjugate of claim 12, wherein the *Pseudomonas* exotoxin or a variant thereof comprises the amino acid sequence of any one of SEQ ID NOs: 1-6.

14. The isolated immunoconjugate of claim 10, comprising the amino acid sequence of SEQ ID NO: 31, SEQ ID NO: 33, SEQ ID NO: 35, SEQ ID NO: 37 or SEQ ID NO: 39.

15. A composition comprising a therapeutically effective amount of the antibody of claim 1 in a pharmaceutically acceptable carrier.

16. A method of detecting mesothelin in a sample, comprising:
contacting the sample with the monoclonal antibody of claim 1;
detecting binding of the monoclonal antibody to the sample; and
detecting mesothelin in the sample if an increase in binding of the monoclonal antibody to the sample is detected, as compared to binding of the monoclonal antibody to a control sample.

17. The method of claim 16, wherein the sample comprises a mesothelioma, prostate cancer, lung cancer, stomach cancer, squamous cell carcinoma, pancreatic cancer, cholangiocarcinoma, breast cancer or ovarian cancer tumor biopsy.

18. An isolated nucleic acid molecule encoding the monoclonal antibody of claim 1.

19. The isolated nucleic acid molecule of claim 18, wherein:
   (i) the nucleotide sequence encoding the VH domain of the monoclonal antibody comprises SEQ ID NO: 12, SEQ ID NO: 8, SEQ ID NO: 16, SEQ ID NO: 20, SEQ ID NO: 28 or SEQ ID NO: 24;
   (ii) the nucleotide sequence encoding the VL domain of the monoclonal antibody comprises SEQ ID NO: 14, SEQ ID NO: 10, SEQ ID NO: 18, SEQ ID NO: 22 or SEQ ID NO: 26; or
   (iii) both (i) and (ii).

20. An isolated nucleic acid molecule encoding the immunoconjugate of claim 14, wherein the nucleotide sequence encoding the immunoconjugate comprises SEQ ID NO: 30, SEQ ID NO: 32, SEQ ID NO: 34, SEQ ID NO: 36 or SEQ ID NO: 38.

21. The isolated nucleic acid molecule of claim 18, operably linked to a promoter.

22. An expression vector comprising the isolated nucleic acid molecule of claim 18.

23. An isolated host cell transformed with the expression vector of claim 22.

24. An isolated immunoconjugate comprising the monoclonal antibody of claim 1 and a therapeutic agent.

25. The isolated immunoconjugate of claim 24, wherein the therapeutic agent comprises a drug.

26. A chimeric antigen receptor (CAR) comprising the monoclonal antibody of claim 1.

27. The CAR of claim 26, wherein the monoclonal antibody is a scFv.

28. A bispecific antibody comprising the monoclonal antibody of claim 1.

* * * * *